(12) United States Patent
Jeppsen et al.

(10) Patent No.: US 9,671,392 B2
(45) Date of Patent: Jun. 6, 2017

(54) MULTISENSOR ARRAY FOR DETECTION OF ANALYTES OR MIXTURES THEREOF IN GAS OR LIQUID PHASE

(75) Inventors: Jan Oskar Jeppsen, Odense SV (DK);
Natalie Kostesha, Virum (DK);
Carsten Johnsen, Odense S (DK);
Kent Albin Nielsen, Odense SV (DK);
Anja Boisen, Birkerød (DK); Mogens Havsteen Jakobsen, Vanløse (DK)

(73) Assignee: Danmarks Tekniske Universitet, Lyngby (DK)

( * ) Notice: Subject to any disclaimer, the term of this patent is extended or adjusted under 35 U.S.C. 154(b) by 263 days.

(21) Appl. No.: 13/637,641

(22) PCT Filed: Mar. 31, 2011

(86) PCT No.: PCT/EP2011/055014
§ 371 (c)(1),
(2), (4) Date: Dec. 20, 2012

(87) PCT Pub. No.: WO2011/121077
PCT Pub. Date: Oct. 6, 2011

(65) Prior Publication Data
US 2013/0096030 A1   Apr. 18, 2013

Related U.S. Application Data

(60) Provisional application No. 61/319,449, filed on Mar. 31, 2010.

(51) Int. Cl.
*G01N 33/52*   (2006.01)
*C40B 40/04*   (2006.01)
(Continued)

(52) U.S. Cl.
CPC ......... *G01N 33/521* (2013.01); *C07D 495/04* (2013.01); *G01N 31/22* (2013.01);
(Continued)

(58) Field of Classification Search
None
See application file for complete search history.

(56) References Cited

U.S. PATENT DOCUMENTS

| 4,082,552 A | 4/1978 | Engler et al. |
| 4,598,979 A | 7/1986 | Sugiuchi et al. |

(Continued)

FOREIGN PATENT DOCUMENTS

| EP | 0490572 A1 | 6/1992 |
| WO | WO 00/26638 | 5/2000 |

(Continued)

OTHER PUBLICATIONS

Alstrøm et al., "Data Representation and Feature Selection for Colorimetric Sensor Arrays Used as Explosives Detectors" IEEE International Workshop on Machine Learning for Signal Processing, IEEE Press, 2011.

(Continued)

*Primary Examiner* — Kaijiang Zhang
(74) *Attorney, Agent, or Firm* — Knobbe, Martens, Olson and Bear, LLP

(57) ABSTRACT

The present invention relates to a multisensor array for detection of analytes in the gas phase or in the liquid phase, comprising at least two different chemo-selective compounds represented by the general formula (I) wherein the hetero atoms $X^1$-$X^4$ and the substituents $R^1$-$R^4$ are defined in the specification and the dashed bonds represent independently of each other either a single bond or a double bond. Said chemo-selective compounds are capable of individually changing physicochemical properties when exposed to analytes or analyte mixtures and these changes can be detected by a transducer or an array of transducers. The present invention does also relate to the use of at least two different chemo-selective compounds in a sensor array, a method for preparation of such sensor arrays and the use of (Continued)

said sensor arrays. Furthermore the present invention relates to methods for detecting and identifying analytes or mixtures thereof in the gas phase or in the liquid phase.

13 Claims, 3 Drawing Sheets

(51) Int. Cl.
C07D 495/04 (2006.01)
G01N 31/22 (2006.01)
G01N 33/53 (2006.01)
G01N 33/94 (2006.01)

(52) U.S. Cl.
CPC ......... G01N 33/5308 (2013.01); G01N 33/94 (2013.01); C40B 40/04 (2013.01)

(56) References Cited

U.S. PATENT DOCUMENTS

| | | | |
|---|---|---|---|
| 6,368,558 | B1 | 4/2002 | Suslick et al. |
| 6,495,102 | B1 | 12/2002 | Suslick et al. |
| 6,670,286 | B1 | 12/2003 | Yang et al. |
| 7,261,857 | B2 | 8/2007 | Suslick et al. |
| 7,824,619 | B1 * | 11/2010 | Aviram ................ G01N 27/126 422/88 |
| 2003/0082444 | A1 | 5/2003 | Kuhr et al. |
| 2003/0129085 | A1 | 7/2003 | Suslick et al. |
| 2005/0058009 | A1 | 3/2005 | Yang et al. |
| 2005/0171449 | A1 | 8/2005 | Suslick et al. |
| 2006/0183165 | A1 | 8/2006 | Zhang et al. |
| 2008/0000525 | A1 | 1/2008 | Shimura et al. |
| 2008/0050839 | A1 | 2/2008 | Suslick et al. |
| 2008/0199904 | A1 | 8/2008 | Suslick et al. |

FOREIGN PATENT DOCUMENTS

| | | |
|---|---|---|
| WO | WO 2007/132430 A2 | 11/2007 |
| WO | WO 2009/117613 A1 | 9/2009 |
| WO | WO 2009/149381 A2 | 12/2009 |
| WO | WO 2010/028057 A1 | 3/2010 |

OTHER PUBLICATIONS

Ashton et al., "Cyclophanes and [2]Catenanes as Ligands for Transition Metal Complexes: Syntheses, Structure, Absorption Spectra, and Excited State and Electrochemical Properties" Chemistry—A European Journal, 1998, pp. 590-607, vol. 4.
Baffreau et al., "New Versatile Building Block for the Construction of Tetrathiafulvalene-Based Donor-Acceptor Systems" Organic Letters, 2006, pp. 1307-1310, vol. 8, No. 7.
Battiston et al., "A Chemical Sensor Based on Microfabricated Cantilever Array with Simultaneous Resonance-Frequency and Bending Readout" Sensors and Actuators B: Chemical, 2001, pp. 122-131, vol. 77.
Cundall et al., "Vapour Pressure Measurements on Some Organic High Explosives" Journal of the Chemical Society, Faraday Trans. 1, 1978, Issue 74, pp. 1339-1345.
Damgaard et al., "Synthesis of Linear Oligo-TTFs and their [2]rotaxanes with cyclobis(paraquat-p-phenylene)" Journal of Materials Chemistry, 2000, Issue 10, pp. 2249-2258.
Di Natale et al., "Porphyrins-based Opto-Electronic Nose for Volatile Compounds Detection" Sensors and Actuators B: Chemical, 2000, pp. 122-131, vol. 65.
Dionne et al., "Vapor Pressure of Explosives" Journal of Energetic Materials, 1986, pp. 447-472, vol. 4.
Geng et al., "A-C≡C-TTF-C≡C-A Tetrathiafulvalene Derivative: Synthesis and Property" Imaging Science and Photochemistry, 2009, pp. 32-37, vol. 27.
Gui et al., Detection and Discrimination of Low Concentration Explosives Using MOS Nanoparticle Sensors: Journal of Hazardous Materials, 2009, Pates 1090-1035, vol. 164.
Janzen et al., "Colorimetric Sensor Arrays for Volatile Organic Compounds" Analytical Chemistry. 2006, pp. 3591-3600, vol. 78.
Jensen et al., "Self-Assembled Monolayers of Mono-Tetrathiafulvalene Calix[4]pyrroles and their Electrochemical Sensing of Chloride" Chemistry—European Journal, 2009, pp. 8128-8133, vol. 15.
Jeppesen et al., "Pyrrolo Annelated Tetrathiafulvalenes: The Parent Systems" Organic Letters, 1999, pp. 1291-1294, vol. 1.
Jeppesen et al., "Pyrrolo-Annelated Tetrathiafulvalenes:The Parent Systems" Journal of Organic Chemistry, 2000, pp. 5794-5805, vol. 65.
Kim et al., "A Chloride-anion Insensitive Colorimetric Chemosensor for Trinitrobenzene and Picric Acid" Analytical and Bioanalytical Chemistry. 2009, pp. 393-400.
Kostesha et al., "Development of the Colorimetric Sensor Array for Detection of Explosives and Volatile Organic Compounds in Air" Proc. SPIE 7673, Advanced Environmental, Chemical, and Biological Sensing Technologies VII, vol. 7673, article id. 76730I (2010).
Liao et al., "Cyclic Conductance Switching in Networks of Redox-Active Molecular Junctions" Nano Letters, 2010, pp. 759-764, vol. 10.
Lyskawa et al., "Tetrathiafulvalene-Based Podands Bearing One or Two Thiol Functions: Immobilization as Self-Assembled Monolayers or Polymer Films, and Recognition Properties" Tetrahedron, 2006, pp. 4419-4425, vol. 62.
Nielsen et al., "Tetra-TTF Calix[4]pyrrole: A Rationally Designed Receptor for Electron-Deficient Neutral Guests" Journal of the American Chemical Society, 2004, pp. 16296-16297, vol. 126.
Nielsen et al., "Tetrathiafulvalene-Calix[4]pyrroles: Synthesis Anion Binding, and Electrochemical Properties" Journal of the American Chemical Society, 2006, pp. 2444-2451, vol. 128.
Nielsen et al., "Binding Studies of Tetrathiafulvalene-Calix[4]pyrroles with Electron-Deficient Guests" Tetrahedron, 2008, pp. 8449-8463, vol. 64.
Nielsen et al., "Tetrathiafulvalene Porphyrins" Chemistry—A European Journal, 2009, pp. 506-516, vol. 15.
Park et al., "Positive Homtropic Allosteric Receptors for Neutral Guests: Annulated Tetrathiafulvalene-Calix[4]pyrroles as Colorimetric Chemosensors for Nitroaromatic Explosives" Chemistry—A European Journal , 2010, pp. 848-854, vol. 16.
Petersen et al., "Characterization of a Byproduct in the Alkylation of DMIT: Alkylation on the Least Nucleophilic Sulfur Atom" European Journal of Inorganic Chemistry, 2006, pp. 3099-3104.
Rakow et al., "Molecular Recognition and Discrimination of Amines with Colorimetric Array" Angewandte Chemie International Edition, 2005, pp. 4528-4532, vol. 44.
Simonsen et al., "Sequential Functionalisation of Bis-Protected Tetrathiafulvalene-Dithiolates" Synthesis, 1996, pp. 407-418.
Simonsen et al., "Tetrathiafulvalene Belts with Large Cavities" Angewandte Chemie International Edition, 1999, pp. 1417-1420, vol. 38.
Surpateanu et al., "A Competitive Sensing System Based on Cyclobis(paraquat-p-phenylene) and a New β-cyclodextrix-tetrathiafulvalene Derivative" Supramolecular Chemistry, 2009, pp. 372-378, vol. 21.
Suslick et al., "Colorimetric Sensor Arrays for Molecular Recognition" Tetrahedron, 2004, pp. 11133-11138, vol. 60.
Svenstrup et al., "The Chemistry of TTFTT; 1: New Efficient Synthesis and Reactions of Tetrathiafulvalene-2,3,6,7-tetrathiolate (TTFTT): An Important Building Block in TTF-Syntheses" Synthesis, 1994, pp. 809-812.
Wang et al., "The Synthesis and Electrochemical Properties of a New Tetra-(crown-ether-thiafulvalene)-annulated Phthalocyanine Derivative" Dyes and Pigments, 2009, pp. 40-44, vol. 81.
Wang, "A Novel Highly Selective Multisignal Chemosensor Based on Redox Fluorescence Switch" Abstract (Department of Chemistry, Huaibei Coal Teacher College,Huaibei 235000,Anhui,China) 2009.

(56) References Cited

OTHER PUBLICATIONS

Wang et al., "Colorimetric and Electrochemical $Pb^{2+}$ Detection by Imine-Bridged Tetrathiafulvalene-pyridine Derivatives" Science in China Series B: Chemistry, 2009, pp. 765-770, vol. 52.

Yinon, "Detection of Explosives by Electronic Noses" Analytical Chemistry, 2003, pp. 99A-105A.

Zhang et al., "A Colorimetric Sensor Array for Organics in Water" Journal of the American Chemical Society, 2005, pp. 11548-11549, vol. 127.

Zhang et al., "Colorimetric Sensor Arrays for the Analysis of Beers: A Feasibility Study" Journal of Agricultural and Food Chemistry, 2006, pp. 4925-4931, vol. 54.

Zhang et al., "Colorimetric Sensor Array for Soft Drink Analysis" Journal of Agricultural and Food Chemistry, 2007, pp. 237-242, vol. 55.

\* cited by examiner

Before exposure    After exposure    Difference map

MULTISENSOR ARRAY FOR DETECTION OF ANALYTES OR MIXTURES THEREOF IN GAS OR LIQUID PHASE

CROSS REFERENCE TO RELATED APPLICATIONS

This application is a U.S. National Phase Application of PCT International Application Number PCT/EP2011/055014, filed on Mar. 31, 2011, designating the United States of America and published in the English language, which is an International Application of and claims the benefit of priority to U.S. Provisional Application No. 61/319,449, filed on Mar. 31, 2010. The disclosures of the above-referenced applications are hereby expressly incorporated by reference in their entireties.

FIELD OF THE INVENTION

The present invention relates to a multisensor array for detection of analytes in the gas phase or in the liquid phase, comprising at least two different chemo-selective compounds. In particular the present invention relates to a sensor array for detection of organic compounds, inorganic compounds, anions and metal ions in the gas phase or in the liquid phase, comprising at least two different chemo-selective compounds. Said chemo-selective compounds are capable of individually changing physicochemical properties when exposed to analytes or analyte mixtures and these changes can be detected by a transducer or an array of transducers. The present invention does also relate to the use of at least two different chemo-selective compounds in a sensor array, a method for preparation of such sensor arrays and the use of said sensor arrays. Furthermore the present invention relates to methods for detecting and identifying analytes or mixtures thereof in the gas phase or in the liquid phase.

BACKGROUND OF THE INVENTION

One of the most traditional and common technologies that involves detection and classification of volatile organic compounds in gas phase is an electronic nose or an electronic tongue for liquid sensing. The electronic nose is a device that combines a chemical-sensing and pattern-recognition systems; in nature it can in principle be the sensing organ of an animal like a nose of a bomb-sniffing dog. Conventional approaches to chemical sensors arrays have traditionally made use of a "lock-and-key" design, wherein a specific receptor is synthesized in order to strongly and highly selectively bind the analyte of interest. Nevertheless, the traditionally applied electronic nose technique is expensive and has certain limitations due to detection problems at low analyte concentrations, temperature and humidity requirements. Furthermore, the technical equipment can be rather heavy and difficult to move into new locations where detection is required.

Sensor arrays, in particular colorimetric sensor arrays, which involve an artificial nose having an array of at least a first dye and a second dye in combination and having a distinct spectral response to an analyte are well known in the prior art. Typical examples of sensor arrays comprising at least two different chemo-selective dyes, where the dyes are from the group of porphyrin, chlorin, chlorophyll, phthalocyanine, or salen, in particular metalated or non-metalated porphyrines and derivatives thereof are known for example from U.S. Pat. Nos. 6,495,102, 6,368,558 and 7,261,857 in which the sensor arrays are particular useful for detecting metal ligating vapors. US2000050839 describes an apparatus and method including a colorimetric array comprising porphyrinogen dyes to detect lung cancer via exhaled breath. US20080199904 describes an apparatus and method including a colorimetric array comprising porphyrinogen dyes to detect and identifying microorganisms. WO2010028057 describes a colorimetric array comprising of nanoporous pigments based on porphyrinogen dyes. A sensor device comprising porphyrinogen derivatives having binding affinity for explosives is known from WO2007132430.

The chemical diversity of the metalated or non-metalated porphyrines and the derivatives thereof described above is relatively limited and only well suited for the detection of metal ligating analytes. The porphyrinogen derivatives having high binding affinity for explosives suffers from a strong cross-reactivity with other electron-deficient guests like chloride ions (JACS, 2004, 126, 16296-16297) (JACS, 2006, 128, 2444-2451). Furthermore, the described sensor molecules are relatively complex molecules with a limited chemical diversity.

Also operational constraints for example environmental changes such as temperature, humidity and large number of interferants giving rise to false positives and false negatives due to too low sensitivity makes it highly desirable with a new class of sensor molecules to provide an improved sensor array in particular a more efficient and/or reliable sensor array.

SUMMARY OF THE INVENTION

To solve the above mentioned problems of the prior art an emerging strategy that is complementary to the conventional chemical sensing approach involves the use of less specific sensor molecules with a higher degree of cross reactivity. Such sensor arrays can potentially recognize specific molecules precisely and can be applied in many areas of research and industry, such as food quality analysis, medical diagnostics, explosives and toxins detection and environmental monitoring. For practical purposes, such sensing molecules should be relatively simple and cheap while at the same time allow for a large structural diversity.

The present invention relates to multisensory arrays for detection and/or identification of analyte(s) and mixtures thereof such as, for example, explosives, drugs, narcotics, chemicals poisonous, toxins, toxic or relatively toxic compounds, or illegal compounds, in the gas phase and in the liquid phase. By way of examples said arrays can be used to screen for relevant explosives in a complex background as well as to distinguish mixtures of volatile organic compounds distributed in the gas phase.

The sensing is based on at least two chemo-selective compounds of the hetero atom-containing compounds represented by the general structure I)

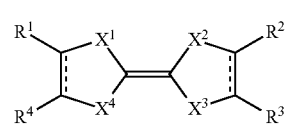

wherein $X^1$, $X^2$, $X^3$, and $X^4$ each independently represents a hetero atom selected from nitrogen being NH or substituted nitrogen, oxygen, sulfur, selenium, and tellurium; and $R^1$, $R^2$, $R^3$, and $R^4$ each independently represents hydrogen, halogen, or an organic or metal organic group; and the dashed bonds represent independently of each other either a single bond or a double bond.

These compounds can change their physicochemical properties when exposed to the analyte(s) in gasses or liquids, and these changes can then be detected by a transducer. As will be explained later different transduction methods are foreseen. One example is a colorimetric sensor array where colour change in the visible spectrum of at least two compounds is used as the detection mechanism.

Such sensor arrays have a wide area of application: in military, police, industry, medicine or by civilians—indoor or outdoor tests. The sensor arrays are capable of detecting and identifying chemical compounds belonging to different classes, like amines, alcohols, carboxylic acids, ketones, sulphides, and thiols. The array can also be applied for screening of the spoilage and/or freshness of food, of vapour poisoning compounds in industry or houses, and for monitoring the environment.

The colorimetric sensor array according to the present invention is a rapid method for detection of analytes, in some applications the responses can be achieved within 30-60 sec. Another advantage of the present invention is that the colorimetric sensor array is an inexpensive approach, and can potentially be produced as single use disposables.

Thus, an object of the present invention relates to a multisensor array for detection of analytes or mixtures thereof in the gas phase or in the liquid phase, comprising at least two different chemo-selective compounds represented by the general formula I), wherein $X^1$ to $X^4$ as well as $R^1$ to $R^4$ have the above meanings, and the dashed bonds represent independently of each other either a single bond or a double bond.

In particular, it may be seen as an object of the present invention to provide a sensor array that solves the above mentioned problems of the prior art.

A second object of the present invention relates to use of at least two different chemo-selective compounds represented by the general formula I), wherein $X^1$ to $X^4$ as well as $R^1$ to $R^4$ have the above meanings and the dashed bonds represent independently of each other either a single bond or a double bond; in a multisensor array for detection of analytes and mixtures thereof in gas or liquid phase.

A third object of the present invention relates to a method for preparation of the multisensor array according to the present invention, wherein at least two different chemo-selective compounds having the general formula I) are immobilized on a solid support.

In a fourth object the present invention relates to use of the multisensor array according to the present invention for detection and/or identification of an analyte or mixtures thereof in gas or liquid phase.

In a fifth object the present invention relates to a method of detecting and identifying an analyte or mixtures thereof in a gas or liquid, comprising:
  obtaining a first measurement of the sensor array according to the present invention before exposure to (in absence of) the analyte(s),
  exposing the sensor array to the analyte(s) in gas or liquid phase,
  obtaining a second measurement of the multi sensor array after exposure to the analyte(s), and
  analyzing a difference between the first measurement and the second measurement.

Although the present invention will be described in connection with specified aspect and embodiments, it should not be construed as being in any way limited to the presented aspects or embodiments. In the context of the claims, the terms "comprising" or "comprises" do not exclude other possible elements or steps. Also, the mentioning of references such as "a" or "an" etc. should not be construed as excluding a plurality. Furthermore, individual features mentioned in different aspect or claims, may possibly be advantageously combined, and the mentioning of these features in different aspect or claims does not exclude that a combination of features is not possible and advantageous. The different aspect and embodiments of the present invention may each be combined with any of the other aspects. These and other aspects of the invention will be apparent from and elucidated with reference to the embodiments described hereinafter.

BRIEF DESCRIPTION OF THE FIGURES

The sensor array according to the invention will now be described in more detail with regard to the accompanying figures. The figures show one way of implementing the present invention and is not to be construed as being limiting to other possible embodiments falling within the scope of the attached claim set.

Figure 1:
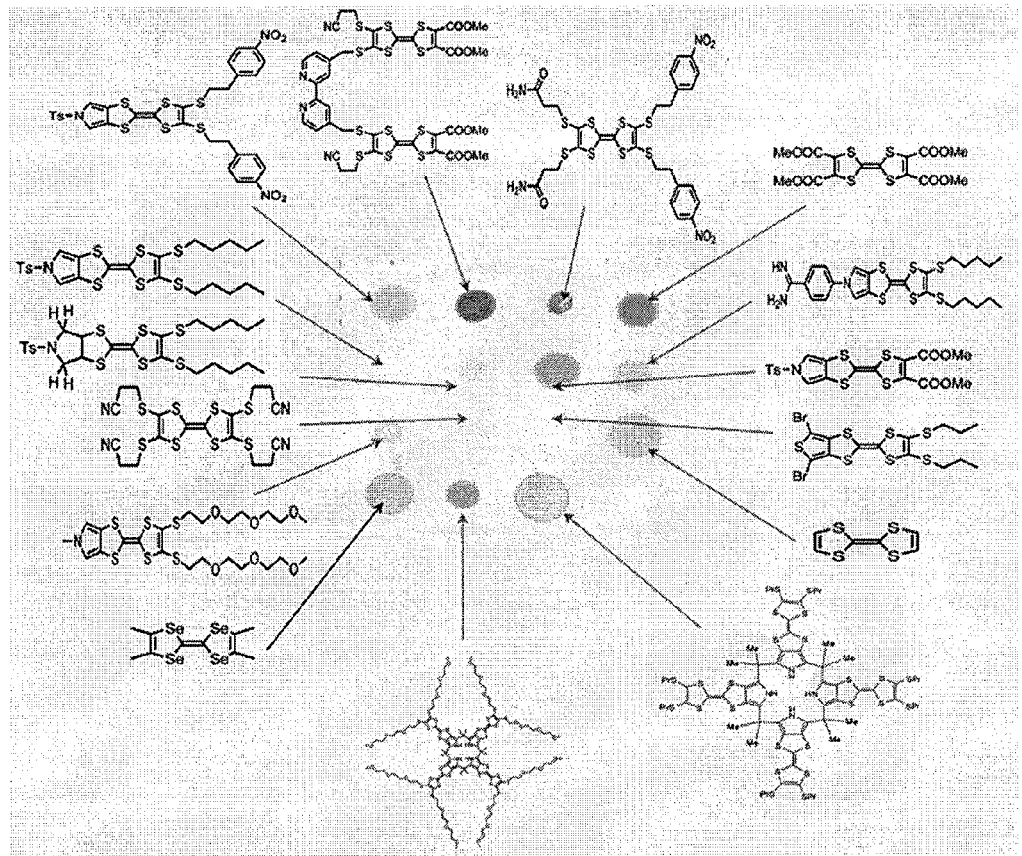
FIG. 1 shows a colorimetric sensor array according to the present invention where one possible location of each of fifteen different individual chemo-selective compounds is shown (before exposure to an analyte).

The present invention will now be described in more detail in the following.

DETAILED DESCRIPTION OF THE INVENTION

Thus, an object of the present invention relates to a multisensor array for detection of an analyte or mixtures thereof, such as organic compounds, inorganic compounds, anions and metal ions, in the gas phase or in the liquid phase, comprising at least two different chemo-selective compounds represented by the general formula I)

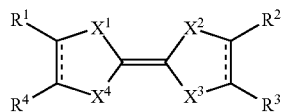

wherein
X$^1$, X$^2$, X$^3$, and X$^4$ each independently represents a hetero atom selected from nitrogen being NH or substituted nitrogen, oxygen, sulfur, selenium, and tellurium; and
R', R$^2$, R$^3$, and R$^4$ each independently represents hydrogen, halogen, or an organic or metal organic group; and
the dashed bonds represent independently of each other either a single bond or a double bond.

The mammalian olfactory system contains approximately 1000 different olfactory receptor genes and, upon odor stimulation, responses from many receptors are sent to the olfactory bulb and then to the olfactory cortex for processing. Furthermore, recent experiments have shown that the olfactory receptors are not highly selective toward specific analytes; in fact, one receptor responds to many analytes and many receptors respond to any given analyte. Pattern recognition methods are thus thought to be a dominant mode of olfactory signal processing. A multisensory array is an array of chemo-selective compounds applied on a solid support, simulating the mammalian olfactory system. Like the mammalian olfactory system the array has the capability to identify organic compounds, inorganic compounds, anions and metal ions, in the gas phase or in the liquid phase, because each chemo-selective compound is capable of individually changing physicochemical properties when exposed to analytes or analyte mixtures. These changes of physicochemical properties can be detected by a transducer or an array of transducers. For example, changes in colour can be detected either by transmission measurements or by reflection measurement using e.g. standard ccd cameras or flatbed scanner. Other transduction methods can measure the change in mass e.g. using cantilever arrays by change in resonance frequency, or acoustic wave devices, or quartz crystal microbalances, change in surface stress using cantilevers, change of surface potential using MOSFET arrays, change in conductivity e.g. using conductive polymer arrays, change in molecular vibrations using raman, surface enhanced raman, and infrared spectroscopy. The individual change of each chemo-selective compound in the array is then analyzed by pattern recognition methods to analyze, classify the analyte or analyte mixture.

Useful chemo-selective compounds of this invention include very simple compounds, like the compounds numbered 12, 13 and 20 as shown in Table 1 and in the examples section, which at the same time allow a very high structural diversity, which is also evident from Table 1. Furthermore, many compounds of this class are commercially available or can be synthesized by known methods. The number of potential chemo-selective compounds reported in the literature is in the thousands, matching the complexity of the mammalian olfactory system and making it possible to develop a universal sensor array for all purposes.

Said chemo-selective compounds are capable of individually changing physicochemical properties when exposed to analytes or analyte mixtures and these changes can be detected by a transducer or an array of transducers. Thus, chemo-selective compounds change physicochemical properties when exposed to the analyte(s) in gasses or liquids, and those changes can then be detected. Each of the compounds reacts chemo-selectively with the analyte via non-covalent interactions (host-guest interactions) and has its own fingerprint in response to the presented analyte. Therefore, by using an array of different chemo-selective compounds, analytes of very different nature, but also clearly closely related analyte molecules can be distinguished and detected. As illustrated in Example 4, more than one chemo-selective compound may be needed to distinguish between a false positive and a real positive. In the mentioned Example this is due to the presence of chloride anions existing together with DNT in the sample. In Example 4 we have used 15 different chemo-selective compounds to be able to distinguish between operational constraints like the environmental background from temperature effect and interferants like vapors from common organic solvents during the detection of the explosive DNT.

The present use of an array of chemo-selective compounds differs from conventional approaches to chemical sensors arrays which traditionally have made use of a "lock-and-key" design, wherein a specific receptor is synthesized in order to strongly and highly selectively bind the analyte of interest. The number of chemo-selective compounds needed to address operational constraints for example environmental changes such as temperature, humidity and other interferants giving rise to false positives and false negatives can be optimized according to the complexity of the particular application.

The chemo-selective compounds of this invention have capability to selectively recognize specific analytes; this recognition is a function of intermolecular interactions, basically weak, non-covalent interactions or donor-acceptor interactions. However, only weak, non-covalent interactions can occur between the hetero atoms of general formula I) and neutral target molecules like DNT, TNT or toluene. In order to increase sensing properties, different functional groups, such as dyes, can be incorporated by changing the substituents R$^1$-R$^4$ of the compounds of general formula I). These modifications will amplify the weak, non-covalent interactions to the respective analytes and increase/decrease the polarity, solubility and redox properties of compounds of the general formula I); the diversity of compounds is presented in Table 1 (below). For example, tetraTTF-calix[4]pyrrole (number 15 in Tab. 1) is one of the promising molecules that has good anion binding affinity and selectivity in polar solvents. The optically active calix[4]pyrrole-based sensor has already been applied for the detection of 1,3,5-trinitrobenzene, tetrafluoro-p-benzoquinone, tetrachloro-p-benzoquinone, p-benzoquinone, and 1,3,5-trinitrophenole.

The terms "gas phase" and "liquid phase" have their ordinary meanings. The liquid phase also includes heterogeneous suspensions of particles in a medium.

Thus, one aspect the present invention relates to a sensor array for detection of organic compounds, inorganic compounds, anions and metal ions in the gas phase or in the liquid phase, comprising at least two different chemo-selective compounds represented by the general formulas 1) and 2)

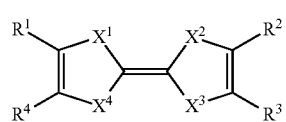

-continued

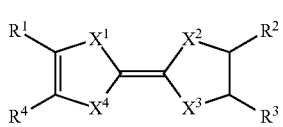

wherein
  $X^1$, $X^2$, $X^3$, and $X^4$ each independently represents an atom selected from nitrogen being NH or substituted nitrogen, oxygen, sulfur, selenium, and tellurium; and
  R', $R^2$, $R^3$, and $R^4$ each independently represents hydrogen, halogen, or an organic, or metal organic group.

Another aspect of the present invention relates to a sensor array according to the present invention comprising at least fifteen different chemo-selective compounds represented by the general formula I), wherein $X^1$, $X^2$, $X^3$, and $X^4$ each independently represents a hetero atom selected from nitrogen being NH or substituted nitrogen, oxygen, sulfur, selenium, and tellurium; and R', $R^2$, $R^3$, and $R^4$ each independently represents hydrogen, halogen, or any organic or metal organic group; and the dashed bonds represent independently of each other either a single bond or a double bond.

In still another aspect the present invention relates to the sensor array according to the present invention comprising at least fifteen different chemo-selective compounds represented by the general formulas 1) and 2), wherein $X^1$ to $X^4$ as well as $R^1$ to $R^4$ have the above meanings.

In another aspect according to the present invention hetero atoms $X^1$, $X^2$, $X^3$, and $X^4$ of the general formulas I) and 1) and 2) each independently represents a hetero atom selected from nitrogen being NH or nitrogen substituted by $C_1$-$C_4$-alkyl or chlorophenylmethyl, oxygen, sulfur, selenium, and tellurium; and
  $R^1$, $R^2$, $R^3$, and $R^4$ each independently represents hydrogen; halogen; $C_1$-$C_4$-alkyl; $C_1$-$C_{20}$-alkylsulfanyl; 2-substituted ethylsulfanyl wherein the substituents are selected from the group of carboxamide, cyano, hydroxy, amino, (N-benzoyl)amino, halogen, methylthio, phenylcarboxy, phenoxycarbonyl and 4-nitrophenyl; 2-(methylthio)ethylsulfanyl copper bromide; benzoylsulfanyl; $C_1$-$C_4$-alkoxycarbonyl; cyano; carboxy; unsubstituted phenyl or phenyl substituted by $C_1$-$C_4$-alkoxy or halogen; benzyl; halogen; and (4'-{[7-(2-cyanoethylthio)-2,3-dimethoxy-carbonyl-6-thio-methylene]tetrathiafulvalene}-4-bipyridine)methylsulfanyl; or
  $R^1$ and $R^4$ together form a group selected from

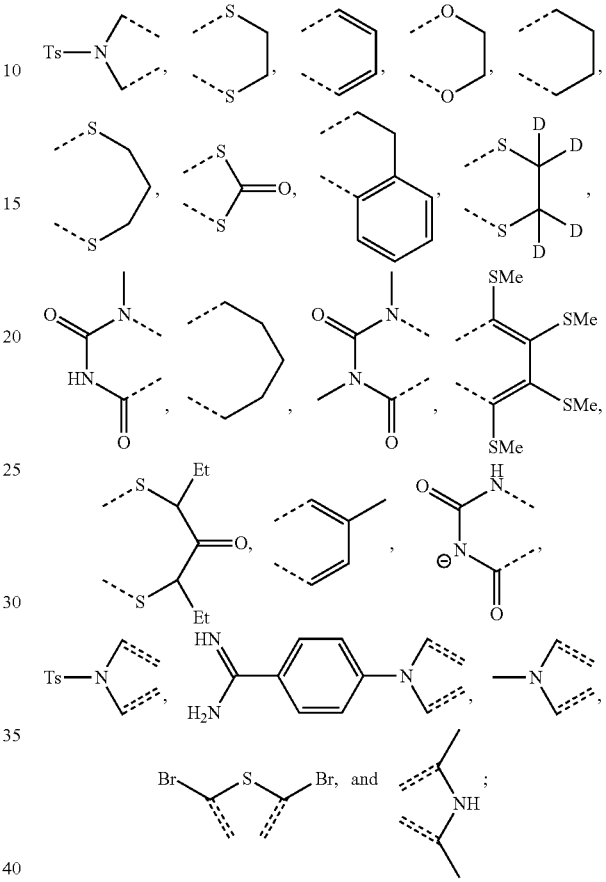

$R^2$ and $R^3$ together form a group selected from:

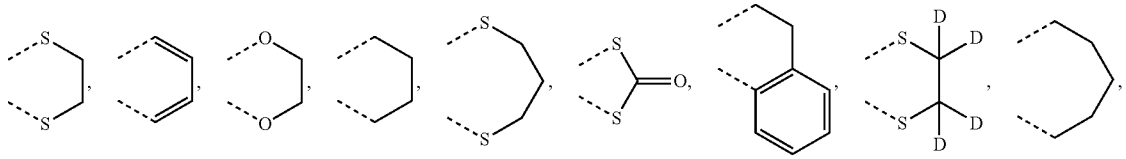

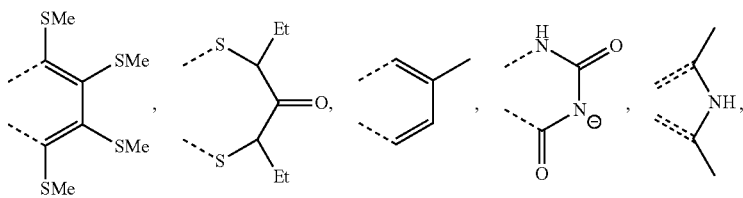

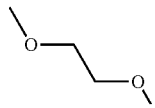

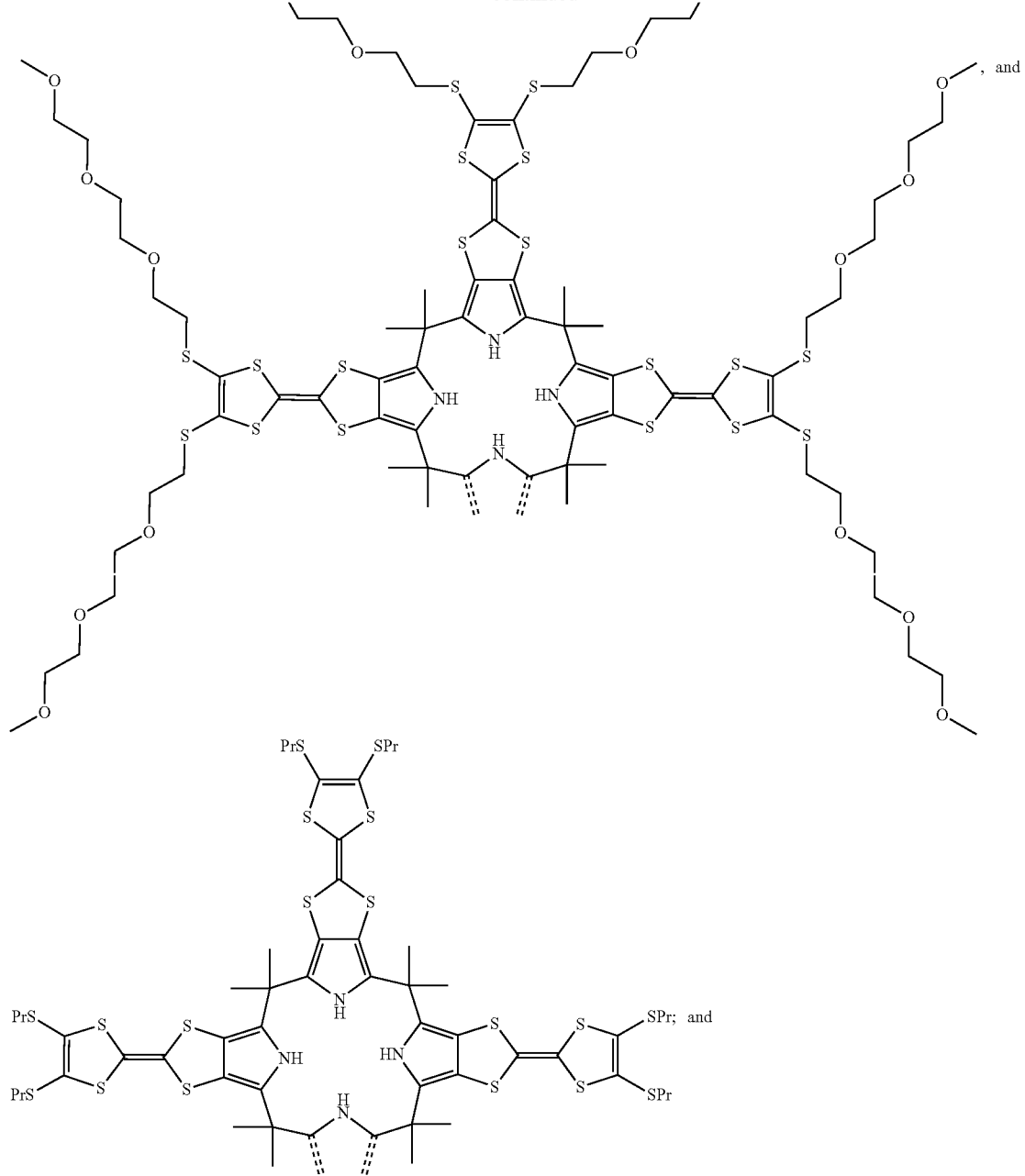

the dashed bonds represent independently of each other either a single bond or a double bond.

The substituent groups such as $C_1$-$C_4$-alkyl, $C_1$-$C_{20}$-alkylsulfanyl and $C_1$-$C_4$-alkoxycarbonyl have their ordinary meaning as commonly used in the field of organic chemistry.

In another aspect according to the present invention the hetero atoms $X^1$, $X^2$, $X^3$, and $X^4$ of the general formulas I) and 1) and 2) each independently represents a hetero atom selected from oxygen, sulfur and selenium.

In another aspect according to the present invention the hetero atoms $X^1$, $X^2$, $X^3$, and $X^4$ of the general formulas I) and 1) and 2) each independently represents a hetero atom selected from oxygen and sulfur.

In another aspect according to the present invention the hetero atoms $X^1$, $X^2$, $X^3$, and $X^4$ of the general formulas I) and 1) and 2) each independently represents an hetero atom selected from sulfur and selenium.

In another aspect according to the present invention the hetero atoms $X^1$, $X^2$, $X^3$, and $X^4$ of the general formulas I) and 1) and 2) each represents a sulfur atom.

In another aspect according to the present invention the substituents $R^1$, $R^2$, $R^3$, and $R^4$ of the general formulas I) and 1) and 2) each independently may represent halogen. By halogen is meant fluorine, chlorine, bromide, and iodine.

In another aspect according to the present invention the substituents $R^1$, $R^2$, $R^3$, and $R^4$ of the general formulas I) and 1) and 2) each independently represents hydrogen or an organic group.

In another aspect according to the present invention the compounds are selected from general formula 1), wherein $R^1$ is a substituent selected from hydrogen; halogen; $C_1$-$C_4$-alkyl such as for example methyl, ethyl, propyl and butyl; $C_1$-$C_{20}$-alkylsulfanyl such as for example methylsulfanyl, ethylsulfanyl, pentylsulfanyl, decylsulfanyl, dodecylsulfanyl, hexadecylsulfanyl, octadecylsylfanyl; 2-substituted ethylsulfanyl wherein the substituents are selected from the group of carboxamide, cyano, hydroxy, amino, (N-benzoyl)amino, halogen, methylthio, phenylcarboxy, phenoxycarbonyl such as for example 2-(carboxamide)ethylsulfanyl, 2-cyanoethylsulfanyl, 2-hydroxyethylsulfanyl, 2-chloroethylsulfanyl, 2-(methylthio)ethylsulfanyl, 2-(phenylcarboxy)-ethylsulfanyl, 2-(phenoxycarbonyl)-ethylsulfanyl, 2-bromoethylsulfanyl, 2-aminoethylsulfanyl; 2-(N-benzoyl)amino-ethylsulfanyl, 2-(methylthio)ethylsulfanyl copper bromide; benzoylsulfanyl; methoxycarbonyl; cyano; carboxy; phenyl; benzyl; phenyl para-substituted by methoxy or halogen such as for example p-methoxyphenyl, p-bromophenyl, p-Chlorophenyl; and (4'-{[7-(2-cyanoethylthio)-2,3-dimethoxycarbonyl-6-thio-methylene]tetrathiafulvalene}-4-bipyridine)methylsulfanyl;

$R^2$ is a substituent selected from hydrogen; halogen; $C_1$-$C_4$-alkyl; $C_1$-$C_{20}$-alkylsulfanyl; 2-substituted ethylsulfanyl wherein the substituents are selected from the group of cyano, hydroxy, amino, (N-benzoyl)amino, halogen, methylthio, phenylcarboxy, phenoxy-carbonyl, (4-nitrophenyl) such as for example 2-(4-nitrophenyl)ethylsulfanyl, 2-cyanoethylsulfanyl, 2-hydroxyethylsulfanyl, 2-chloroethylsulfanyl, 2-(methylthio)-ethylsulfanyl, 2-(phenylcarboxy)-ethylsulfanyl, 2-bromoethylsulfanyl, 2-(phenoxy-carbonyl)-ethylsulfanyl, 2-(N-benzoyl)amino-ethylsulfanyl, 2-aminoethylsulfanyl; benzoylsulfanyl; cyano; carboxy; methoxycarbonyl; phenyl; benzyl; and phenyl para-substituted by methoxy or halogen;

$R^3$ is a substituent selected from hydrogen; halogen; $C_1$-$C_4$-alkyl; $C_1$-$C_{20}$-alkylsulfanyl; 2-substituted ethylsulfanyl wherein the substituents are selected from the group of cyano, hydroxy, amino, (N-benzoyl)amino, halogen, methylthio, phenylcarboxy, phenoxycarbonyl, (4-nitrophenyl); benzoylsulfanyl; methoxycarbonyl; cyano; carboxy; phenyl and phenyl para-substituted by halogen;

$R^4$ is a substituent selected from hydrogen; halogen; $C_1$-$C_4$-alkyl; $C_1$-$C_{20}$-alkylsulfanyl; 2-substituted ethylsulfanyl wherein the substituents are selected from the group of cyano, carboxamide, hydroxy, amino, (N-benzoyl)amino, halogen, methylthio, phenylcarboxy, phenoxycarbonyl; benzoylsulfanyl; benzyl; methoxycarbonyl; cyano; and carboxy; or $R^1$ and $R^4$ together form a group selected from

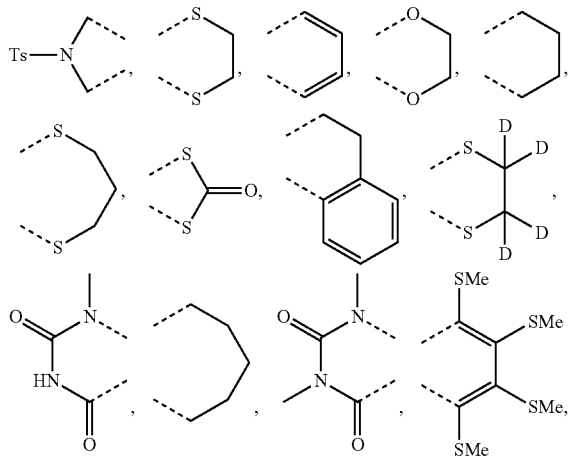

-continued

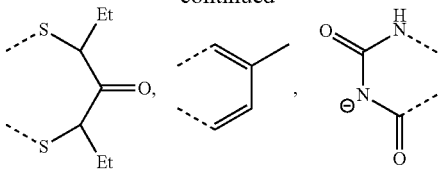

$R^2$ and $R^3$ together form a group selected from:

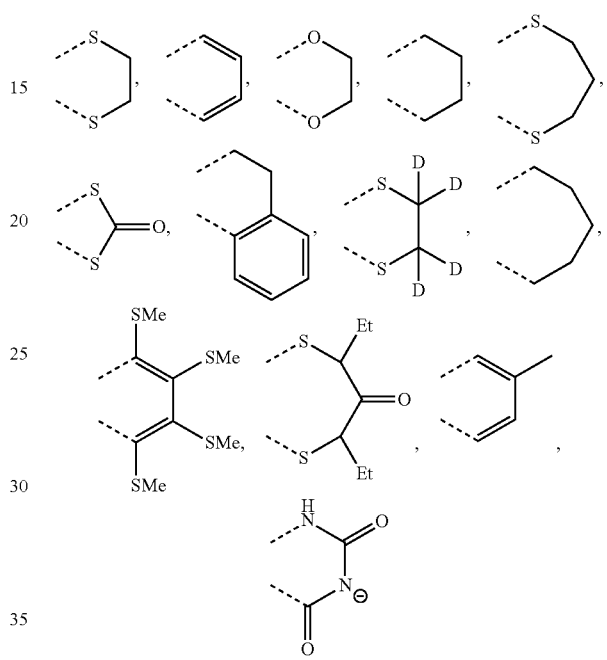

In another aspect according to the present invention the compounds are selected from general formula 2), wherein $R^1$ is a substituent selected from $C_1$-$C_{20}$-alkylsulfanyl such as for example propylsulfanyl; 2-substituted ethylsulfanyl wherein the substituent is 2-(2-methoxyethoxy)ethoxy;

$R^2$ is a substituent selected from methoxycarbonyl; $C_1$-$C_{20}$-alkylsulfanyl such as for example propylsulfanyl and pentylsulfanyl; and 2-substituted ethylsulfanyl wherein the substituents are selected from the group of 4-nitrophenyl and 2-(2-methoxyethoxy)-ethoxy;

$R^3$ is a substituent selected from $C_1$-$C_{20}$-alkylsulfanyl such as for example propylsulfanyl, pentylsulfanyl; 2-substituted ethylsulfanyl wherein the substituents are selected from the group of 4-nitrophenyl and 2-(2-methoxyethoxy)ethoxy; and methoxycarbonyl;

$R^4$ is a substituent selected from $C_1$-$C_{20}$-alkylsulfanyl such as for example propylsulfanyl; 2-substituted ethylsulfanyl wherein the substituent is 2-(2-methoxyethoxy)ethoxy; or $R^1$ and $R^4$ together form a group selected from:

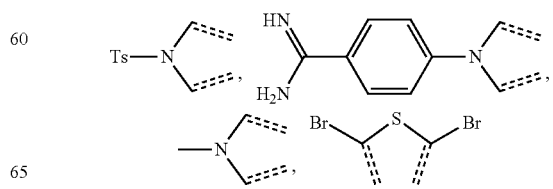

$R^2$ and $R^3$ together form a group selected from:
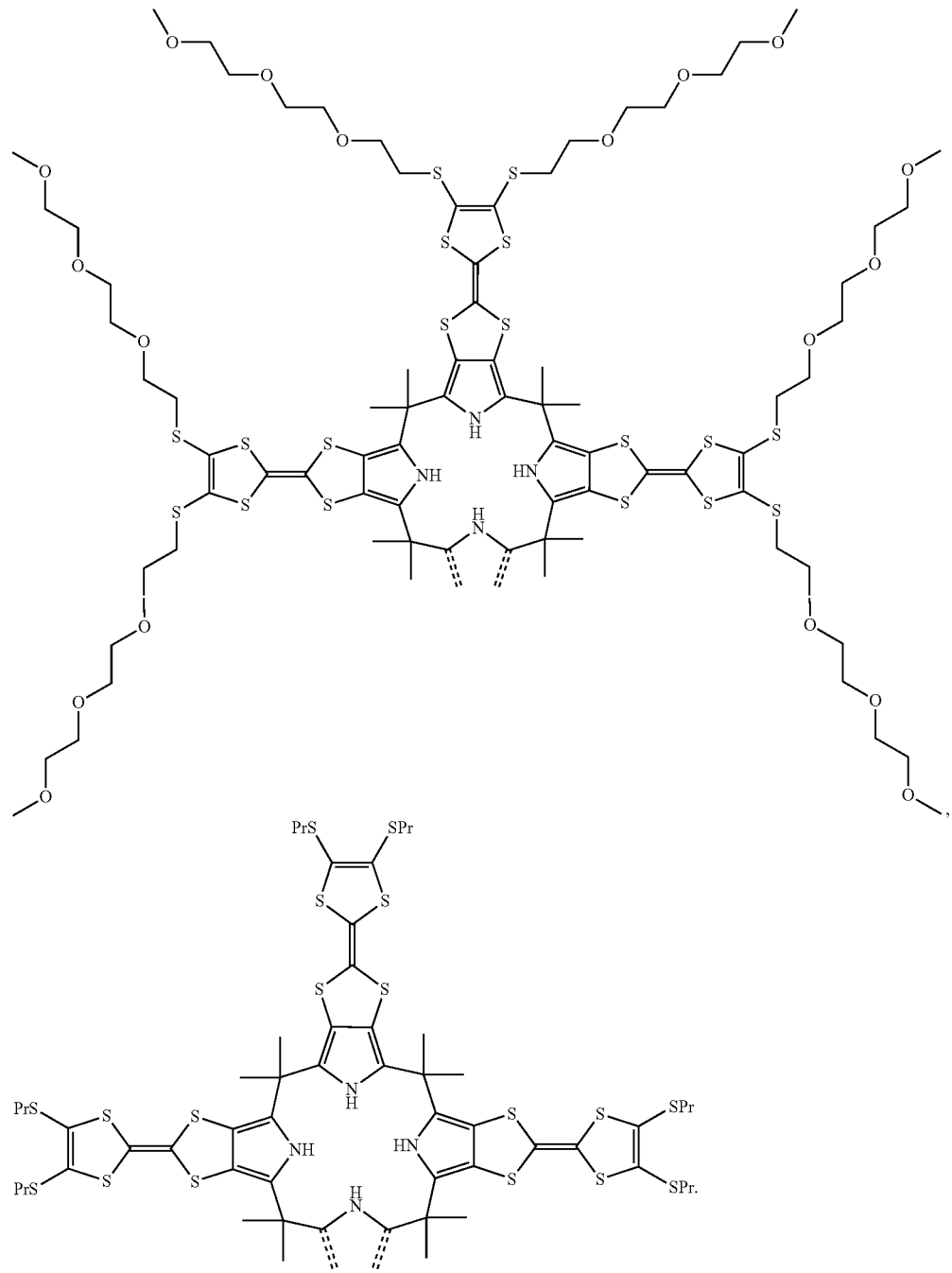
Some interesting compounds according to the present invention and its different aspects can be found in Table 1 below.

TABLE 1

| Comp. # | CAS-nr.: | Formula | $M_w$ | Structure | Substituents | Ref. |
|---|---|---|---|---|---|---|
| 1 | NA | $C_{13}H_{25}N_3O_6S_7$ | 760.00 | (structure: bis[2-(4-nitrophenyl)ethylsulfanyl]-substituted tetrathiafulvalene fused with Ts-N-pyrrole) | $R^1$ and $R^4$ together form: Ts—N⟨ ⟩; $R^2 = R^3 =$ 2-(4-Nitrophenyl)-ethylsulfanyl | Ex |
| 2 | NA | $C_{38}H_{30}N_4O_8S_{12}$ | 1055.45 | (structure: bis-TTF system linked by 2,2'-bipyridine with cyanoethylthio and COOMe substituents) | $R^1 =$ (4'-{[7-(2-Cyanoethylthio)-2,3-dimethoxy-carbonyl-6-thio-methylene]-tetrathiafulvalene}-4-bipyridine)methylsulfanyl | Ex |

TABLE 1-continued

| Comp. # | CAS-nr.: | Formula | $M_w$ | Structure | Substituents | Ref. |
|---|---|---|---|---|---|---|
| 3 | NA | $C_{28}H_{28}N_4O_6S_8$ | 773.07 | 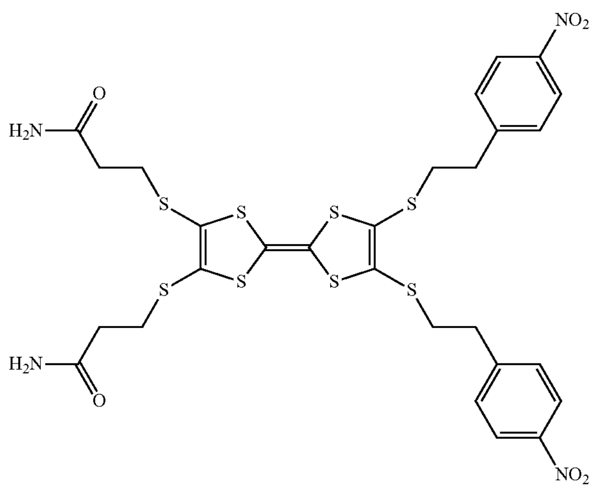 [SMILES: NC(=O)CCSC1=C(SCCC(N)=O)SC(=C2SC(SCCc3ccc([N+](=O)[O-])cc3)=C(SCCc3ccc([N+](=O)[O-])cc3)S2)S1] | $R^2 =$ $R^3 =$ Methoxycarbonyl — C(O)OMe<br><br>$R^4 =$ 2-Cyanoethylsulfanyl — S—CH2CH2—CN<br><br>$R^1 =$ $R^4 =$ 2-(Carboxamide)ethylsulfanyl — S—CH2CH2—C(O)NH2<br><br>$R^2 =$ $R^3 =$ 2-(4-Nitrophenyl)ethylsulfanyl | Ex |
| 4 | 26314-39-6 | $C_{14}H_{12}O_8S_8$ | 436.50 | 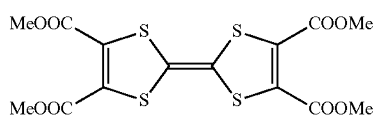 [SMILES: COC(=O)C1=C(C(=O)OC)SC(=C2SC(C(=O)OC)=C(C(=O)OC)S2)S1] | $R^1 =$ $R^2 =$ $R^3 =$ $R^4 =$ Methoxycarbonyl | [4] |
| 5 | 300766-19-2 | $C_{25}H_{31}NO_2S_7$ | 601.97 | 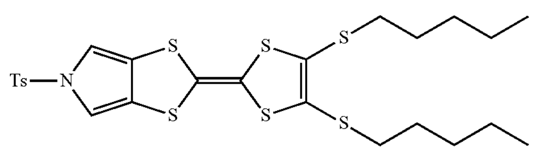 [SMILES: CCCCCSC1=C(SCCCCC)SC(=C2Sc3cn(S(=O)(=O)c4ccc(C)cc4)cc3S2)S1] | $R^1$ and $R^4$ together form: | [5] |

TABLE 1-continued

| Comp. # | CAS-nr.: | Formula | $M_w$ | Structure | | Substituents |
|---|---|---|---|---|---|---|
| 6 | NA | $C_{25}H_{35}NO_2S_7$ | 606.01 | [structure] | $R^2 =$ $R^3 =$ | Pentylsulfanyl |
| | | | | | $R^1$ and $R^4$ together form: | Ts—N [ring] |
| 7 | NA | $C_{19}H_{15}NO_6S_5$ | 516.65 | [structure] | $R^2 =$ $R^3 =$ | Methoxycarbonyl |
| | | | | | $R^1$ and $R^4$ together form: | Ts—N [ring] |
| 8 | NA | $C_{25}H_{31}N_3S_6$ | 565.92 | [structure] | $R^2 =$ $R^3 =$ | Pentylsulfanyl |
| | | | | | $R^1$ and $R^4$ together form: | [p-amidinophenyl-N ring] |
| 9 | NA | $C_{23}H_{35}NO_6S_6$ | 613.92 | [structure] | $R^2 =$ $R^3 =$ | [triethyleneglycol-dithio] |
| | | | | | $R^1$ and $R^4$ together form: | Me—N [ring] |

Ref.: Ex (all rows)

TABLE 1-continued

| Comp. # | CAS-nr.: | Formula | $M_w$ | Structure | Substituents | | Ref. |
|---|---|---|---|---|---|---|---|
| 10 | 132765-36-7 | $C_{18}H_{16}N_4S_8$ | 544.87 | 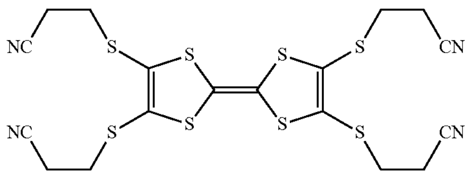 [SMILES: N#CCCSC1=C(SCCC#N)SC(=C2SC(SCCC#N)=C(SCCC#N)S2)S1] | $R^2 =$ $R^3 =$ | 2-(2-(2-Methoxyethoxy)-ethoxy)ethylsulfanyl | L |
| 11 | NA | $C_{14}H_{14}Br_2S_{12}$ | 566.52 | 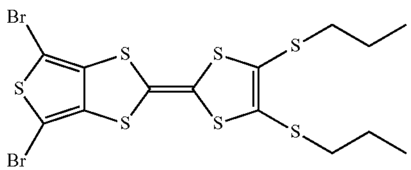 [SMILES: CCCSC1=C(SCCC)SC(=C2Sc3c(Br)sc(Br)c3S2)S1] | $R^1 =$ $R^2 =$ $R^3 =$ $R^4 =$ | 2-Cyanoethylsulfanyl | L |
| | | | | | $R^1$ and $R^4$ together form: | | |
| | | | | | $R^2 =$ $R^3 =$ | Propylsulfanyl | |
| 12 | 31366-25-3 | $C_6H_4S_4$ | 204.36 | 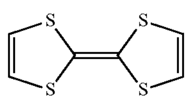 | $R^1 =$ $R^2 =$ $R^3 =$ $R^4 =$ | H | C |
| 13 | 55259-49-9 | $C_{10}H_{12}Se_4$ | 448.04 | 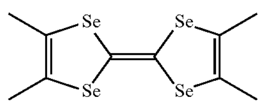 | $R^1 =$ $R^2 =$ $R^3 =$ $R^4 =$ | Methyl | C |

TABLE 1-continued
| Comp. # | CAS-nr.: | Formula | $M_w$ | Structure | Substituents | Ref. |
|---|---|---|---|---|---|---|
| 14 | NA | $C_{100}H_{148}N_4O_{24}S_{24}$ | 2559.82 | 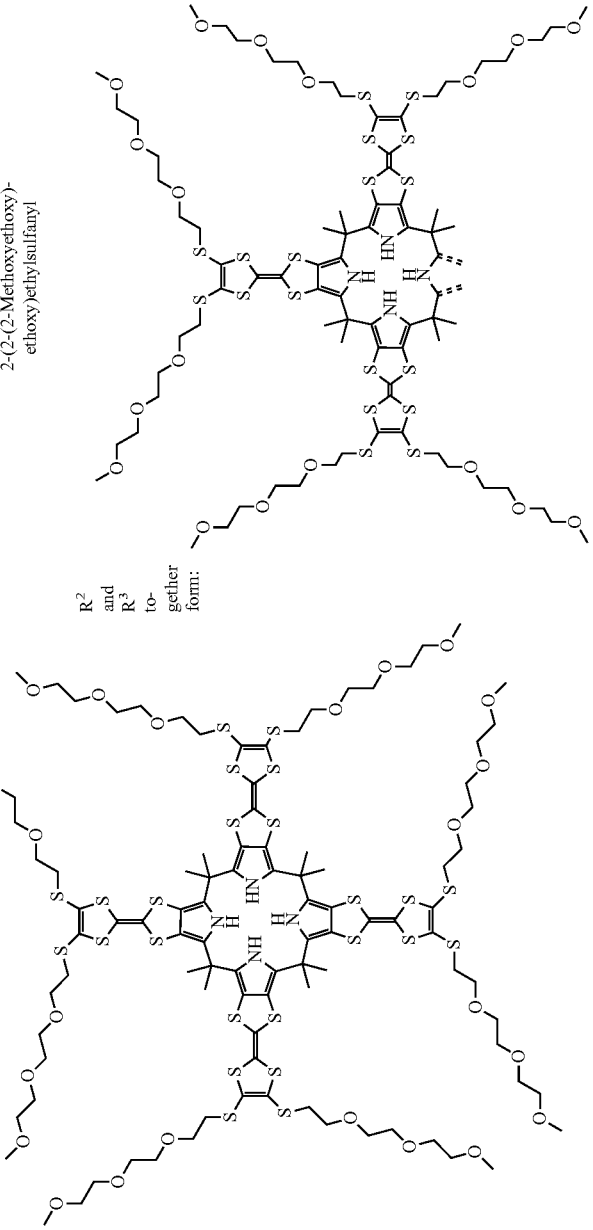 | $R^1 =$ $R^4 =$ 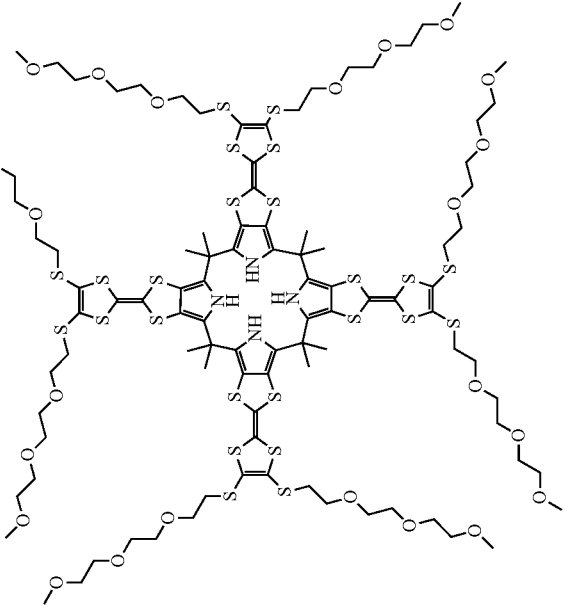 2-(2-(2-Methoxyethoxy)-ethoxy)ethylsulfanyl<br><br>$R^2$ and $R^3$ together form: | L |

TABLE 1-continued

| Comp. # | CAS-nr.: | Formula | $M_w$ | Structure | Substituents | | Ref. |
|---|---|---|---|---|---|---|---|
| 15 | NA | $C_{68}H_{84}N_4S_{24}$ | 1727.01 | (porphyrin-type macrocycle with PrS substituents) | $R^1 =$ $R^4 =$ | Propylsulfanyl | L |
| | | | | | $R^2$ and $R^3$ together form: | (dithiole-TTF fragment with SPr groups) | |
| 16 | 66946-48-3 | $C_{10}H_8S_8$ | 348.69 | (bis-dithiin-TTF structure) | $R^1$ and $R^4$ together form: | (ethylenedithio group) | C |
| | | | | | $R^2$ and $R^3$ together form: | (ethylenedithio group) | |
| 17 | 507008-37-7 | $C_{10}H_{12}S_4$ | 260.46 | (tetramethyl-TTF) | $R^1 =$ $R^2 =$ $R^3 =$ $R^4 =$ | Methyl | L |
| 18 | 24648-13-3 | $C_{14}H_8S_4$ | 304.47 | (dibenzo-TTF) | $R^1$ and $R^4$ together form: | (benzo group) | C |

TABLE 1-continued

| Comp. # | CAS-nr: | Formula | $M_w$ | Structure | Substituents | | Ref. |
|---|---|---|---|---|---|---|---|
| 19 | 120120-58-3 | $C_{10}H_8O_4S_4$ | 320.43 | 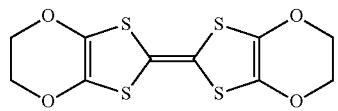 [SMILES: C1COC2=C(O1)SC(=C1SC3=C(OCCO3)S1)S2] | $R^2$ and $R^3$ together form: | | L |
| | | | | | $R^1$ and $R^4$ together form: | | L |
| 20 | 51501-77-0 | $C_{10}H_{12}S_8$ | 388.72 | 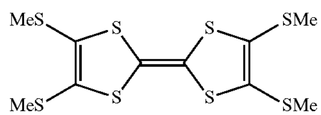 | $R^2$ and $R^3$ together form: | | L |
| | | | | | $R^1 = R^2 = R^3 = R^4 =$ Methylsulfanyl | | L |
| 21 | 26314-39-6 | $C_{14}H_{12}O_8S_4$ | 436.50 | See comp. #4 | See comp. #4 | | C |
| 22 | 35079-58-4 | $C_{14}H_{16}S_4$ | 312.54 | 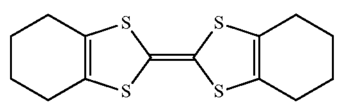 [SMILES: C1CCC2=C(C1)SC(=C1SC3=C(CCCC3)S1)S2] | $R^1$ and $R^4$ together form: | | L |
| | | | | | $R^2$ and $R^3$ together form: | | |
| 23 | 2786-70-1 | $C_{16}H_{14}N_2S_2$ | 298.43 | 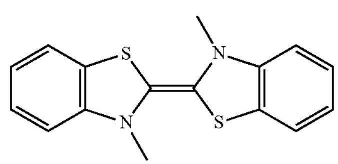 [SMILES: CN1/C(=C2\Sc3ccccc3N2C)Sc2ccccc21] | $R^1$ and $R^4$ together form: | | L |

TABLE 1-continued

| Comp. # | CAS-nr.: | Formula | $M_w$ | Structure | Substituents | Ref. |
|---|---|---|---|---|---|---|
| 24 | 66946-49-4 | $C_{12}H_{12}S_8$ | 412.74 | (structure) | $R^2$ and $R^3$ together form: (cyclohexadiene-like bridge) | L |
| 25 | 104515-79-9 | $C_{14}H_{20}S_8$ | 444.83 | (structure with SEt groups) | $R^1$ and $R^4$ together form: (─S─(CH$_2$)$_3$─S─ bridge); $R^2$ and $R^3$ together form: (─S─(CH$_2$)$_3$─S─ bridge) | L |
| 26 | 64394-47-4 | $C_8O_2S_8$ | 348.60 | (structure) | Ethylsulfanyl; $R^1$ and $R^4$ together form: (─S─C(=O)─S─); $R^2$ and $R^3$ together form: (─S─C(=O)─S─) | L |
| 27 | 105782-53-4 | $C_{78}H_{148}S_8$ | 1342.53 | (structure with SC$_{18}$H$_{37}$ groups) | Octadecylsylfanyl; $R^1$ = $R^2$ = $R^3$ = $R^4$ = | L |

TABLE 1-continued

| Comp. # | CAS-nr.: | Formula | $M_w$ | Structure | Substituents | | Ref. |
|---|---|---|---|---|---|---|---|
| 28 | 55052-32-9 | $C_{10}N_4S_4$ | 304.39 | [TTF with CN groups] | $R^1 = R^2 = R^3 = R^4 =$ | —C≡N Cyano | L |
| 29 | 106920-34-7 | $C_{70}H_{132}S_8$ | 1230.32 | [TTF with SC$_{16}$H$_{33}$ groups] | $R^1 = R^2 = R^3 = R^4 =$ | Hexadecylsulfanyl | L |
| 30 | 104515-77-7 | $C_{46}H_{84}S_8$ | 893.68 | [TTF with SC$_{10}$H$_{21}$ groups] | $R^1 = R^2 = R^3 = R^4 =$ | Decylsulfanyl | L |
| 31 | 59269-79-3 | $C_{10}H_4O_8S_4$ | 380.39 | [TTF with COOH groups] | $R^1 = R^2 = R^3 = R^4 =$ | COOH Carboxy | L |
| 32 | 71938-96-0 | $C_{22}H_{16}S_4$ | 408.62 | [fused naphthalene TTF structure] | $R^1$ and $R^4$ together form: $R^2$ and $R^3$ together form: | [benzene ring with two CH$_2$ linkers] [benzene ring with two CH$_2$ linkers] | C |
| 33 | 117860-14-7 | $C_{14}H_{14}N_2S_4$ | 338.53 | [pyrrole-fused TTF structure] | $R^1$ and $R^4$ together form: | [NH with two methyl-substituted vinyl groups] | L |

TABLE 1-continued

| Comp. # | CAS-nr.: | Formula | $M_w$ | Structure | | Substituents | Ref. |
|---|---|---|---|---|---|---|---|
| 34 | 106920-29-0 | $C_{26}H_{44}S_8$ | 613.15 | [structure with SC₅H₁₁ groups] | $R^2$ and $R^3$ together form: | [structure]<br>Pentylsulfanyl | L |
| 35 | 101751-48-8 | $C_{10}D_8S_8$ | 392.74 | [structure with D atoms] | $R^1 =$<br>$R^2 =$<br>$R^3 =$<br>$R^4 =$ | [D-substituted structure] | L |
| | | | | | $R^1$ and $R^4$ together form:<br>$R^2$ and $R^3$ together form: | [D-substituted structure] | L |
| 36 | 106928-77-2 | $C_{54}H_{100}S_8$ | 1005.89 | [structure with SC₁₂H₂₅ groups] | $R^1 =$<br>$R^2 =$<br>$R^3 =$<br>$R^4 =$ | [dodecyl chain]<br>Dodecylsulfanyl | L |
| 37 | 56851-13-9 | $C_{20}H_{16}S_4$ | 384.60 | [structure with phenyl and methyl groups] | $R^1 =$<br>$R^2 =$<br>$R^3 =$<br>$R^4 =$ | Phenyl<br><br>Methyl | C |

TABLE 1-continued

| Comp. # | CAS-nr.: | Formula | $M_w$ | Structure | Substituents | | Ref. |
|---|---|---|---|---|---|---|---|
| 38 | 88203-73-0 | $C_{34}H_{20}O_4S_8$ | 749.04 | (structure) | $R^1 = R^2 = R^3 = R^4 =$ | Benzoylsulfanyl | L |
| 39 | 329966-57-6 | $C_{14}H_{14}N_2S_6$ | 402.66 | (structure) | $R^1 = R^2 =$ <br> $R^3 = R^4 =$ | 2-Cyanoethylsulfanyl <br> Methyl | L |
| 40 | 128258-82-2 | $C_{14}H_{20}O_4S_8$ | 508.83 | (structure) | $R^1 = R^2 = R^3 = R^4 =$ | 2-hydroxyethylsulfanyl | L |
| 41 | 14130-66-5 | $C_{11}H_{10}N_2O_2S_4$ | 330.47 | (structure) | $R^1$ and $R^4$ together form: <br><br> $R^2 = R^3 =$ | (ring structure) <br><br> Methyl | L |

TABLE 1-continued

| Comp. # | CAS-nr.: | Formula | $M_w$ | Structure | Substituents | | Ref. |
|---|---|---|---|---|---|---|---|
| 42 | 128258-77-5 | $C_{14}H_{16}Cl_4S_8$ | 582.61 | (structure: TTF with four S-CH₂CH₂Cl groups) | $R^1 =$ $R^2 =$ $R^3 =$ $R^4 =$ | (2-chloroethylsulfanyl group: —S—CH₂CH₂—Cl) 2-Chloroethylsulfanyl | L |
| 43 | 61940-34-9 | $C_{16}H_{20}S_4$ | 340.59 | (structure: bis(cycloheptano-fused) dithiole dimer) | $R^1$ and $R^4$ together form: $R^2$ and $R^3$ together form: | (cycloheptane ring) (cycloheptane ring) | C |
| 44 | 420447-12-1 | $C_{15}H_{11}NS_3$ | 301.45 | (structure: benzo-fused dithiole with N-methyl benzothiazole) | $R^1$ and $R^4$ together form: $R^2$ and $R^3$ together form: | (benzene ring) (benzene ring) | L |
| 45 | 149130-70-1 | $C_{12}H_{12}N_2O_2S_4$ | 344.5 | (structure: dimethyl-dithiole fused with N,N′-dimethyl dioxo pyrimidine) | $R^1$ and $R^4$ together form: $R^2 =$ $R^3 =$ | (—N(Me)—C(O)—N(Me)—C(O)— bridge) Methyl | L |

TABLE 1-continued

| Comp. # | CAS-nr.: | Formula | $M_w$ | Structure | Substituents | | Ref. |
|---|---|---|---|---|---|---|---|
| 46 | 129137-82-2 | $C_{22}H_{24}S_{12}$ | 673.21 | [structure: bis-benzodithiole with SMe groups] | $R^1$ and $R^4$ together form: / $R^2$ and $R^3$ together form: | [SMe-substituted diene fragments] | L |
| 47 | 100760-57-4 | $C_{20}H_{16}S_4$ | 384.60 | [tetrathiafulvalene with two phenyl and two methyl substituents] | $R^1 = R^3 =$ / $R^2 = R^4 =$ | Phenyl / Methyl | C |
| 48 | 75258-46-7 | $C_{22}H_{20}O_2S_4$ | 444.56 | [tetrathiafulvalene with two p-methoxyphenyl and two methyl substituents] | $R^1 = R^2 =$ / $R^3 = R^4 =$ | p-Methoxyphenyl / Methyl | C |

TABLE 1-continued

| Comp. # | CAS-nr.: | Formula | $M_w$ | Structure | Substituents | Ref. |
|---|---|---|---|---|---|---|
| 49 | 162190-39-8 | $C_{20}H_{24}O_2S_8$ | 552.92 | (structure) | $R^1$ and $R^4$ together form: (Et-CH-S-C(=O)-CH-Et-S-); $R^2$ and $R^3$ together form: (Et-CH-S-C(=O)-CH-Et-S-) | L |
| 50 | 75949-42-7 | $C_{18}H_{28}S_{12}$ | 629.19 | (structure) | $R^1 =$ $R^2 =$ $R^3 =$ $R^4 =$ 2-(Methylthio)ethylsulfanyl | L |
| 51 | 21583-22-2 | $C_{16}H_{14}N_2S_2$ | 298.43 | (structure) | $R^1$ and $R^4$ together form: (phenyl); $R^2$ and $R^3$ together form: (phenyl) | L |
| 52 | 698359-01-2 | $C_{24}H_{24}S_6$ | 504.84 | (structure) | $R^1 =$ $R^2 =$ Benzyl; $R^3 =$ $R^4 =$ Ethyl | L |

TABLE 1-continued

| Comp. # | CAS-nr.: | Formula | $M_w$ | Structure | Substituents | | Ref. |
|---|---|---|---|---|---|---|---|
| 53 | 169824-85-5 | $C_{12}H_6N_6S_2$ | 298.35 | 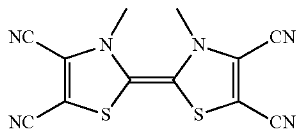 [SMILES: CN1C(C#N)=C(C#N)S/C1=C1\SC(C#N)=C(C#N)N1C] | $R^1 =$ $R^2 =$ $R^3 =$ $R^4 =$ | —C≡N Cyano | L |
| 54 | 134665-59-1 | $C_{18}H_{28}BrCuS_{12}$ | 772.64 | 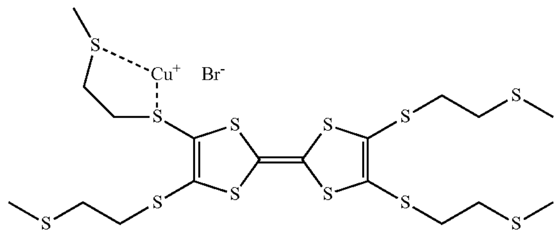 | $R^1 =$ $R^2 =$ $R^3 =$ $R^4 =$ | 2-(Methylthio)ethylsulfanyl copper bromide / Br⁻ / SMe / 2-(Methylthio)ethylsulfanyl | L |
| 55 | 128258-81-1 | $C_{42}H_{36}O_8S_8$ | 925.25 | 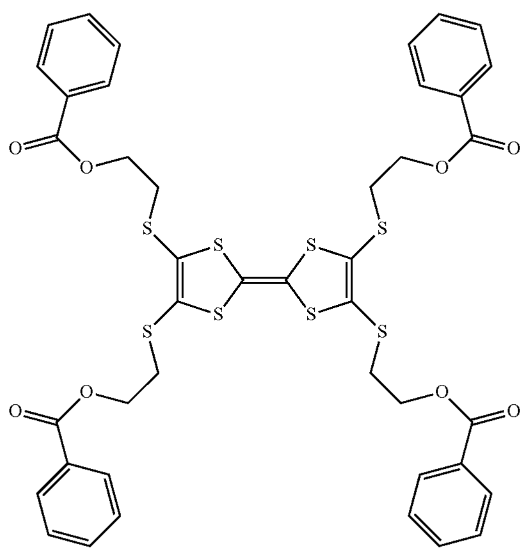 [SMILES: O=C(OCCSC1=C(SCCOC(=O)c2ccccc2)SC(=C2SC(SCCOC(=O)c3ccccc3)=C(SCCOC(=O)c3ccccc3)S2)S1)c1ccccc1] | $R^1 =$ $R^2 =$ $R^3 =$ $R^4 =$ | 2-(Phenylcarboxy)-ethylsulfanyl | L |

TABLE 1-continued

| Comp. # | CAS-nr.: | Formula | $M_w$ | Structure | | Substituents | Ref. |
|---|---|---|---|---|---|---|---|
| 56 | 128258-78-6 | $C_{14}H_{16}Br_4S_8$ | 760.41 | (structure) | $R^1 =$ $R^2 =$ $R^3 =$ $R^4 =$ | 2-Bromoethylsulfanyl | L |
| 57 | 1000760-61-0 | $C_{22}H_{16}S_4$ | 408.62 | (structure) | $R^1$ and $R^4$ together form: $R^2$ and $R^3$ together form: | (o-phenylene-diethyl) (o-phenylene-diethyl) | C |
| 58 | 100760-59-6 | $C_{20}H_{14}Br_2S_4$ | 542.39 | (structure) | $R^1 =$ $R^3 =$ $R^2 =$ $R^4 =$ | p-Bromophenyl Methyl | L |

TABLE 1-continued

| Comp. # | CAS-nr.: | Formula | $M_w$ | Structure | Substituents | Ref. |
|---|---|---|---|---|---|---|
| 59 | 100760-58-5 | $C_{20}H_{14}Cl_2S_4$ | 453.49 | (structure) | $R^1 =$ $R^3 =$ p-Chlorophenyl; $R^2 =$ $R^4 =$ Methyl | C |
| 60 | 83362-96-3 | $C_{20}H_{14}Cl_2S_4$ | 453.49 | (structure) | $R^1 =$ $R^2 =$ p-Chlorophenyl; $R^3 =$ $R^4 =$ Methyl | C |
| 61 | 67855-75-8 | C16H12S4 | 332.53 | (structure) | $R^1$ and $R^4$ together form: (methylbenzo); $R^2$ and $R^3$ together form: (methylbenzo) | L |

TABLE 1-continued

| Comp. # | CAS-nr.: | Formula | $M_w$ | Structure | Substituents | | Ref. |
|---|---|---|---|---|---|---|---|
| 62 | 1030768-99-0 | $C_{42}H_{32}Cl_4N_4$ | 734.54 | (structure: tetrakis(4-chlorobenzyl)-bis-benzimidazolylidene) | $R^1$ and $R^4$ together form: | (phenyl ring) | C |
| | | | | | $R^2$ and $R^3$ together form: | (phenyl ring) | |
| 63 | 883534-04-1 | $C_{24}H_{24}S_6$ | 504.84 | (structure: tetrathiafulvalene with Et, Et, benzyl, benzyl) | $R^1 = R^4 =$ | Benzyl | C |
| | | | | | $R^2 = R^3 =$ | Ethyl | |
| 64 | 551930-23-5 | $C_{14}H_{20}O_2S_6$ | 412.70 | (structure: tetrathiafulvalene with Et, Et, S-CH2CH2OH, S-CH2CH2OH) | $R^1 = R^4 =$ | 2-hydroxyethylsulfanyl (—S—CH2CH2OH) | C |
| | | | | | $R^2 = R^3 =$ | Ethyl | |

TABLE 1-continued

| Comp. # | CAS-nr.: | Formula | $M_w$ | Structure | | Substituents | Ref. |
|---|---|---|---|---|---|---|---|
| 65 | 329908-90-9 | $C_{14}H_{24}N_4S_8$ | 504.89 | [TTF core with four 2-aminoethylsulfanyl substituents] | $R^1 =$<br>$R^2 =$<br>$R^3 =$<br>$R^4 =$ | [–S–CH₂CH₂–NH₂]<br>2-Aminoethylsulfanyl | C |
| 66 | 325721-85-5 | $C_{42}H_{36}O_8S_8$ | 925.25 | [TTF core with four 2-(phenoxycarbonyl)ethylsulfanyl substituents] | $R^1 =$<br>$R^2 =$<br>$R^3 =$<br>$R^4 =$ | [–S–CH₂CH₂–C(=O)–O–Ph]<br>2-(Phenoxycarbonyl)-ethylsulfanyl | C |
| 67 | 304692-67-9 | $C_{42}H_{40}N_4O_4S_8$ | 921.31 | [TTF core with four 2-(N-benzoyl)aminoethylsulfanyl substituents] | $R^1 =$<br>$R^2 =$<br>$R^3 =$<br>$R^4 =$ | [–S–CH₂CH₂–NH–C(=O)–Ph]<br>2-(N-Benzoyl)amino-ethylsulfanyl | C |

TABLE 1-continued

| Comp. # | CAS-nr.: | Formula | $M_w$ | Structure | Substituents | | Ref. |
|---|---|---|---|---|---|---|---|
| 68 | 149130-58-5 | $C_{10}H_7N_2O_2S_4^-$ | 315.44 | 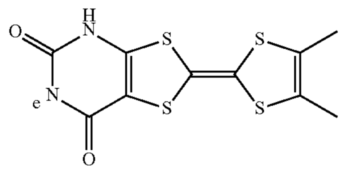 [SMILES: CC1=C(C)SC(=C2Sc3[nH]c(=O)[nH]c(=O)c3S2)S1] | $R^1$ and $R^4$ together form: | (cyclic urea fragment); $R^2 = R^3 =$ Methyl | C |
| 69 | 149130-54-1 | $C_{10}H_2N_4O_4S_4^{2-}$ | 370.41 | 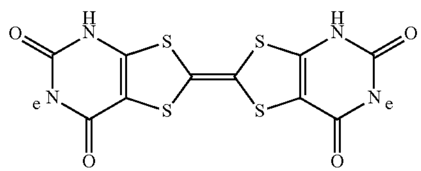 [SMILES: O=c1[nH]c2c(c(=O)[nH]1)S/C(=C1/Sc3[nH]c(=O)[nH]c(=O)c3S1)S2] | $R^1$ and $R^4$ together form: | (cyclic urea fragment); $R^2$ and $R^3$ together form: (cyclic urea fragment) | C |
| 70 | 125113-45-3 | $C_6F_4S_4$ | 276.32 | 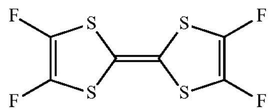 [SMILES: FC1=C(F)SC(=C2SC(F)=C(F)S2)S1] | $R^1 = R^2 = R^3 = R^4 =$ Fluoro | | T |
| 71 | 121910-92-7 | $C_6Cl_4S_4$ | 342.14 | 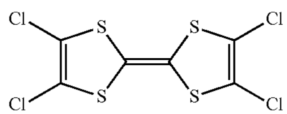 | $R^1 = R^2 = R^3 = R^4 =$ Chloro | | L |

TABLE 1-continued

| Comp. # | CAS-nr. | Formula | $M_w$ | Structure | Substituents | | Ref. |
|---|---|---|---|---|---|---|---|
| 72 | 99159-47-4 | $C_6Br_4S_4$ | 519.94 | 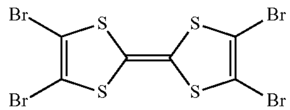 | $R^1 =$<br>$R^2 =$<br>$R^3 =$<br>$R^4 =$ | Bromo | L |
| 73 | 125113-44-2 | $C_6I_4S_4$ | 707.94 | 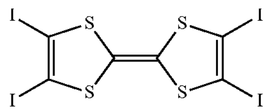 [SMILES: IC1=C(I)SC(=C2SC(I)=C(I)S2)S1] | $R^1 =$<br>$R^2 =$<br>$R^3 =$<br>$R^4 =$ | Iodo | L |
| 74 | 196822-89-6 | $C_6Cl_4O_4$ | 277.87 | 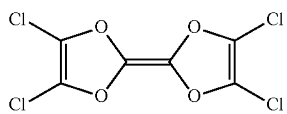 [SMILES: ClC1=C(Cl)OC(=C2OC(Cl)=C(Cl)O2)O1] | $R^1 =$<br>$R^2 =$<br>$R^3 =$<br>$R^4 =$ | Chloro | T |
| 75 | 196822-87-4 | $C_6Cl_4Se_4$ | 529.72 | 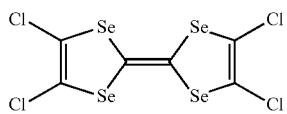 [SMILES: ClC1=C(Cl)[Se]C(=C2[Se]C(Cl)=C(Cl)[Se]2)[Se]1] | $R^1 =$<br>$R^2 =$<br>$R^3 =$<br>$R^4 =$ | Chloro | L |
| 76 | 196822-88-5 | $C_6Cl_4Te_4$ | 724.28 | 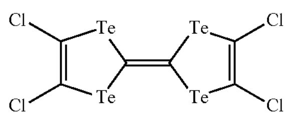 | $R^1 =$<br>$R^2 =$<br>$R^3 =$<br>$R^4 =$ | Chloro | T |
| 77 | 351533-94-3 | $C_6Br_4Se_4$ | 707.52 | 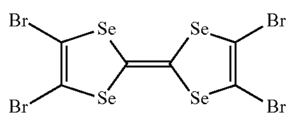 [SMILES: BrC1=C(Br)[Se]C(=C2[Se]C(Br)=C(Br)[Se]2)[Se]1] | $R^1 =$<br>$R^2 =$<br>$R^3 =$<br>$R^4 =$ | Bromo | L |
| 78 | 351533-95-4 | $C_6I_4Se_4$ | 895.52 | 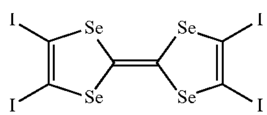 [SMILES: IC1=C(I)[Se]C(=C2[Se]C(I)=C(I)[Se]2)[Se]1] | $R^1 =$<br>$R^2 =$<br>$R^3 =$<br>$R^4 =$ | Iodo | L |

C: commercially available,
T: theoretical compound,
Ex: see experimental section,
L: literature In another aspect according to the present invention the compounds of the general formulas I) and 1) and 2) has a molecular weight below 1700, preferably below 1600 and more preferably below 1500. In still other aspects of the invention the molecular weight of the compounds can be low and even below 1000.

In still another aspect according to the present invention the compounds are selected from general formula 1), wherein the hetero atoms $X^1$ to $X^4$ are selected from sulphur or selenium; and $R^1$ is a substituent selected from hydrogen; $C_1$-$C_4$-alkyl; methoxycarbonyl; 2-substituted ethylsulfanyl wherein the substituents are selected from the group of carboxamide and cyano; and (4'-{[7-(2-Cyanoethylthio)-2,3-Dimethoxy-carbonyl-6-thio-methylene]tetrathiafulvalene}-4-bipyridine)methylsulfanyl;

$R^2$ is a substituent selected from hydrogen; $C_1$-$C_4$-alkyl; methoxycarbonyl; $C_1$-$C_{20}$-alkylsulfanyl; 2-substituted ethylsulfanyl wherein the substituents are selected from the group of 4-nitrophenyl and cyano;

$R^3$ is a substituent selected from hydrogen; $C_1$-$C_4$-alkyl; methoxycarbonyl; $C_1$-$C_{20}$-alkylsulfanyl such as pentylsulfanyl; and 2-substituted ethylsulfanyl wherein the substituents are selected from the group of 4-nitrophenyl and cyano; and $R^4$ is a substituent selected from hydrogen; $C_1$-$C_4$-alkyl; methoxycarbonyl; 2-substituted ethylsulfanyl wherein the substituents are selected from the group of carboxamide and cyano; or $R^1$ and $R^4$ together form:

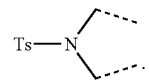

In still another aspect according to the present invention the compounds are selected from general formula 2), wherein the hetero atoms $X^1$ to $X^4$ are sulphur; and $R^1$ is a substituent selected from 2-(2-(2-methoxyethoxy)ethoxy); $C_1$-$C_{20}$-alkylsulfanyl such as for example ethylsulfanyl and propylsulfanyl;

$R^2$ is a substituent selected from methoxycarbonyl; $C_1$-$C_{20}$-alkylsulfanyl such as for example propylsulfanyl, pentylsulfanyl; 2-substituted ethylsulfanyl wherein the substituents are selected from the group of 4-nitrophenyl and 2-(2-methoxyethoxy)ethoxy;

$R^3$ is a substituent selected from methoxycarbonyl; $C_1$-$C_{20}$-alkylsulfanyl such as for example propylsulfanyl and pentylsulfanyl; 2-substituted ethylsulfanyl wherein the substituents are selected from the group of 4-nitrophenyl and 2-(2-methoxyethoxy)ethoxy;

$R^4$ is a substituent selected from $C_1$-$C_{20}$-alkylsulfanyl such as for example propylsulfanyl; 2-(2-(2-methoxyethoxy)ethoxy)ethylsulfanyl; or $R^1$ and $R^4$ together form

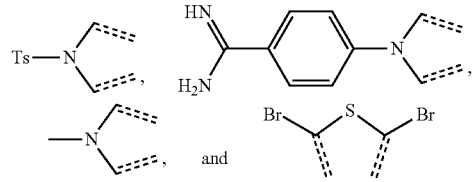

$R^2$ and $R^3$ together form

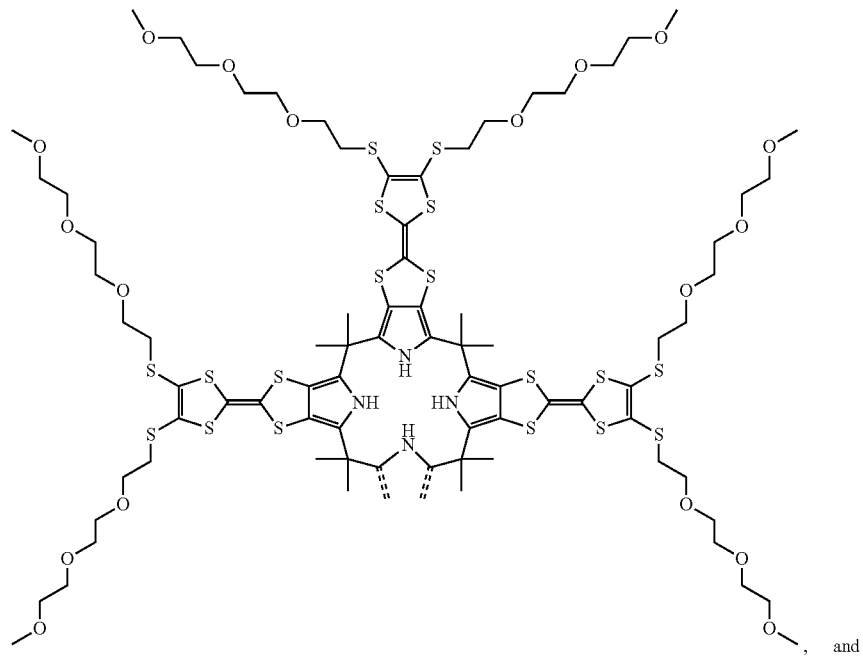

, and

-continued

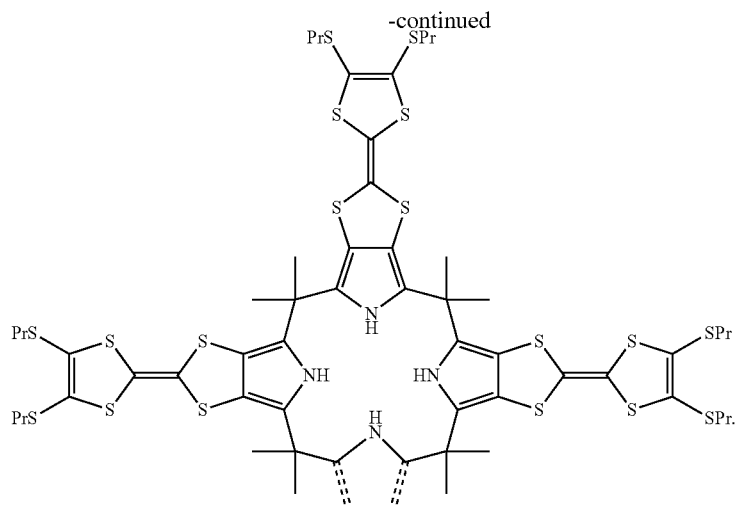

As evident from the above the at least two chemo-selective compounds can be selected from the compounds having general formula I), 1) and 2), or most preferred from a mixture thereof.

In one aspect according to the present invention one of the at least two compounds is compound 1 of Table 1.

In another aspect according to the present invention one of the at least two compounds is compound 2 of Table 1.

In another aspect according to the present invention one of the at least two compounds is compound 3 of Table 1.

In another aspect according to the present invention one of the at least two compounds is compound 4 of Table 1.

In another aspect according to the present invention one of the at least two compounds is compound 5 of Table 1.

In another aspect according to the present invention one of the at least two compounds is compound 6 of Table 1.

In another aspect according to the present invention one of the at least two compounds is compound 7 of Table 1.

In another aspect according to the present invention one of the at least two compounds is compound 8 of Table 1.

In another aspect according to the present invention one of the at least two compounds is compound 9 of Table 1.

In another aspect according to the present invention one of the at least two compounds is compound 10 of Table 1.

In another aspect according to the present invention one of the at least two compounds is compound 11 of Table 1.

In another aspect according to the present invention one of the at least two compounds is compound 12 of Table 1.

In another aspect according to the present invention one of the at least two compounds is compound 13 of Table 1.

In another aspect according to the present invention one of the at least two compounds is compound 14 of Table 1.

In another aspect according to the present invention one of the at least two compounds is compound 15 of Table 1.

In another aspect according to the present invention the sensor array comprises at least two different compounds selected from compounds 1 to 15 of Table 1.

In another aspect according to the present invention the sensor array comprises all of the compounds 1 to 15 of Table 1. In another aspect the sensor array comprises all of the compounds 1 to 13 as well as at least two compounds selected from compounds 16 to 78 of table 1.

The sensor array according to the present invention with a plurality of chemo-selective compounds is by way of example suitable for detection of illegal drugs. Large amount of drug precursors smuggled around the world through various ways: aircrafts, by freight vehicles and container transport. This sensor can thus help to easily detect a variety of illegal chemicals and drugs, and drug precursors carried by individuals as well as hidden in mails, luggage and conveyance.

The sensor array according to the present invention can also be used to define the presence of bacteria on the surface of food samples. Food, such as meat and fish, are in fact excellent mediums for microbial growth due to high water content, the water soluble carbohydrates and non-protein nitrogen, favourable pH, and high levels of oxygen. The food manufacturing industry requires fast information regarding quality of raw material and commodities. In general, microbial food spoilage is a relatively saddening event, but if it has occurred then results of microbial activity can reveal themselves in different ways: products and by-products of microbial metabolism, pigments, gases, polysaccharides, flavours, and odours. The sensor array can in this contest provide rapid information about the presence of metabolically active microorganisms on the surface of food samples. Therefore, this sensor can be used as a simple and rapid tool since it is easy to use and can be provided at a low cost. Measurements using the sensor array according to the invention can be performed within 2 min or less. The sensor array of the present invention were applied to detect presence of bacteria in minced meat and fish samples as shown in the Example section. The working principle was based on the detection and identification of gases emanating by bacteria during their metabolism.

The sensor array according to the present invention can also be used for screening of most commonly used explosives and organic compounds in the real-time format in liquid phase. The main characteristics for the sensor array are based on such parameters as detection limit, time of the response and high selectivity. Those characteristics are very important and essential in order to prevent terroristic attacks, distribution of narcotics, illegal drugs or in the environmental control. The sensor survey can also be performed in liquid phase, for example in water or in organic polar solvents, and this can enhance the detection properties of the sensor array. The liquid phase is a good environment for screening of analytes in various concentrations. The signal of relevant changes in the sensor array can often be obtained faster in liquid phase than in gas phase.

Thus, a second object of the present invention relates to use of at least two different chemo-selective compounds represented by the general formula I), wherein $X^1$, $X^2$, $X^3$, and $X^4$ each independently represents a hetero atom selected from nitrogen being NH or substituted nitrogen, oxygen, sulfur, selenium, and tellurium; and $R^1$, $R^2$, $R^3$, and $R^4$ each independently represents hydrogen, halogen, or an organic or metal organic group; and the dashed bonds represent independently of each other either a single bond or a double bond; in a sensor array for detection of analytes and mixtures thereof in gas or liquid phase.

In one aspect the present invention provides use of at least two different chemo-selective compounds represented by the general formulas 1) and 2), wherein $X^1$, $X^2$, $X^3$, and $X^4$ each independently represents a hetero atom selected from nitrogen being NH or nitrogen substituted by $C_1$-$C_4$-alkyl or chlorophenylmethyl, oxygen, sulfur, selenium, and tellurium; and R', $R^2$, $R^3$, and $R^4$ each independently represents hydrogen, halogen, or an organic or metal organic group; in a sensor array for detection of analytes and mixtures thereof in gas or liquid phase.

In one aspect of the present invention the hetero atoms $X^1$, $X^2$, $X^3$, and $X^4$ each independently may be selected as indicated above.

In another aspect of the present invention the substituents $R^1$, $R^2$, $R^3$, and $R^4$ each independently may be selected as indicated above.

In another aspect of the present invention different combinations of the hetero atoms $X^1$-$X^4$ and substituents $R^1$-$R^4$ may be selected as indicated above.

In one aspect of the second object of the present invention the at least two different compounds are selected from compounds no. 1 to 15 of Table 1. In another aspect of the invention the compounds are selected from compounds no. 1 to 13 as well as at least two compounds selected from compounds no. 16 to 78 of table 1.

A third object of the present invention relates to a method for preparation of the sensor array according to the present invention, wherein at least two different chemo-selective compounds having the general formula I) are immobilized on a solid support. In another aspect the present invention relates to a method for preparation of the sensor array according to the present invention, wherein at least two different chemo-selective compounds having the general formulas 1) or 2) are immobilizing on a solid support. These at least two different chemo selective compounds are immobilized spatially separated and individually addressable.

It should be mentioned that the same methods can be used for preparation of the sensor arrays for both gasses and liquids and also that the same solid supports are applicable.

The solid support of the sensor array can be Si-based, such as poly- and mono-crystalline silicon, silicon dioxide, silicon nitride, silica, glass, controlled pore glass, silica gel, metallic such as gold, platinum, silver, titanium, vanadium, chromium, iron cobalt, nickel, copper, palladium, aluminum, gallium, germanium, indium, zinc, alloys like cadmium telluride and copper-indium-selenide, and metallic oxides, synthetic or natural polymers such as polystyrene, polyethylene, polypropylene, polyvinylacetate, polyvinylchloride polyvinylpyrrolidone, polyvinyldifluoride, polyacrylonitrile, polymethyl methacrylate, polytetrafluoro ethylene, polycarbonate, polyester, polyimide, cellulose, nitrocellulose, starch, polysaccharides, natural rubber, butyl rubber, styrene butadiene rubber, silicone rubber, epoxies like SU-8, polycyclic olefins' like Topas, photoresist materials, and conducting polymers like poly(3,4-ethylenedioxythiophene) (PEDOT), polyacetylene, polythiophene, polypyrrole, and polyaniline, carbon based such as glassy carbon, carbon paste, graphite, carbon nanotubes, and graphene. Preferred solid supports are silica gel, silicon dioxide, silicon nitride, gold, platinum, polyimide, nitrocellulose, polyvinyldifluoride, polyester, polypropylene, nylon, polytetrafluoro ethylene, polyamide, glassy carbon, carbon paste, graphite, corbon nanotubes, and graphene.

In yet another aspect of the present invention the at least two different chemo-selective compounds are immobilized on a solid support and their locations in the array are as illustrated in FIG. 1.

In another embodiment of the present invention compounds 1 to 13 of Table 1 are immobilized on a solid support together with two other compounds selected from Table 1.

In gas phase, the array of chemo-selective compounds can be exposed to saturated vapours of analytes (e.g., acetone, acetic acid, DNT, formic acid, hydrochloric acid, methanol, ethanol, propanol, and toluene as described in example 4). Alternatively vapours can be passed over the array using a flow cell and a pump. Low concentrations of less volatile compounds like explosives can be detected using a sample pre-concentrator followed by heating of the sample bringing the vapours to the array.

In liquid phase, the array of chemo selective compounds can be immersed into the liquid, or liquid can be passed over the array using a fluidic system. For use in liquid phase special attention in the selection of chemo-selective compound will be to avoid bleeding of the compounds in contact with the liquid.

Thus, in a fourth object the present invention relates to use of the sensor array according to the present invention for detection and/or identification of an analyte or mixtures thereof in gas or liquid phase. Therefore, if no bleeding occurs in the liquid phase, the same sensor array can be used in both liquid and gas phase.

In a further aspect the present invention relates to use of the sensor array according to the present invention for detection and/or identification of an analyte or mixtures thereof such as a volatile organic compound or mixtures thereof in gas phase.

In one aspect the present invention relates to use of the sensor array according to the present invention for detection and/or identification of a volatile organic compound or mixtures thereof in gas phase. The gas phase may be ambient air or may be an inert carrier gas like nitrogen or argon. The array can also be useful in detection of and identification of volatile organic compounds in the presence of water vapor in air.

In another aspect of the present invention the analyte or mixtures thereof are amines, alcohols, carboxylic acids, ketones, sulphides, thiols, explosives, toxic compounds, toxins, drugs and drug precursors, narcotics, environmental poisons and pollutants, exhaust gasses from burning of fuels (NOx and SOx).

In another aspect of the present invention the volatile organic compound or mixtures thereof are amines, alcohols, carboxylic acids, aldehydes, ketones, sulfides, thiols, explosives, toxic compounds, toxins, drugs, narcotics, environmental poison and pollutants.

In another aspect of the present invention the sensor array can be used for screening of spoilage and/or freshness of food based on the detection and identification of gases emanating by bacteria during their metabolism.

In another aspect of the present invention the sensor array can be used for screening of vapour poisoning compounds in plastic materials and furniture in the gas phase.

For each application the chemo-selective compounds of the sensor array will be selected to address operational constraints for example environmental changes such as temperature, humidity and other interferants giving rise to false positives and false negatives. Each array can be optimized according to the complexity of the particular application.

In a fifth object the present invention relates to a method of detecting and identifying an analyte or mixtures thereof in a gas or liquid, comprising:
  obtaining a first measurement of the sensor array according to the present invention before exposure to (in absence of) the analyte(s),
  exposing the sensor array to the analyte(s) in gas or liquid phase,
  obtaining a second measurement of the sensor array after exposure to the analyte(s), and
  analyzing a difference between the first measurement and the second measurement.

In one aspect the present invention relates to a method of detecting and identifying a volatile organic compound or mixtures thereof in a gas, comprising:
  obtaining a first measurement of the sensor array according to the present invention before exposure to (in absence of) the analyte(s),
  exposing the sensor array to the analyte(s) in gas phase,
  obtaining a second measurement of the sensor array after exposure to the analyte(s), and
  analyzing a difference between the first measurement and the second measurement.

In one aspect the first and second measurements are performed by electrochemical measurements, photonic measurements, conductivity measurements, colorimetric measurements, etc., or by an array of different measurements. The changes of physicochemical properties of the chemo-selective compounds of the array can be detected by a transducer or an array of transducers. For example, changes in colour can be detected either by transmission measurements or by reflection measurement using e.g. standard ccd cameras or flatbed scanner. Other transduction methods can measure the change in mass e.g. using cantilever arrays by change in resonance frequency, or acoustic wave devices, change in surface stress using cantilevers, change of surface potential using MOSFET arrays, change in conductivity e.g. using conductive polymer arrays or graphene. The individual change of each chemo-selective compound in the array is then analyzed by pattern recognition methods to analyze, identify or classify the analyte or analyte mixture.

In another aspect according to the present invention analyzing a difference between the first and second measurements gives a fingerprint of the analyte(s) in the gas or liquid phase. The initial measurement will record the environmental background of interfering substances while the second measurement records the change caused by the presence of the analyte or analytes plus the background. Calculating the difference map between the two measurements will give the fingerprint of the analyte or analytes alone. When using a colorimetric technique as the transduction method, each compound in the array changes color. A change in a color signature indicates the presence of known or unknown analytes. Each chosen dye reacts chemo-selectively with the analytes of interest. Digital imaging of the dye array before and after exposure to the analytes creates a color difference map which composes a unique fingerprint for each analyte. In order to extract the color code from each dye the position of each dye on the image must be located. Each dye is represented using the red, green, and blue color scheme. In this model every color is provided as red, green, and blue color (RGB); RGB values are given in the 0-255 integer range. The minimum intensity of the color gives black (0;0;0) and maximum white color (255;255;255). After the dye has been located and converted to RGB values, the median value of each dye is calculated. The median instead of the mean is used in order to be more robust to noise and outliers.

In a sixth object of the invention relates to a method for detecting and identifying an analyte or mixtures thereof in a gas or liquid, comprising:
  obtaining a first image of the sensor array according to the present invention before exposure to (in absence of) the analyte(s),
  exposing the sensor array to the analyte(s) in gas or liquid phase,
  obtaining a second image of the sensor array after exposure to the analyte(s), and
  analyzing a difference between the first image and the second image by creating color difference map.

Another aspect of the invention relates to a method for detecting and identifying a volatile organic compound or mixtures thereof in a gas, comprising:
  obtaining a first image of the sensor array according to the present invention before exposure to (in absence of) the analyte(s),
  exposing the sensor array to the analyte(s) in gas phase,
  obtaining a second image of the sensor array after exposure to the analyte(s), and
  analyzing a difference between the first image and the second image by creating color difference map.

In another aspect of the present invention the analyte(s) are identified within 30-120 sec after exposure to the gas or liquid phase. In another aspect of the invention, the analyte(s) are identified in less than 30 sec. It is contemplated that the sensor sensitivity will be increased, by screening analytes in various concentrations and calculating the kinetics of relevant reactions.

In another embodiment of the present invention the analyte(s) are identified after several weeks of exposure to the gas or liquid phase.

It should be noted that embodiments and features described in the context of one of the aspects of the present invention also apply to the other aspects of the invention.

All patent and non-patent references cited in the present application, are hereby incorporated by reference in their entirety. The invention will now be described in further details in the following non-limiting examples and figure.

EXAMPLES

Synthetic Procedures

Synthesis of 2-(4,5-Bis[2-{2-(2-methoxyethoxy)ethoxy}ethylthio]-1,3-dithiole-2-ylidene)-5-methyl-1,3-dithiolo[4,5-c]pyrrole (compound 9)

Step A 2-(4,5-Bis[2-{2-(2-methoxyethoxy)ethoxy}ethylthio]-1,3-dithiole-2-ylidene)-5-tosyl-1,3-dithiolo[4,5-c]pyrrole (C)

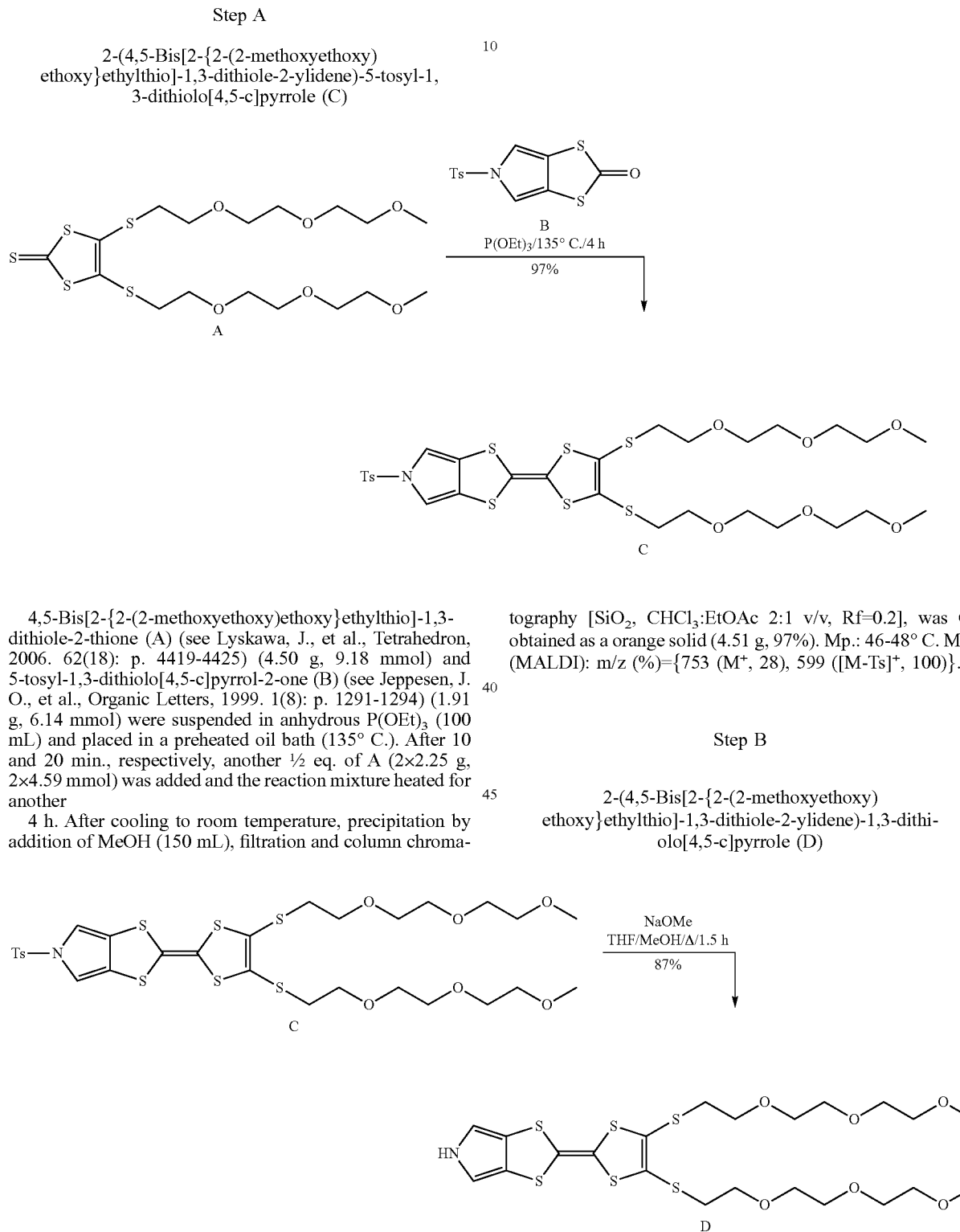

4,5-Bis[2-{2-(2-methoxyethoxy)ethoxy}ethylthio]-1,3-dithiole-2-thione (A) (see Lyskawa, J., et al., Tetrahedron, 2006. 62(18): p. 4419-4425) (4.50 g, 9.18 mmol) and 5-tosyl-1,3-dithiolo[4,5-c]pyrrol-2-one (B) (see Jeppesen, J. O., et al., Organic Letters, 1999. 1(8): p. 1291-1294) (1.91 g, 6.14 mmol) were suspended in anhydrous P(OEt)$_3$ (100 mL) and placed in a preheated oil bath (135° C.). After 10 and 20 min., respectively, another ½ eq. of A (2×2.25 g, 2×4.59 mmol) was added and the reaction mixture heated for another 4 h. After cooling to room temperature, precipitation by addition of MeOH (150 mL), filtration and column chromatography [SiO$_2$, CHCl$_3$:EtOAc 2:1 v/v, Rf=0.2], was C obtained as a orange solid (4.51 g, 97%). Mp.: 46-48° C. MS (MALDI): m/z (%)={753 (M$^+$, 28), 599 ([M-Ts]$^+$, 100)}.

Step B 2-(4,5-Bis[2-{2-(2-methoxyethoxy)ethoxy}ethylthio]-1,3-dithiole-2-ylidene)-1,3-dithiolo[4,5-c]pyrrole (D)

Compound C (4.48 g, 5.94 mmol) was dissolved in anhydrous THF (200 mL) and anhydrous MeOH (70 mL), and degassed with $N_2$ for 20 min. To this solution was NaOMe i MeOH (25%, 3.21 g, 59.4 mmol) added and the reaction mixture heated to reflux for 1.5 h. After cooling to room temperature, $H_2O$ (250 mL) was added and the mixture extracted with $CHCl_3$ (3×150 mL). The organic phases were combined, washed $H_2O$ (2×150 mL), dried ($MgSO_4$) and the solvent removed in vacuo. The residue was afterwards subjected to column chromatography [$SiO_2$, $CHCl_3$:MeOH 95:5 v/v, Rf=0.4] wherefrom D was obtained as a yellow oil (3.11 g, 87%). MS (MALDI): m/z (%)={600 (M+, 100)}.

Step C 2-(4,5-Bis[2-{2-(2-methoxyethoxy)ethoxy}ethylthio]-1,3-dithiole-2-ylidene)-5-methyl-1,3-dithiolo[4,5-c]pyrrole (9)

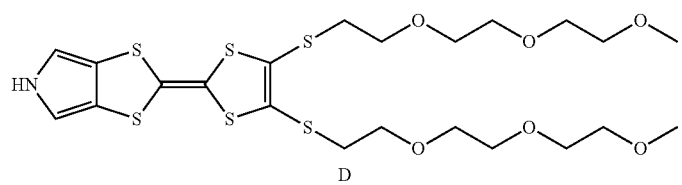

D

Compound D (890 mg, 1.48 mmol) was dissolved in anhydrous DMF (125 mL) and degassed with $N_2$ for 15 min., whereafter NaH (60% v/v suspension in mineral oil, 400 mg, 240 mg, 10.0 mmol) was added, whereby the color changed from yellow to orange. After 20 min., MeI (3.37 g, 23.7 mmol) was added to the mixture, resulting in a color change back to yellow. After 1.5 h, excess MeI was removed by stripping with $N_2$ for 15 min., followed by dropwise addition of a sat. NaCl-solution (50 mL) until gas evolution no longer could be observed. After extraction with $CHCl_3$ (250 mL), washing with sat. NaCl (2×250 mL), $H_2O$ (250 mL), and drying ($MgSO_4$), the solvent is removed in vacuo. The resulting residue was subjected to column chromatography [$SiO_2$, $CHCl_3$:MeOH 98:2 v/v, Rf=0.3] wherefrom compound 9 was obtained as an orange oil (749 mg, 82%). MS (MALDI): m/z (%)={613 (M+, 100)}.

Synthesis of 2,3-Bis(2-amidoethylthio)-6,7-bis(2-(4-nitrophenyl)ethylthio)-tetrathiafulvalene (compound 3)

Step A 4,5-Bis(2-amidoethylthio)-1,3-dithiole-2-thione (F)

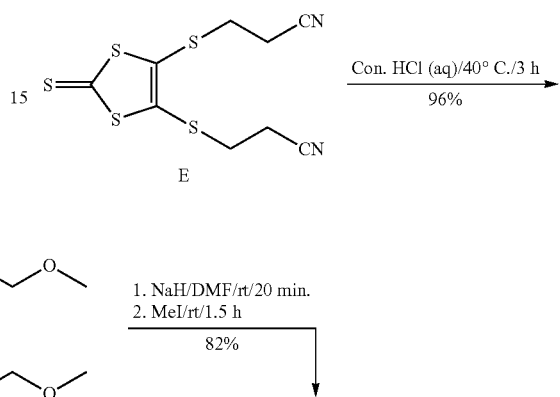

E

1. NaH/DMF/rt/20 min.
2. MeI/rt/1.5 h

82%

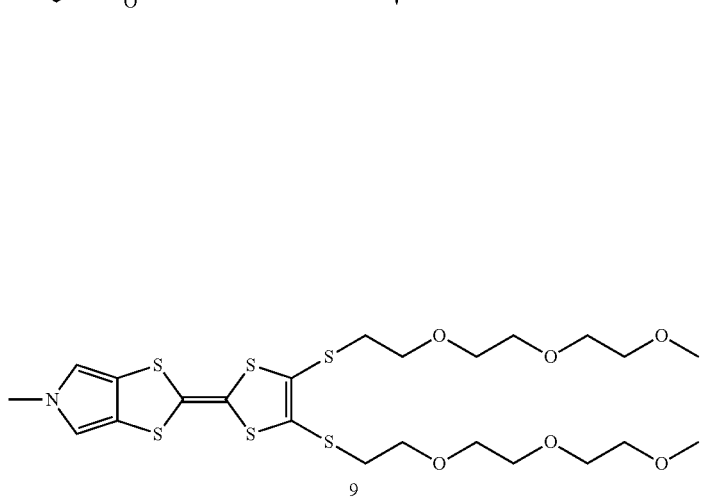

9

-continued

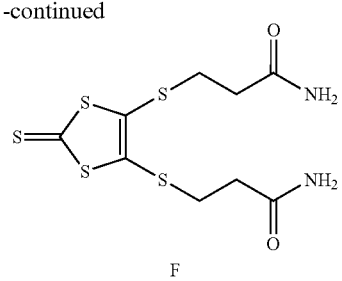

F 4,5-Bis(2-cyanoethylthio)-1,3-dithiole-2-thione (E) (see N. Svenstrup et al., Synthesis, 1994, 8, 809-812) (4.08 g, 13.4 mmol) was suspended in conc. HCl (320 mL) and heated to 40-42° C. for 3 h. The suspension was then poured into a mixture of ice/$H_2O$ (400 mL) and the product F isolated by filtration, washed with copious amounts of $H_2O$ and dried in vacuo. Recrystallization from 2-methoxyethanol/$H_2O$ yielded F as pale yellow needles (4.38 g, 96%). MS (EI): m/z (%)={340 (M+, 64), 166 (30), 72 (100)}.

Step B 2,3-Bis(2-amidoethylthio)-6,7-bis(2-(4-nitrophenyl)ethylthio)-tetrathiafulvalene (compound 3)

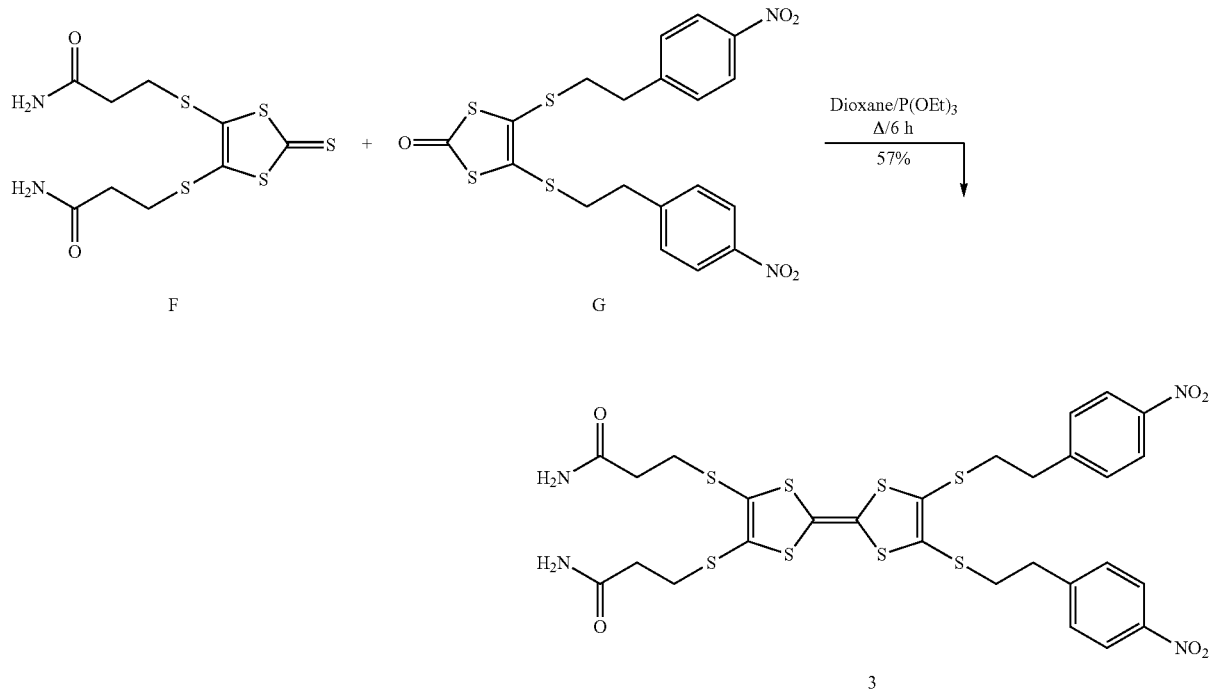

4,5-Bis(2-amidoethylthio)-1,3-dithiole-2-thione (F) (0.63 g, 1.85 mmol) and 4,5-bis(2-(4-nitrophenyl)ethylthio)-1,3-dithiole-2-one (G) (see K. B. Simonsen et al., Angew. Chem., Int. Ed., 1999, 38 (10), 1417-1420) (1.33 g, 2.77 mmol) were suspended in a mixture of anhydrous degassed dioxane (250 mL) and triethyl phosphite (45 mL) and heated to reflux for 6 h. After cooling to room temperature and removal of the solvents in vacuo, the residue was washed with copious amounts of MeOH and dried under vacuum. The residue were purified by column chromatography [SiO$_2$, I) CH$_2$Cl$_2$, II) CH$_2$Cl$_2$/MeOH 97:3, III) CH$_2$Cl$_2$/MeOH 94:6] yielding compound 3 as an orange solid (0.82 g, 57%). Mp: 191-193° C. MS (FAB): m/z (%)={772 (M$^+$)}.

Synthesis of 2-(4,5-Bis[2-(4-nitrophenyl)ethylthio]-1,3-dithiole-2-ylidene)-5-tosyl-1,3-dithiolo[4,5-c]pyrrole (compound 1)

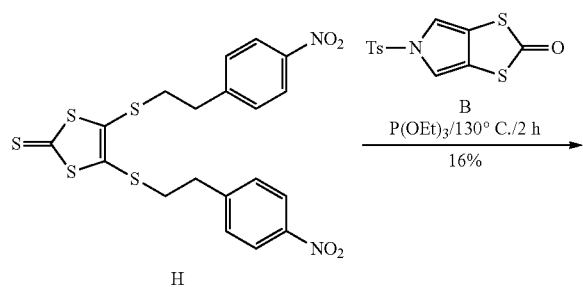

-continued

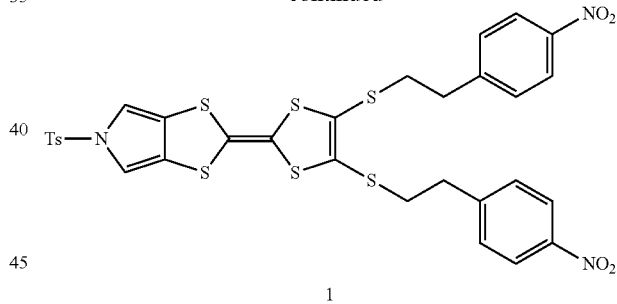

5-Tosyl-1,3-dithiolo[4,5-c]pyrrol-2-one (B) (see Jeppesen, J. O., et al., Organic Letters, 1999. 1(8): p. 1291-1294) (0.62 g, 2.00 mmol) and 4,5-bis(2-(4-nitrophenyl)ethylthio)-1,3-dithiole-2-thione (H) (see D. Damgaard et al., J. Mater. Chem., 2000, 10, 2249-2258) (2.00 g, 4.00 mmol) were dissolved in triethyl phosphite (15 ml) and heated to 130° C. for 2 h. Then the reaction mixture was concentrated in vacuo and the residue purified by column chromatography [SiO$_2$, CH$_2$Cl$_2$]. The red band was collected, the solvent removed in vacuo, and the residue recrystallized from CHCl$_3$/petroleum ether (b.p. 60-80° C.) to give orange granules of compound 1, (0.24 g, 16%); Mp: 143-144° C. PDMS (m/z): 759.3.

Synthesis of 2-(4,5-Bis[methoxycarbonyl]-1,3-dithiole-2-ylidene)-5-tosyl-1,3-dithiolo[4,5-c]pyrrole (compound 7)

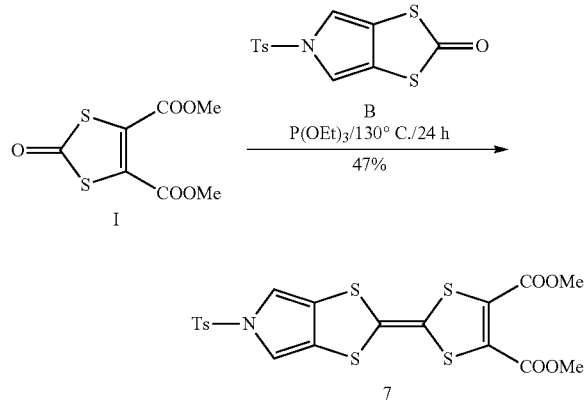

5-Tosyl-1,3-dithiolo[4,5-c]pyrrol-2-one (B) (see Jeppesen, J. O., et al., Organic Letters, 1999. 1(8): p. 1291-1294) (0.75 g, 2.40 mmol) and 4,5-bis(methoxycarbonyl)-1,3-dithiole-2-one (I) (see Baffreau, J., F. Dumur, and P. Hudhomme, Organic Letters, 2006. 8(7): p. 1307-1310) (3.20 g, 13.7 mmol) were mixed in o-xylene (80 ml) and heated to 130° C. Triethyl phosphite (8 ml) was added and the resulting reaction mixture stirred at 130° C. for 12 h, whereupon a second portion of I (1.6 g, 6.8 mmol) was added. The heating was continued another 12 h. Then the reaction mixture was concentrated in vacuo and the residue purified by column chromatography [SiO$_2$, PhMe/EtOAc 1:0→4:1 v/v]. This afforded, after removal of the solvents in vacuo, the product 7 as a red oil that solidified upon standing. Recrystallization from EtOAc/petrol ether yielded 7 as red needles (0.58 g, 47%). Mp: 166-167° C. MS (EI): m/z (%)={513 (M$^+$, 57), 358 ([M-Ts]$^+$, 100)}.

Synthesis of Bis-TTF (compound 2)

2,3-Bis(2-cyanoethylthio)-6,7-bis(methoxycarbonyl)tetrathiafulvalene J (see K. B. Simonsen et al., Synthesis, 1996, 3, 407-418) (1.84 g, 3.75 mmol) was dissolved in anhydrous DMF (120 mL) and degassed with N$_2$ for 15 min. CsOH.H$_2$O (0.66 g, 3.94 mmol) was dissolved in anhydrous degassed MeOH (10 mL) and added dropwise over 1 h to the previous solution. After ended addition, the reaction mixture was stirred for additional 40 min., before 4,4'-bis(bromomethyl)-2,2'-bipyridine (K) (see Ashton, P. R., et al., Chemistry—A European Journal, 1998. 4(4): p. 590-607), dissolved in anhydrous DMF (15 mL), was added in one portion. After stirring overnight the solvent was removed in vacuo. The residue was redissolved in CH$_2$Cl$_2$ (250 mL) and washed with H$_2$O (200 mL), sat. NaCl (4×200 mL) and H$_2$O (200 mL) and dried (Na$_2$SO$_4$), before the solvent was removed in vacuo. The remaining residue was purified by column chromatography [SiO$_2$, CH$_2$Cl$_2$/MeOH 100:2] affording compound 2 as a dark red compound (1.81 g, 92%). MS (FAB): m/z (%)={1054 (M$^+$)}

Synthesis of 2-(4,5-Bis[n-pentylthio]-1,3-dithiole-2-ylidene)-4,6-Dihydro-5-tosyl-1,3-dithiolo[4,5-c]pyrrole (compound 6)

1,3-Dihydro-N-tosyl-1,3-dithiolo[4,5-c]pyrrol-2-one (L) (see Jeppesen, J. O., et al., Organic Letters, 1999. 1(8): p. 1291-1294) (1.69 g, 5.4 mmol) and 4,5-bis(n-pentylthio)-1,3-dithiole-2-thione (M) (see B. M. Pedersen et. al., Eur. J.

Inorg. Chem., 2006, 15, 3099-3104) (1.50 g, 5.00 mmol) were mixed in distilled triethyl phosphite (20 ml) and rapidly heated to 130° C. Two more portions of M (a 0.9 g, 3 mmol) were added after 10 and 20 min., respectively. The reaction was then stirred at 130° C. for 5 h and then left to cool to room temperature. MeOH (150 ml) was added and the precipitate formed was collected and washed with MeOH (3×20 ml) to give a yellow powder. This crude product was redissolved in a mixture of $CH_2Cl_2$/MeOH 1:1 (100 ml). The solution was reduced in vacuo to approximately half the volume and the precipitate that formed was collected as a yellow powder which was subjected to column chromatography [$SiO_2$, PhMe/$CH_2Cl_2$ 9:1 v/v]. This afforded compound 6 as orange needles (1.63 g, 50%), mp: 136-137° C.

Synthesis of 2-(4,5-Bis[pentylthio]-1,3-dithiole-2-ylidene)-5-(p-amidinophenyl)-1,3-dithiolo[4,5-c]pyrrole (compound 8)

Step A 2-(4,5-Bis[pentylthio]-1,3-dithiole-2-ylidene)-1,3-dithiolo[4,5-c]pyrrole (P)

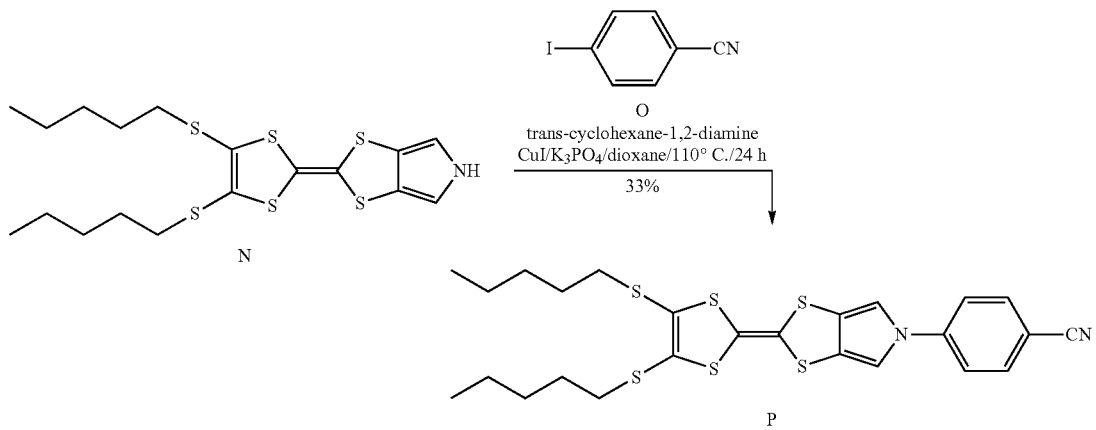

2-(4,5-Bis[pentylthio]-1,3-dithiole-2-ylidene)-1,3-dithiolo[4,5-c]pyrrole (N) (see Jeppesen, 10., et al., The Journal of Organic Chemistry, 2000. 65(18): p. 5794-5805) (0.34 g, 0.75 mmol) was mixed with 0 (0.34 g 1.51 mmol), $K_3PO_4$ (0.34 g, 1.51 mmol), CuI (0.03 g, 0.08 mmol), and trans-cyclohexane-1,2-diamine (0.02 mL, 0.15 mmol) in anhydrous dioxane (2 mL) in an oven-dried Schlenk tube and heated to 110° C. on an oil bath for 24 h. After cooling to room temperature, EtOAc (100 mL) was added. The resulting precipitate was isolated by filtration and washed with EtOAc (50 mL). The compound P was used without further purification (0.13 g 33%).

Step B 2-(4,5-Bis[pentylthio]-1,3-dithiole-2-ylidene)-5-(p-amidinophenyl)-1,3-dithiolo[4,5-c]pyrrole (8)

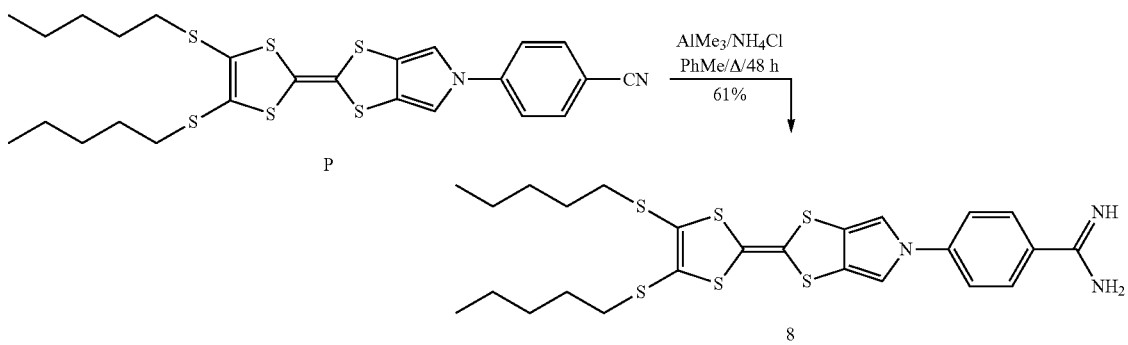

To a suspension of $NH_4Cl$ (0.29 g, 8.65 mmol) in PhMe (5 mL) was $AlMe_3$ (14 mL, 2 M in PhMe, 0.28 mol) added carefully and stirred for 1.5 h. To this was P (0.15 g, 0.27 mmol) in PhMe (10 mL) added and the mixture heated to reflux for 48 h. After cooling to room temperature, $NH_4Cl$ (3.15 g, 94.0 mmol) was added and followed by the very careful addition of 4 M NaOH (12 mL). The reaction mixture was then poured into 4 M NaOH (100 mL) and the organic phase isolated. After drying ($MgSO_4$) and evaporation of the solvent in vacuo was the remaining residue subjected to column chromatography [$SiO_2$, $CH_2Cl_2$, Rf=0.5] yielding compound 8 as a yellow powder (95.1 mg, 61%).

Sensor Array

Example 1

Preparation of Sensor Array by Hand

Compounds 1-15 from the list of compounds in Table 1 were chosen. To prepare the sensor array, the chemo-selective compounds with given numbers 6, 8, 10, 13 and 15 were dissolved in 1,2-dichlorobenzene (Sigma, St. Louis, USA), and chemo-selective compounds with given numbers 1-5, 7, 9, 11, 12 and 14 were dissolved in DMSO (Sigma, St. Louis, USA) to obtain a final concentration of 1% (w/v). Stock solutions of the compounds were stored in brown flasks at room temperature. Immediately after preparation of the solutions, the chemo-selective compounds were immobilized on a solid support (Kieselgel 60F254, Merck KGaA, Germany). Position and structure of compounds, are shown in FIG. 1. The volume of applied chemo-selective compounds was 1 µL per spot. Each individual spot was approximately 1.5 mm in diameter with the total size of the sensor array of approximately 2.5 cm×2.5 cm. Pictures were scanned through an ordinary flatbed scanner (Epson V750-M Pro Perfection scanner) directly after immobilization of compounds.

Example 2

Preparation of the Sensor Array by Micro-Spotting

Figure 2:
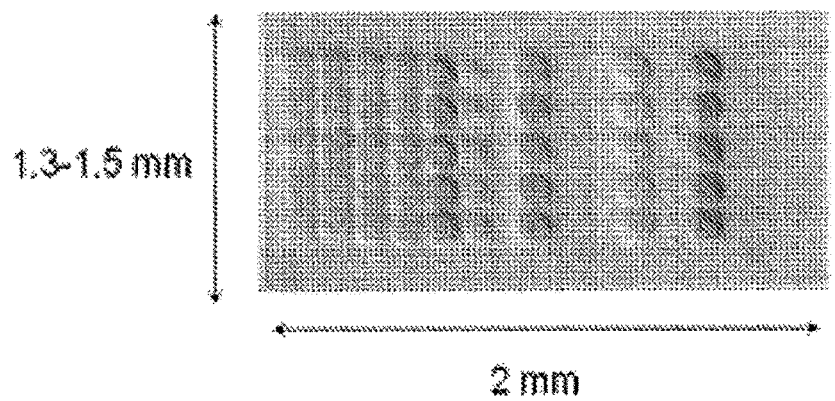
FIG. 2 shows a miniaturized sensor array (total size about 1.5 mm×2.0 mm) made of a nitrocellulose membrane where solutions of different compounds have been printed onto its surface. Each spot is about 110 µm in diameter, the centre to centre distance between individual spots is 150 µm and the total number of spots is 45.

The 15 solutions of the compounds described in Example 1 were used to prepare a miniaturized sensor array using a micro-contact spotting Spotbot2 instrument (Arrayit, Sunnyvale, Calif., USA) with a mounted SMP3 pin. Spot spacing was 150 µm. The pin has a flat surface, defined uptake channel which allows loading of 0.25 µL of a sample and produces spots of 110 µm in diameter. The solid support used here were both Kieselgel 60F254 membrane (Merck KGaA, Germany) and a nitrocellulose membrane (Schleicher & Schuell, Dassel, Germany). The volume per spot was not determined (a delivery volume of 600 pL was expected on a microscope slide surface). Pictures of the printed microarray were obtained by using an Olympus stereomicroscope with a mounted Olympus colored camera (Olympus, Center Valley, Pa., USA). FIG. 2 shows the results of the printed sensor array on a nitrocellulose membrane before exposure to analytes. Each spot was approximately 110 µm in diameter and the total size of the sensor array was approximately of 1.5 mm×2.0 mm.

Example 3

Use of Different Solid Supports

Different solid supports were used to prepare the sensor array according to the invention: Kieselgel 60F254 plates (Merck KGaA, Germany, PVDF membranes with hydrophilic properties (Millipore Corporation, Billerica, Mass., USA), nitrocellulose membranes (Schleicher&Schuell, Dassel, Germamy), polypropylene, polyester, nitrocellulose mixed ester, nylon, polyethersulfone, Teflon membranes, and glass fiber were from Stelitech (Sterlitech Corporation, Kent, Wash., USA). Chemo-selective compounds were manually deposited directly onto the solid support or deposited by using the micro-spotting technique as described in Example 1 and Example 2, respectively. FIG. 2 shows the micro-spotting experiments using nitrocellulose membrane.

Example 4

Detection of Organic and Inorganic Vapors

Analytes: acetone, acetic acid, 1,2-dichlorobenzene, 2,4-dinitrotoluene (DNT), formic acid, hydrochloric acid, methanol, propanol, toluene were obtained from Sigma (St. Louise, Mo., USA). Ethanol was ordered from Solveco Chemicals AB (Dramstadt, Germany). All chemicals were of analytical grade and used without further purification. Sensor arrays were prepared as described in Example 1. After scanning, each array was exposed to saturated analyte vapors at room temperature (DNT at 100° C.) for two minutes. Control measurements were performed at room temperature and elevated temperature of 100° C., respectively with ambient air. After exposure to analytes each array was scanned again. Each analysis was done in triplicates.

A colorimetric sensor array for detection of VOCs and DNT in a gas phase was designed using 15 chemo-selective compounds (compounds 1 to 15 of Tab. 1). Compounds were immobilized onto silica gel plates in the working volume of 1 µL. Since mass transport and time response are correlated values, saturated conditions of analytes (acetone, acetic acid, DNT, formic acid, hydrochloric acid, methanol, ethanol, propanol, and toluene) were prepared. Detection of acetone, acetic acid, formic acid, hydrochloric acid, methanol, ethanol, propanol, and toluene were performed at 24° C. DNT was detected at the elevated temperature of 100° C. Control measurements were performed at 24° C. and 100° C., respectively. Pictures were scanned twice through an ordinary flatbed scanner (Epson V750-M Pro Perfection scanner) first time immediately after immobilization of chemo-selective compounds and the second time after exposure to analytes. The experiment duration was 2 minutes for each analyte. Pictures were obtained at 600 dots per inch in the RGB color format. Results were analyzed by using MatLab software. Using the red, green and blue color scheme color changes for each compound were analyzed before and after exposure to the analyte. Color changes of each dye were analyzed using the red, green, and blue color scheme. In this model every color is provided as red, green, and blue color (RGB) with RGB values given in the 0-255 integer range. The minimum intensity of the color gives black (0,0;0) and maximum white color (255;255;255). After the dye was located and converted to RGB values, we calculated the median value of each. We used the median instead of the mean in order to be more robust to noise and outliers. A difference map was obtained from the values of red, green or blue colors after exposure minus the value of red, green or blue color before the exposure. Since the RGB color scheme does not allow negative values the absolute difference was taken. Further in order to enhance the visibility of the colors difference maps the RGB values were first scaled with a factor of 5 and then shifted from 5 to 10. The instances where the difference map (before scaling)

resulted in a color value lower than 3 the pixel was rounded down to a color value of 0 (see Table 2 below).

By using the chemo-selective compounds we were able to apply the colorimetric sensor array for screening volatile organic compounds, like acetone, acetic acid, ethanol, formic acid, hydrochloric acid, methanol, propanol, and toluene, and also for probing explosives, like DNT in the gas phase. Color change patterns manifest the presence of a specific or given targets, in other words, the observed color change patterns indicate a particular vapour of the individual analyte or mixture of analytes. Digital images of arrays before and after exposure can be used for generating of the color difference map by pixel subtraction. A difference map is able to compose a unique fingerprint for each analyte or its mixture. For each analyte average color change profile was obtained and shown in FIGS. 3 and 4.

Figure 3:
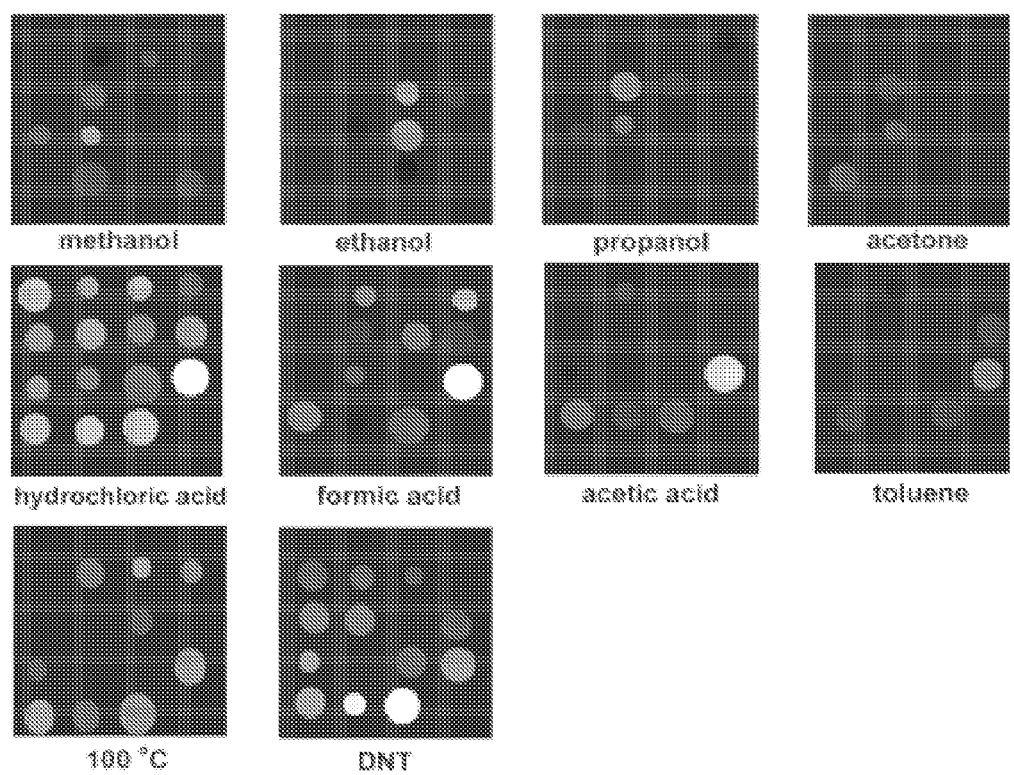
FIG. 3 shows difference maps of the colorimetric sensor array according to the present invention obtained in the presence of volatile organic compounds and DNT in the gas phase. Images were generated after the mathematical calculations of the colour changes; and are presented as the difference map obtained from the absolute values of RGB values of each dye spot before and after exposure.

The resulting colorimetric sensor was used for the vapor analysis of acetone, acetic acid, ethanol, formic acid, hydrochloric acid, methanol, propanol, toluene, and DNT. The analysis demonstrates the familiar similarity in the response among compounds with common organic properties: alcohols, organic and inorganic acids, ketones and arenes. The strong signal was obtained in the presence of acids, the color-changes profile shows the significant different between inorganic and organic acids (FIG. 3). By using the chemo-selective compounds array was possible to identify closely related alcohols; some compounds selectively changed color in the presence of methanol (comp. no. 3, 4, 6, 6, 7, 9, 10, 14, 15), ethanol (comp. no. 6, 9, 10) and propanol (comp. no. 6, 9, 10). Some compounds selectively changed color in the presence of hydrochloric acid (no. 1, 2, 3, 4, 5, 6, 7, 8, 9, 10, 11, 12, 13, 14, and 15), formic acid (no. 1, 2, 4, 6, 7, 8, 9, 10, 11, 12, 13, 14, and 15), acetic acid (comp. no. 2, 12, 13, 14, and 15), acetone (comp. no. 6, 10, 13), toluene (comp. no. 12, 13, 15), DNT (comp. no. 1, 2, 3, 5, 6, 8, 9, 11, 12, 13, 14, and 15).

Since explosives have low vapor pressure at ambient conditions, DNT was heated up to 100° C. to increase the analyte vapor. The same working principle will be used in the commercialized sensor. The slide with the ordinary immobilized chemo-selective compounds was also heated up at the same elevated temperature; those results were used as a control. Obtained results are presented in the FIG. 3. According to the evaluated data, the chemo-selective compounds were not only able to detect specific analytes, they were also able to change the color pattern specifically at the high temperature-Control-at-100° C. (comp. no. 2, 3, 4, 7, 9, 12, 13, 14 and 15) (FIG. 3).

TABLE 2

Proprieties of the compounds resulting in color changes in real colors and RGB color format. RGB colors were generated after the mathematical calculation of color changes, and presented as the absolute value of Red, Green, and Blue values obtained independently from each dye spot as the difference in color changes after and before the exposure to the target.

| Analyte | Color change | | Color channel | | |
|---|---|---|---|---|---|
| | Before exposure | After exposure | R | G | B |
| Compound number 1 | | | | | |
| Methanol | Light orange | No change | 0 | 0 | 0 |
| Ethanol | Light orange | No change | 0 | 0 | 0 |
| Propanol | Light orange | No change | 0 | 0 | 0 |
| Hydrochloric acid | Light orange | Yellow-brown | 120 | 195 | 180 |
| Formic acid | Light orange | Orange | 0 | 30 | 0 |
| Acetic acid | Light orange | No change | 0 | 0 | 0 |
| Acetone | Light orange | No change | 0 | 0 | 0 |
| Toluene | Light orange | No change | 0 | 0 | 0 |
| DNT | Light orange | Deep orange | 0 | 45 | 0 |
| Control-at-100° C. | Light orange | No change | 0 | 0 | 0 |
| Compound number 2 | | | | | |
| Methanol | Light brown | Brown | 30 | 0 | 0 |
| Ethanol | Light brown | No change | 0 | 0 | 0 |
| Propanol | Light brown | No change | 0 | 0 | 0 |
| Hydrochloric acid | Light brown | Deep brown | 135 | 195 | 180 |
| Formic acid | Light brown | Deep brown | 60 | 135 | 75 |
| Acetic acid | Light brown | Deep brown | 0 | 30 | 0 |
| Acetone | Light brown | No change | 0 | 0 | 0 |
| Toluene | Light brown | No change | 0 | 0 | 0 |
| DNT | Light brown | Deep brown | 30 | 45 | 0 |
| Control-at-100° C. | Light brown | Deep brown | 60 | 75 | 90 |
| Compound number 3 | | | | | |
| Methanol | Light orange | Orange | 0 | 0 | 60 |
| Ethanol | Light orange | No change | 0 | 0 | 0 |
| Propanol | Light orange | No change | 0 | 0 | 0 |
| Hydrochloric acid | Light orange | Brown | 105 | 195 | 240 |
| Formic acid | Light orange | No change | 0 | 75 | 255 |
| Acetic acid | Light orange | No change | 0 | 0 | 0 |
| Acetone | Light orange | No change | 0 | 0 | 0 |
| Toluene | Light orange | No change | 0 | 0 | 0 |

TABLE 2-continued

Proprieties of the compounds resulting in color changes in real colors and RGB color format. RGB colors were generated after the mathematical calculation of color changes, and presented as the absolute value of Red, Green, and Blue values obtained independently from each dye spot as the difference in color changes after and before the exposure to the target.

| Analyte | Color change | | Color channel | | |
|---|---|---|---|---|---|
| | Before exposure | After exposure | R | G | B |
| DNT | Light orange | Deep brown | 0 | 0 | 75 |
| Control-at-100° C. | Light orange | Brown | 60 | 255 | 255 |
| Compound number 4 | | | | | |
| Methanol | Brown | Light grey-brown | 60 | 0 | 0 |
| Ethanol | Brown | No change | 0 | 0 | 0 |
| Propanol | Brown | No change | 0 | 0 | 0 |
| Hydrochloric acid | Brown | Grey-brown | 105 | 0 | 0 |
| Formic acid | Brown | Grey-brown | 105 | 30 | 0 |
| Acetic acid | Brown | No change | 0 | 0 | 0 |
| Acetone | Brown | No change | 0 | 0 | 0 |
| Toluene | Brown | No change | 0 | 0 | 0 |
| DNT | Brown | No change | 0 | 0 | 0 |
| Control-at-100° C. | Brown | Deep brown | 30 | 45 | 90 |
| Compound number 5 | | | | | |
| Methanol | Faint yellow-orange | No change | 0 | 0 | 0 |
| Ethanol | Faint yellow-orange | No change | 0 | 0 | 0 |
| Propanol | Faint yellow-orange | No change | 0 | 0 | 0 |
| Hydrochloric acid | Faint yellow-orange | Grey-brown | 0 | 120 | 210 |
| Formic acid | Faint yellow-orange | No change | 45 | 75 | 120 |
| Acetic acid | Faint yellow-orange | No change | 0 | 0 | 0 |
| Acetone | Faint yellow-orange | No change | 0 | 0 | 0 |
| Toluene | Faint yellow-orange | No change | 0 | 0 | 0 |
| DNT | Faint yellow-orange | Orange | 30 | 75 | 90 |
| Control-at-100° C. | Faint yellow-orange | No change | 0 | 0 | 0 |
| Compound number 6 | | | | | |
| Methanol | Light brown with Faint yellow-orange periphery | Brown with light brown periphery | 0 | 45 | 60 |
| Ethanol | Light brown with Faint yellow-orange periphery | Brown with light brown periphery | 0 | 60 | 105 |
| Propanol | Light brown with Faint yellow-orange periphery | Brown with light brown periphery | 0 | 105 | 105 |
| Hydrochloric acid | Light brown with Faint yellow-orange periphery | Deep brown with light brown periphery | 60 | 150 | 150 |
| Formic acid | Light brown with Faint yellow-orange periphery | Grey-brown | 255 | 255 | 255 |
| Acetic acid | Light brown with Faint yellow-orange periphery | No change | 0 | 0 | 0 |
| Acetone | Light brown with Faint yellow-orange periphery | Brown with light brown periphery | 0 | 45 | 30 |
| Toluene | Light brown with Faint yellow-orange periphery | No change | 0 | 0 | 0 |
| DNT | Light brown with Faint yellow-orange periphery | Brown with light brown periphery | 45 | 75 | 45 |
| Control-at-100° C. | Light brown with Faint yellow-orange periphery | No change | 0 | 0 | 0 |
| Compound number 7 | | | | | |
| Methanol | Light brown | Brown | 0 | 0 | 30 |
| Ethanol | Light brown | No change | 0 | 0 | 0 |
| Propanol | Light brown | No change | 0 | 0 | 0 |
| Hydrochloric acid | Light brown | Grey-brown | 90 | 75 | 45 |
| Formic acid | Light brown | Grey-brown | 45 | 60 | 45 |
| Acetic acid | Light brown | No change | 0 | 0 | 0 |

TABLE 2-continued

Proprieties of the compounds resulting in color changes in real colors and RGB color format. RGB colors were generated after the mathematical calculation of color changes, and presented as the absolute value of Red, Green, and Blue values obtained independently from each dye spot as the difference in color changes after and before the exposure to the target.

| | Color change | | Color channel | | |
|---|---|---|---|---|---|
| Analyte | Before exposure | After exposure | R | G | B |
| Acetone | Light brown | No change | 0 | 0 | 0 |
| Toluene | Light brown | No change | 0 | 0 | 0 |
| DNT | Light brown | No change | 0 | 0 | 0 |
| Control-at-100° C. | Light brown | Deep brown | 0 | 0 | 45 |
| Compound number 8 | | | | | |
| Methanol | Light yellow | No change | 0 | 0 | 0 |
| Ethanol | Light yellow | No change | 0 | 0 | 0 |
| Propanol | Light yellow | No change | 0 | 0 | 0 |
| Hydrochloric acid | Light yellow | Dark grey-yellow | 0 | 135 | 45 |
| Formic acid | Light yellow | Grey-yellow | 60 | 255 | 120 |
| Acetic acid | Light yellow | No change | 0 | 0 | 0 |
| Acetone | Light yellow | No change | 0 | 0 | 0 |
| Toluene | Light yellow | No change | 0 | 0 | 0 |
| DNT | Light yellow | Bright yellow | 0 | 45 | 0 |
| Control-at-100° C. | Light yellow | No change | 0 | 0 | 0 |
| Compound number 9 | | | | | |
| Methanol | Yellow | Light yellow | 0 | 0 | 90 |
| Ethanol | Yellow | Light yellow | 0 | 0 | 60 |
| Propanol | Yellow | Light yellow | 0 | 0 | 45 |
| Hydrochloric acid | Yellow | Grey-yellow | 0 | 165 | 45 |
| Formic acid | Yellow | Dark grey-yellow | 255 | 255 | 180 |
| Acetic acid | Yellow | No change | 0 | 0 | 0 |
| Acetone | Yellow | No change | 0 | 0 | 0 |
| Toluene | Yellow | No change | 0 | 0 | 0 |
| DNT | Yellow | Dark yellow | 60 | 255 | 75 |
| Control-at-100° C. | Yellow | Bright yellow | 0 | 45 | 0 |
| Compound number 10 | | | | | |
| Methanol | Yellow | Light yellow | 0 | 255 | 255 |
| Ethanol | Yellow | Light yellow | 0 | 45 | 165 |
| Propanol | Yellow | Light yellow | 0 | 105 | 165 |
| Hydrochloric acid | Yellow | Light yellow | 0 | 75 | 90 |
| Formic acid | Yellow | Light yellow | 0 | 60 | 210 |
| Acetic acid | Yellow | No change | 0 | 0 | 0 |
| Acetone | Yellow | Light yellow | 0 | 60 | 120 |
| Toluene | Yellow | No change | 0 | 0 | 0 |
| DNT | Yellow | No change | 0 | 0 | 0 |
| Control-at-100° C. | Yellow | No change | 0 | 0 | 0 |
| Compound number 11 | | | | | |
| Methanol | Brown-yellow | No change | 0 | 0 | 0 |
| Ethanol | Brown-yellow | No change | 0 | 0 | 0 |
| Propanol | Brown-yellow | No change | 0 | 0 | 0 |
| Hydrochloric acid | Brown-yellow | Light brown-yellow | 0 | 30 | 105 |
| Formic acid | Brown-yellow | Light brown-yellow | 0 | 30 | 45 |
| Acetic acid | Brown-yellow | No change | 0 | 0 | 0 |
| Acetone | Brown-yellow | No change | 0 | 0 | 0 |
| Toluene | Brown-yellow | No change | 0 | 0 | 0 |
| DNT | Brown-yellow | Light brown-yellow | 45 | 60 | 60 |
| Control-at-100° C. | Brown-yellow | No change | 0 | 0 | 0 |
| Compound number 12 | | | | | |
| Methanol | Brown | No change | 0 | 0 | 0 |
| Ethanol | Brown | No change | 0 | 0 | 0 |
| Propanol | Brown | No change | 0 | 0 | 0 |
| Hydrochloric acid | Brown | Red-brown | 255 | 255 | 255 |
| Formic acid | Brown | Red-brown | 255 | 255 | 255 |
| Acetic acid | Brown | Grey-brown | 180 | 210 | 180 |

TABLE 2-continued

Proprieties of the compounds resulting in color changes in real colors and RGB color format. RGB colors were generated after the mathematical calculation of color changes, and presented as the absolute value of Red, Green, and Blue values obtained independently from each dye spot as the difference in color changes after and before the exposure to the target.

| Analyte | Color change | | Color channel | | |
|---|---|---|---|---|---|
| | Before exposure | After exposure | R | G | B |
| Acetone | Brown | No change | 0 | 0 | 0 |
| Toluene | Brown | Deep brown | 90 | 75 | 60 |
| DNT | Brown | Grey-pink | 0 | 165 | 0 |
| Control-at-100° C. | Brown | Grey-pink | 0 | 255 | 0 |
| Compound number 13 | | | | | |
| Methanol | Faint grey-pink | No change | 0 | 0 | 0 |
| Ethanol | Faint grey-pink | No change | 0 | 0 | 0 |
| Propanol | Faint grey-pink | No change | 0 | 0 | 0 |
| Hydrochloric acid | Faint grey-pink | Dark grey | 240 | 90 | 225 |
| Formic acid | Faint grey-pink | Grey | 255 | 75 | 225 |
| Acetic acid | Faint grey-pink | Blue-pink | 75 | 45 | 75 |
| Acetone | Faint grey-pink | Faint brown-red | 0 | 30 | 0 |
| Toluene | Faint grey-pink | Faint blue-pink | 45 | 30 | 30 |
| DNT | Faint grey-pink | Faint pink | 75 | 150 | 255 |
| Control-at-100° C. | Faint grey-pink | Faint pink | 0 | 180 | 255 |
| Compound number 14 | | | | | |
| Methanol | Yellow | Light grey-yellow | 0 | 30 | 0 |
| Ethanol | Yellow | No change | 0 | 0 | 0 |
| Propanol | Yellow | No change | 0 | 0 | 0 |
| Hydrochloric acid | Yellow | Dark grey-yellow | 105 | 210 | 150 |
| Formic acid | Yellow | Grey-yellow | 195 | 255 | 90 |
| Acetic acid | Yellow | Light grey-yellow | 0 | 30 | 0 |
| Acetone | Yellow | No change | 0 | 0 | 0 |
| Toluene | Yellow | No change | 0 | 0 | 0 |
| DNT | Yellow | Dark brown-yellow | 255 | 255 | 225 |
| Control-at-100° C. | Yellow | Light grey-yellow | 0 | 45 | 0 |
| Compound number 15 | | | | | |
| Methanol | Yellow | Light grey-yellow | 0 | 30 | 0 |
| Ethanol | Yellow | No change | 0 | 0 | 0 |
| Propanol | Yellow | No change | 0 | 0 | 0 |
| Hydrochloric acid | Yellow | Dark grey-yellow | 150 | 165 | 225 |
| Formic acid | Yellow | Dark grey-yellow | 255 | 255 | 210 |
| Acetic acid | Yellow | Light grey-yellow | 60 | 45 | 45 |
| Acetone | Yellow | No change | 0 | 0 | 0 |
| Toluene | Yellow | Bright yellow | 30 | 30 | 0 |
| DNT | Yellow | Brown-yellow | 255 | 255 | 255 |
| Control-at-100° C. | Yellow | Light brown-yellow | 0 | 90 | 120 |

Example 5

Detection of Explosives in a Gas Phase

Figure 4:
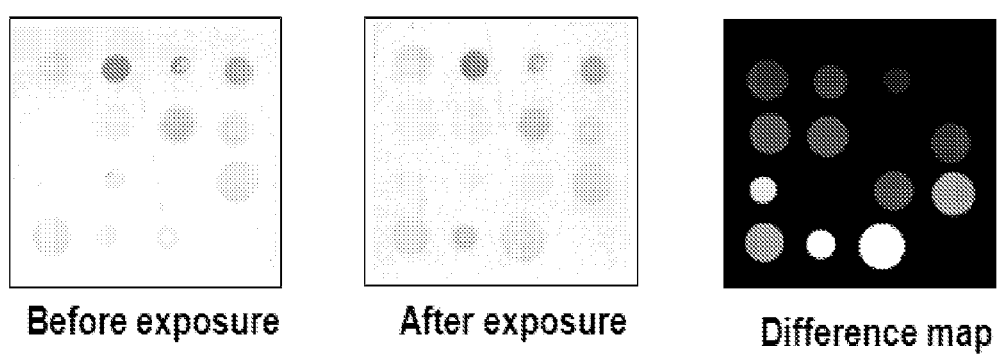
FIG. 4 shows a difference map of the colorimetric sensor array according to the present invention obtained before and after exposure of DNT in the gas phase. The image was generated after the mathematical analysis of the colour changes.

To detect explosives, like DNT, RDX, HMX, TAPT, 15 chemo-selective compounds of general formula I were immobilized on the silica gel support in the working volume of 1 µL (FIG. 1). To perform the survey DNT, RDX, HMX and TAPT were ordered from Sigma (St. Louise, Mo., USA). Explosives were tested separately at a working amount of 10 mg. Since explosives have a low vapour pressure at room temperature experiments were performed at the elevated temperature of 100° C.; analytes were heated up to reach the temperature of 100° C. Experiments were of 2 minute duration. Control experiments were also performed at 100° C. in duration of 2 minutes. Pictures were scanned using a flatbed scanner (Epson V750-M Pro Perfection scanner) immediately after immobilization of chemo-selective compounds and after exposure of explosives. Pictures were obtained at 600 dots per inch in RGB color format. In this work, after the exposure of DNT, RDX, HMX and TAPT chemo-selective compounds changed colors. FIG. 4 shows the application of the colorimetric sensor array for detection of DNT. Images of the array were taken before and after exposure of DNT vapors, and the difference map obtained from red, green, and blue values of the pictures. Digital imaging of the colorimetric array before and after exposure can be used for generating of the color difference map by pixel subtraction.

A difference map is able to compose a unique fingerprint for each explosive. To evaluate the color changes of chemo-selective compounds in the presence of explosives, the similar data analysis was performed as described above for VOCs. The changes in a color signature of the chemoselective compounds indicate the presence of explosives in gas phase. By using the chemo-selective array it was possible to identify DNT (comp. no. 1, 2, 3, 5, 6, 8, 9, 11, 12, 13, 14, and 15), TATP (comp. no. 2, 4, 10, and 12), some compounds selectively changed color in the presence of RDX (no. 1, 4, 5, 7, 10, and 13) and HMX (comp. no. 4, 5, 10) (see Table 3 below).

The simple colorimetric sensor array can be useful for detection and/or identification of volatile organic compounds in air as the present molecules have capability for recognizing specific analytes as described supra.

TABLE 3

Detection of explosives using the colorimetric sensor array. Color changes presented in RGB color format. RGB colors were generated as color changes before and after exposure of explosives, and the mathematical calculation of color changes was performed, and presented as the absolute value of Red, Green, and Blue values obtained independently from each dye spot.

| Example | Explosive Compound number | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| DNT | | | | | | | | | | | | | | | |
| $R_{channel}$ | 0 | 30 | 0 | 0 | 30 | 45 | 0 | 0 | 60 | 0 | 45 | 0 | 75 | 255 | 255 |
| $G_{channel}$ | 45 | 45 | 0 | 0 | 75 | 75 | 0 | 45 | 255 | 0 | 60 | 165 | 150 | 255 | 255 |
| $B_{channel}$ | 0 | 0 | 75 | 0 | 90 | 45 | 0 | 0 | 75 | 0 | 60 | 0 | 255 | 225 | 255 |
| TATP | | | | | | | | | | | | | | | |
| $R_{channel}$ | 0 | 15 | 0 | 20 | 0 | 0 | 0 | 0 | 0 | 50 | 0 | 10 | 0 | 0 | 0 |
| $G_{channel}$ | 0 | 10 | 0 | 0 | 0 | 0 | 10 | 0 | 0 | 20 | 0 | 0 | 0 | 0 | 0 |
| $B_{channel}$ | 15 | 0 | 0 | 20 | 35 | 5 | 15 | 0 | 15 | 15 | 0 | 20 | 30 | 15 | 10 |
| RDX | | | | | | | | | | | | | | | |
| $R_{channel}$ | 0 | 5 | 0 | 25 | 10 | 0 | 0 | 0 | 0 | 15 | 0 | 0 | 10 | 0 | 0 |
| $G_{channel}$ | 10 | 0 | 0 | 0 | 10 | 0 | 10 | 0 | 0 | 10 | 0 | 0 | 0 | 0 | 0 |
| $B_{channel}$ | 10 | 0 | 0 | 35 | 30 | 10 | 20 | 30 | 25 | 0 | 0 | 20 | 30 | 20 | 0 |
| HMX | | | | | | | | | | | | | | | |
| $R_{channel}$ | 0 | 10 | 0 | 30 | 0 | 0 | 0 | 0 | 0 | 45 | 0 | 0 | 0 | 0 | 0 |
| $G_{channel}$ | 0 | 0 | 0 | 10 | 10 | 20 | 0 | 0 | 0 | 25 | 0 | 5 | 0 | 0 | 0 |
| $B_{channel}$ | 10 | 5 | 0 | 15 | 30 | 0 | 15 | 0 | 20 | 20 | 0 | 0 | 30 | 0 | 0 |
| Control-at-100° C. | | | | | | | | | | | | | | | |
| $R_{channel}$ | 0 | 10 | 10 | 7 | 0 | 0 | 15 | 0 | 15 | 0 | 0 | 0 | 0 | 0 | 0 |
| $G_{channel}$ | 0 | 10 | 20 | 8 | 0 | 0 | 0 | 0 | 0 | 0 | 0 | 0 | 15 | 0 | 10 |
| $B_{channel}$ | 0 | 15 | 20 | 7 | 0 | 0 | 0 | 0 | 0 | 0 | 0 | 0 | 20 | 20 | 15 |

Example 6

Detection of Illegal Drugs in Gas Phase, Part I

In the present example the colorimetric sensor array with a plurality of chemo-selective compounds was shown to be suitable for detection of illegal drugs.

In similar order, again, 15 chemo-selective compounds of general formula I were immobilized on the silica gel support in the working volume of 1 μL. To increase the array sensitivity samples containing isosafrole (Sigma, St. Louis, USA) and phenylacetone (Sigma, St. Louis, USA) were heated up at the elevated temperature of 100° C. This technique was applied to elevate vapors emanating by illegal drugs.

The same detection principle was applied for identification of illegal drugs as has been described above for detection of explosives and VOCs. Herein, the colorimetric sensor was applied for detection of isosafrole and phenylacetone. Isosafrole and phenylacetone are precursors of illegal drugs which can be utilized for synthesis of "ecstasy".

Isosafrole is an aromatic organic chemical that has an odor similar to licorice and anise, and used for making soap and perfumes, as well as used as a preservative and antiseptic agent. Phenylacetone is an aromatic organic chemical with odor of anise. Phenylacetone can be used in production of pesticides and anticoagulants. However, phenylacetone has a strong effect on the sympathetic nervous system and can be used as an alternative material for synthesis of amphetamine and "ecstasy". As used herein, the chemo-selective compounds were able to change color in the presence of isosafrole and phenylacetone. The representation of color changes in RGB format is presented in Table 4. The colorimetric sensor has shown a large response to the presence of phenylacetone (comp. no. 1, 3, 4, 5, 7, 9, 10) and for isosafrole (comp. no. 1, 4, 7, 9 and 13), respectively.

Example 7

Detection of Illegal Drugs in Gas Phase, Part II

The colorimetric sensor array can be employed for effective and fast monitoring of narcotics. The colorimetric sensor array can be used as an alternative sensor for effective real-time survey of different types of illegal drugs, like for example LSD.

The colorimetric sensor array was applied for detecting LSD. The array was performed at elevated temperature of 100° C. In the array of 15 chemo-selective compounds the silica gel membrane was used as a supporting material. Chemo-selective compounds were applied in the working volume of 1 μL in order presented in FIG. 1. The similar detection principle was applied for identification of LSD as has been described above in detection of explosives and VOCs.

The RGB color format was used to extract data from the sensor; the results are presented in Table 4. The sensor showed a significant response wherein chemo-selective compounds were able to detect the presence of LSD in the gas phase (comp. no. 4, 8, 10, 14, and 15) (see Table 4 below).

Pork minced meat and Alaska Pollack fish were used in current experiments. Tested samples were kept at room temperature (approximately 24° C.) for 2 days, meanwhile control samples into a refrigerator at 4° C. for 2 days, respectively. Detection of vapours emanating by bacteria were performed at 24° C. Experiments were of 2 minute in duration. Pictures were scanned through an ordinary flatbed scanner (Epson V750-M Pro Perfection scanner) immediately after immobilization of chemo-selective compounds

TABLE 4

Detection of Illegal drugs using the colorimetric sensor array. Color changes presented in RGB color format. RGB colors were generated as color changes before and after exposure of illegal drugs, and the mathematical calculation of color changes was performed, and presented as the absolute value of Red, Green, and Blue values obtained independently from each dye spot.

| | Drugs Compound number | | | | | | | | | | | | | | |
|---|---|---|---|---|---|---|---|---|---|---|---|---|---|---|---|
| Example | 1 | 2 | 3 | 4 | 5 | 6 | 7 | 8 | 9 | 10 | 11 | 12 | 13 | 14 | 15 |
| Phenylacetone | | | | | | | | | | | | | | | |
| $R_{channel}$ | 9 | 0 | 15 | 40 | 10 | 0 | 15 | 0 | 15 | 0 | 0 | 0 | 0 | 0 | 0 |
| $G_{channel}$ | 15 | 0 | 9 | 22 | 10 | 0 | 10 | 0 | 0 | 30 | 0 | 0 | 0 | 0 | 0 |
| $B_{channel}$ | 30 | 0 | 0 | 15 | 20 | 0 | 20 | 15 | 15 | 15 | 0 | 0 | 0 | 30 | 0 |
| Isosafrole | | | | | | | | | | | | | | | |
| $R_{channel}$ | 15 | 0 | 10 | 25 | 0 | 0 | 10 | 0 | 15 | 0 | 0 | 0 | 20 | 0 | 0 |
| $G_{channel}$ | 10 | 0 | 0 | 0 | 0 | 0 | 0 | 0 | 0 | 15 | 0 | 0 | 0 | 0 | 0 |
| $B_{channel}$ | 10 | 15 | 0 | 15 | 25 | 10 | 15 | 40 | 20 | 0 | 0 | 20 | 20 | 20 | 10 |
| LSD | | | | | | | | | | | | | | | |
| $R_{channel}$ | 0 | 0 | 0 | 20 | 0 | 0 | 0 | 0 | 0 | 0 | 0 | 0 | 0 | 0 | 0 |
| $G_{channel}$ | 0 | 0 | 0 | 0 | 0 | 0 | 0 | 20 | 0 | 20 | 0 | 0 | 0 | 20 | 15 |
| $B_{channel}$ | 0 | 0 | 0 | 15 | 20 | 0 | 0 | 20 | 0 | 20 | 0 | 15 | 20 | 40 | 15 |
| Control-at-100° C. | | | | | | | | | | | | | | | |
| $R_{channel}$ | 0 | 10 | 10 | 7 | 0 | 0 | 15 | 0 | 15 | 0 | 0 | 0 | 0 | 0 | 0 |
| $G_{channel}$ | 0 | 10 | 20 | 8 | 0 | 0 | 0 | 0 | 0 | 0 | 0 | 0 | 15 | 0 | 10 |
| $B_{channel}$ | 0 | 15 | 20 | 7 | 0 | 0 | 0 | 0 | 0 | 0 | 0 | 0 | 20 | 20 | 15 |

Example 8

Detection of Food Freshness

The colorimetric sensor according to the present invention can be used to define the presence of bacteria on the surface of food samples as mentioned supra. The compounds of general formula I were applied to detect presence of bacteria in minced meat and fish samples.

and after exposure of analytes. Pictures were obtained at 600 dots per inch in RGB color format. The similar data analysis was performed. It would appear that chemo-selective compounds were able to change color and detect food spoilage in samples. Color change results are presented in Table 5 below. According to the data analysis the chemo-selective compounds were able to detect the products of bacteria metabolism in pork minced meat (comp. no. 7) and Alaska Pollack fish (comp. no. 8 and 10) samples (Tab. 5).

TABLE 5

The colorimetric sensor array was used for detecting vapour emanating from food spoilage bacteria. Color changes are presented in the RGB color format. RGB colors were generated as color changes before and after exposure to gases emanating from bacteria and the mathematical calculation of color changes was performed, and presented as the absolute value of Red, Green, and Blue values obtained independently from each dye spot.

| | Food quality Compound number | | | | | | | | | | | | | | |
|---|---|---|---|---|---|---|---|---|---|---|---|---|---|---|---|
| Example | 1 | 2 | 3 | 4 | 5 | 6 | 7 | 8 | 9 | 10 | 11 | 12 | 13 | 14 | 15 |
| Minced Meat | | | | | | | | | | | | | | | |
| $R_{channel}$ | 10 | 10 | 0 | 0 | 0 | 0 | 0 | 0 | 10 | 0 | 0 | 0 | 0 | 0 | 0 |
| $G_{channel}$ | 0 | 0 | 0 | 0 | 0 | 0 | 0 | 0 | 0 | 0 | 0 | 0 | 0 | 0 | 0 |
| $B_{channel}$ | 0 | 0 | 0 | 0 | 0 | 0 | 20 | 0 | 0 | 0 | 0 | 10 | 0 | 0 | 10 |

TABLE 5-continued

The colorimetric sensor array was used for detecting vapour emanating from food spoilage bacteria. Color changes are presented in the RGB color format. RGB colors were generated as color changes before and after exposure to gases emanating from bacteria and the mathematical calculation of color changes was performed, and presented as the absolute value of Red, Green, and Blue values obtained independently from each dye spot.

| Example | Food quality Compound number | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Fish | | | | | | | | | | | | | | | |
| $R_{channel}$ | 0 | 0 | 0 | 0 | 0 | 0 | 0 | 0 | 0 | 0 | 0 | 0 | 0 | 0 | 0 |
| $G_{channel}$ | 0 | 0 | 0 | 0 | 0 | 0 | 0 | 10 | 0 | 0 | 0 | 0 | 0 | 0 | 0 |
| $B_{channel}$ | 0 | 0 | 0 | 10 | 0 | 0 | 0 | 25 | 0 | 25 | 0 | 15 | 0 | 10 | 10 |
| Control | | | | | | | | | | | | | | | |
| $R_{channel}$ | 0 | 0 | 0 | 20 | 0 | 0 | 0 | 0 | 0 | 0 | 0 | 0 | 0 | 0 | 0 |
| $G_{channel}$ | 10 | 0 | 0 | 0 | 10 | 0 | 10 | 10 | 0 | 10 | 0 | 0 | 0 | 0 | 0 |
| $B_{channel}$ | 15 | 0 | 0 | 10 | 30 | 0 | 15 | 10 | 20 | 0 | 0 | 10 | 20 | 15 | 15 |

Example 9

Detection DNT in Liquid Phase

The colorimetric sensor array can be also use for screening of most commonly used explosives and organic compounds in the real-time format in liquid phase. The signal of relevant reactions which depending on color changes can be obtained faster in liquid phase than in gas phase. Since the chemo-selective compounds have strong donor-acceptor properties it is important to evaluate the interaction between chemo-selective compounds, applied solvents and membrane stability.

Figure 5:
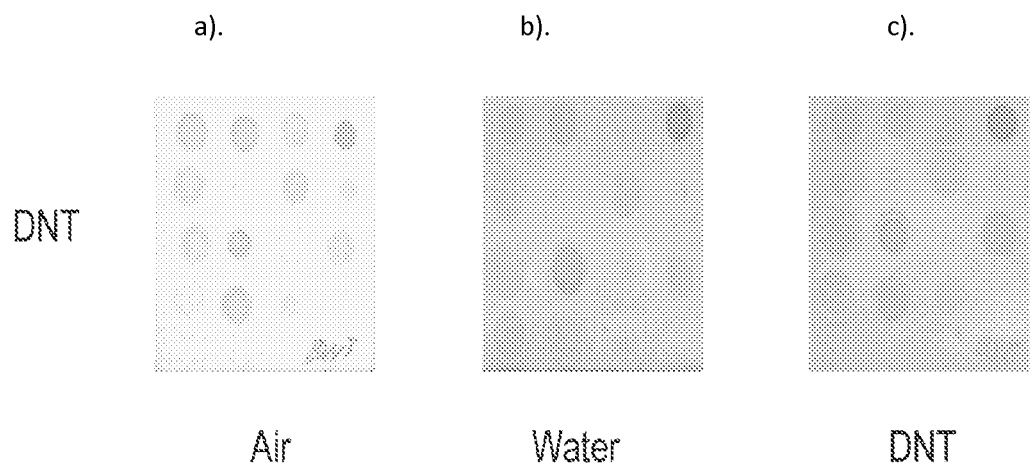
FIG. 5 shows the colorimetric sensor array obtained in gas and liquid phases after the exposure (5 sec) to DNT, water and a mixture thereof. a) The colorimetric sensor array obtained after exposure to DNT in gas phase; b) The colorimetric sensor array obtained after exposure to Milli-Q water; c) The colorimetric sensor array obtained after exposure to DNT dissolved in Milli-Q water.

For detection of DNT in liquid phase 15 chemo-selective compounds were immobilized on a solid support, a silica gel membrane, as shown in FIG. 1. To perform the survey 50 mg of DNT was dissolved in 0.5 mL of 96.9% ethanol, after the solution of DNT in ethanol was dissolved in 4.5 mL of Milli-Q water. Experiments were performed at room temperature. The silica gel membrane with immobilized compounds was dipped into solutions of DNT and remained there for 5 sec, after the exposure the chemo-selective compounds changed color (FIG. 5). Pictures were scanned twice through an ordinary flatbed scanner (Epson V750-M Pro Perfection scanner) first time after immobilization of chemo-selective compounds and second time after the analyte exposure. Almost each chosen dye reacted chemo-selectively with the analyte of interest.

Example 10

Statistical Analysis of Data

Data obtained with the colorimetric sensor array has been statistically evaluated by using the principal component analysis (PCA) method. PCA is a simple, non-parametric method which is relevant to extract data among different analytes into the minimum number of dimensions. In order to apply this method the difference maps must be represented as a matrix. As described earlier, each difference map can be represented using 45 color numbers hence each difference map corresponds to a vector is a 45 dimensional space (each map contains 15 dyes and each dye yields 3 values). We then construct a data matrix where each column corresponds to a difference map. PCA was applied to this data matrix.

Figure 6:
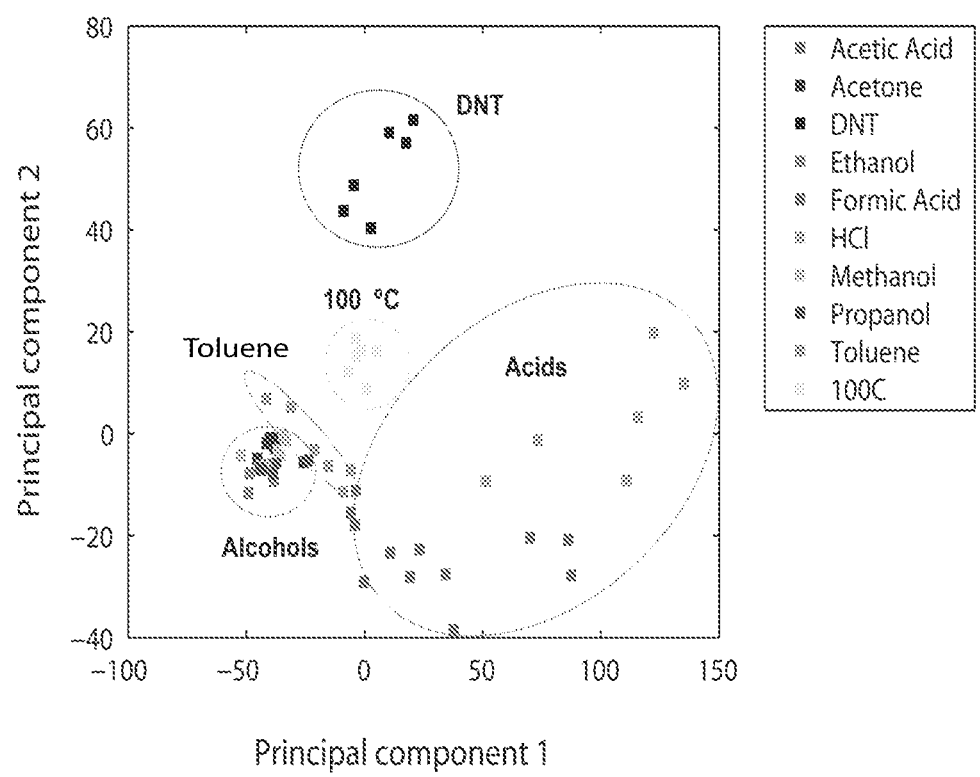
FIG. 6 shows the Principal Component Analysis of the colorimetric sensor array obtained from the response results of volatile organic compounds (VOCs) and DNT, at saturated vapour pressure.

According to the statistical analysis the overlap in the response for different analytes is insignificant (FIG. 6). FIG. 6 shows the PCA plot for the 1st to the 2nd principal components (PC) for a few select of the analytes. Using principal components 1 and 2 we see that 100° C., hydrochloric acid, formic acid, acetic acid, toluene and DNT, groups tightly into clusters. Acetone, methanol, ethanol and propanol however are all grouped into the same cluster, but the cumulative density function analysis enables us to distinguish between these 4 analytes as well (FIG. 6).

Although the present invention has been described in connection with the specified embodiments and aspect, it should not be construed as being in any way limited to the presented examples. The scope of the present invention is set out by the accompanying claim set.

The invention claimed is:

1. A colorimetric multisensor array comprising: a gas which comprises a detectable analyte, and at least two different compounds chemo-selective for said detectable analyte, wherein each of said chemo-selective compounds is capable of a change in color when exposed to said detectable analyte, and wherein said gas is in contact with said at least two different chemo-selective compounds and said at least two different chemo-selective compounds are represented by the general formulas 1) and 2) immobilized on a solid support spatially separated and individually addressable:

1)
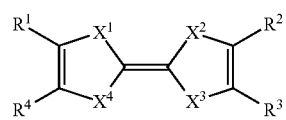

2)
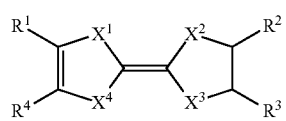

wherein, $X^1$, $X^2$, $X^3$, and $X^4$ each independently represents a hetero atom selected from the group consisting of sulfur and selenium;

and wherein the substituents $R^1$-$R^4$ of general formula 1) are:

$R^1$ is a substituent selected from the group consisting of hydrogen; halogen; $C_1$-$C_4$-alkyl; $C_1$-$C_{20}$- alkylsulfanyl; 2-substituted ethylsulfanyl, wherein the substituents are selected from the group consisting of carboxamide, cyano, hydroxy, amino, (N-benzoyl)amino, halogen, methylthio, phenylcarboxy, and phenoxycarbonyl; 2-(methylthio)ethylsulfanyl copper bromide; benzoylsulfanyl; methoxycarbonyl; cyano; carboxy; phenyl; benzyl; phenyl para-substituted by methoxy or halogen; and (4'- {[7-(2-cyanoethylthio)-2,3-dimethoxy-carbonyl-6-thio-methylene ]tetrathiafulvalene}-4-bipyridine)methylsulfanyl;

$R^2$ is a substituent selected from the group consisting of hydrogen; halogen; $C_1$-$C_4$-alkyl; $C_1$-$C_{20}$- alkylsulfanyl; 2-substituted ethylsulfanyl, wherein the substituents are selected from the group consisting of cyano, hydroxy, amino, (N-benzoyl)amino, halogen, methylthio, phenylcarboxy, phenoxycarbonyl, and (4-nitrophenyl); benzoylsulfanyl; cyano; carboxy; methoxycarbonyl; phenyl; benzyl; and phenyl para-substituted by methoxy or halogen;

$R^3$ is a substituent selected from the group consisting of hydrogen; halogen; $C_1$-$C_4$-alkyl; $C_1$-$C_{20}$- alkylsulfanyl; 2-substituted ethylsulfanyl wherein the substituents are selected from the group consisting of cyano, hydroxy, amino, (N-benzoyl)amino, halogen, methylthio, phenylcarboxy, phenoxycarbonyl, and (4-nitrophenyl); benzoylsulfanyl; methoxycarbonyl; cyano; carboxy; unsubstituted phenyl and phenyl para-substituted by halogen;

$R^4$ is a substituent selected from the group consisting of hydrogen; halogen; $C_1$-$C_4$-alkyl; $C_1$-$C_{20}$- alkylsulfanyl; 2-substituted ethylsulfanyl wherein the substituents are selected from the group consisting of cyano, carboxamide, hydroxy, amino, (N-benzoyl)amino, halogen, methylthio, phenylcarboxy, phenoxycarbonyl; benzoylsulfanyl; benzyl; methoxycarbonyl; cyano; and carboxy; or $R^1$ and $R^2$ together form a group selected from the group consisting of:

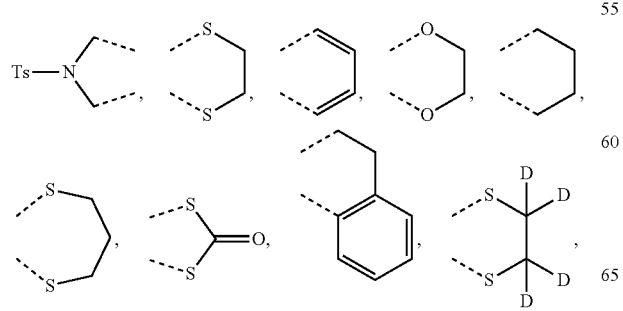

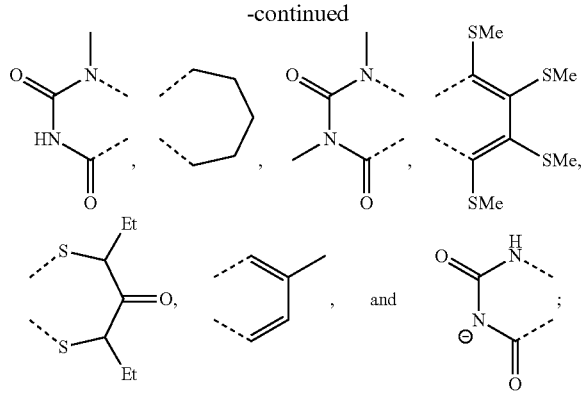

$R^2$ and $R^3$ together form a group selected from the group consisting of:

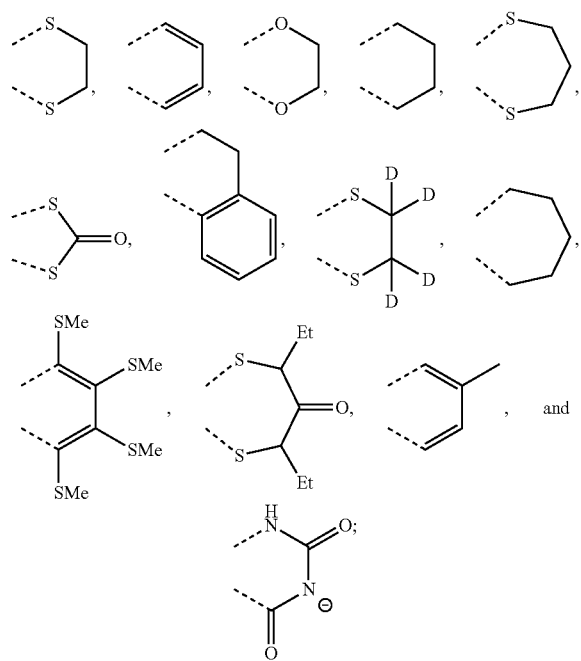

wherein the substituents $R^1$-$R^4$ of general formula 2) are:

$R^2$ is a substituent selected from the group consisting of methoxycarbonyl; $C_1$-$C_{20}$-alkylsulfanyl;

and 2-substituted ethylsulfanyl, wherein the substituents are selected from the group consisting of 4-nitrophenyl and 2-(2-methoxyethoxy)ethoxy;

$R^3$ is a substituent selected from the group consisting of $C_1$-$C_{20}$-alkylsulfanyl; 2-substituted ethylsulfanyl, wherein the substituents are selected from the group consisting of 4-nitrophenyl and 2-(2-methoxyethoxy)ethoxy; and methoxycarbonyl;

$R^1$ and $R^4$ together form a group selected from the group consisting of:

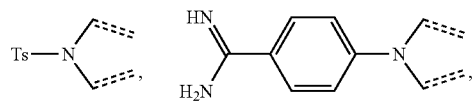

-continued

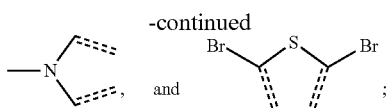

and the at least two compounds have a molecular weight below 1700.

2. The multisensor array according to claim 1, wherein $R^1$-$R^4$ of general formula 1) are:

$R^1$ is a substituent selected from the group consisting of hydrogen; $C_1$-$C_4$-alkyl; methoxycarbonyl; 2-substituted ethylsulfanyl, wherein the substituents are selected from the group consisting of carboxamide and cyano; phenyl; phenyl para-substituted by methoxy or halogen; and (4'- {[7-(2-cyanoethylthio)-2,3-dimethoxy-carbonyl-6-thio-methylene]tetrathiafulvalene}-4-bipyridine)methylsulfanyl;

$R^2$ is a substituent selected from the group consisting of hydrogen; $C_1$-$C_4$-alkyl; methoxycarbonyl; $C_1$-$C_{20}$-alkylsulfanyl; 2-substituted ethylsulfanyl, wherein the substituents are selected from the group consisting of 4-nitrophenyl and cyano; phenyl; and phenyl para-substituted by methoxy or halogen;

$R^3$ is a substituent selected from the group consisting of hydrogen; $C_1$-$C_4$-alkyl; methoxycarbonyl; $C_1$-$C_{20}$-alkylsulfanyl; 2-substituted ethylsulfanyl, wherein the substituents are selected from the group consisting of 4-nitrophenyl and cyano; phenyl; and phenyl para-substituted by halogen; and $R^4$ is a substituent selected from the group consisting of hydrogen; $C_1$-$C_4$-alkyl; methoxycarbonyl; and 2-substituted ethylsulfanyl, wherein the substituents are selected from the group consisting of carboxamide and cyano; or $R^1$ and $R^4$ together form:

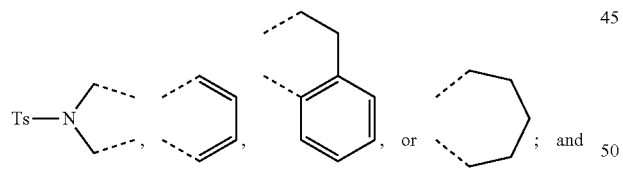

$R^2$ and $R^3$ together form a group selected from the group consisting of:

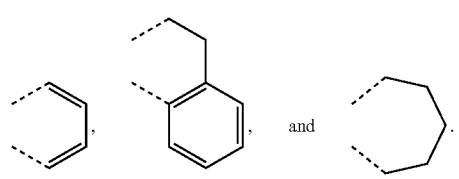

3. The multisensor array according to claim 1, comprising at least two different chemo-selective compounds of general formula 1) and 2) selected from the group consisting of:

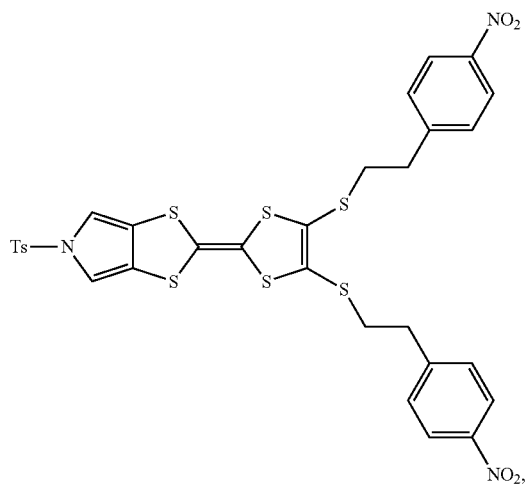

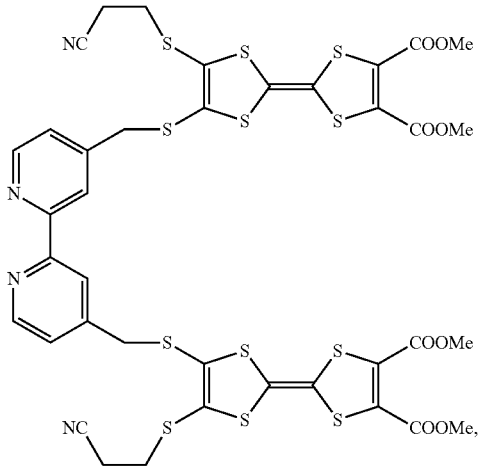

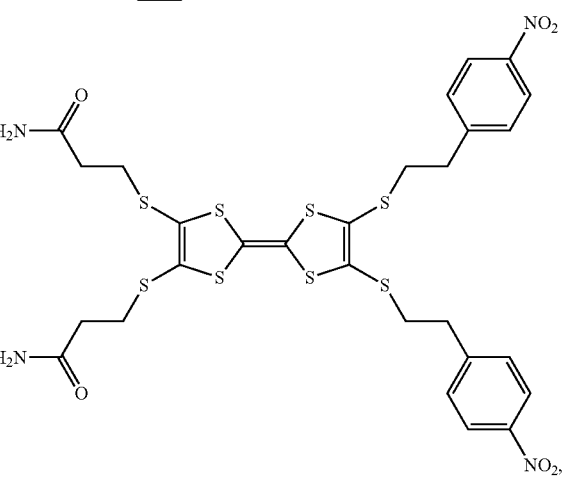

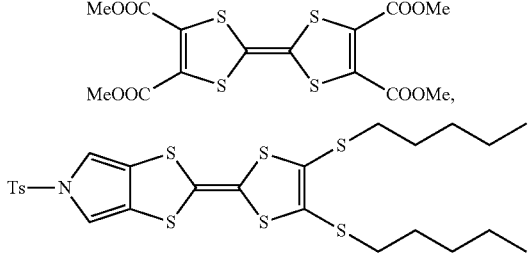

-continued
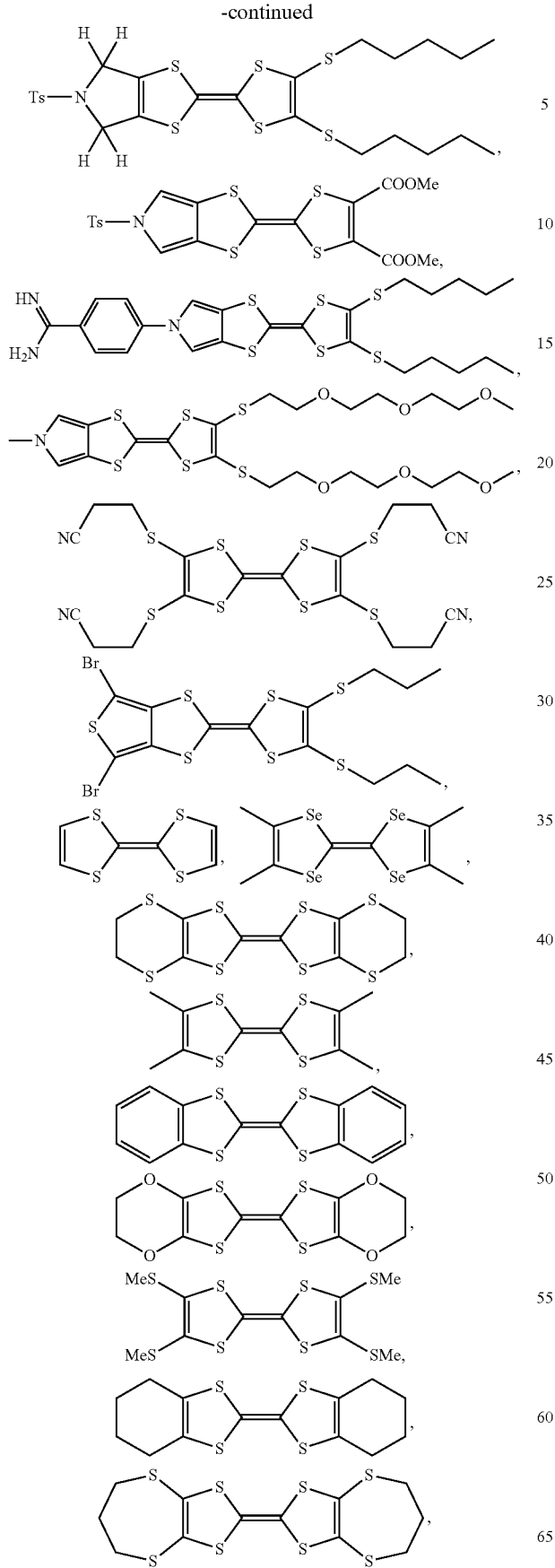
-continued
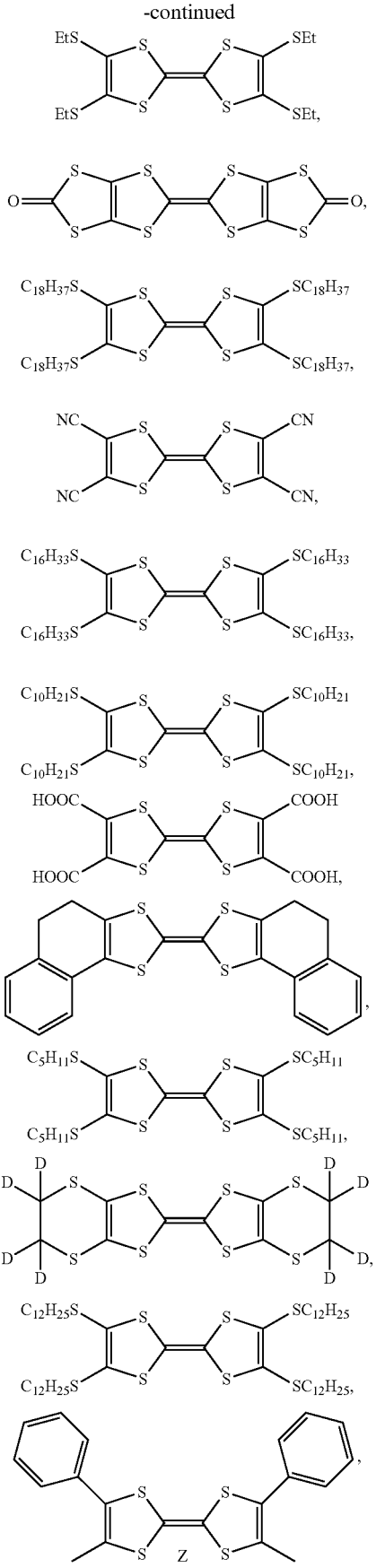

97
-continued
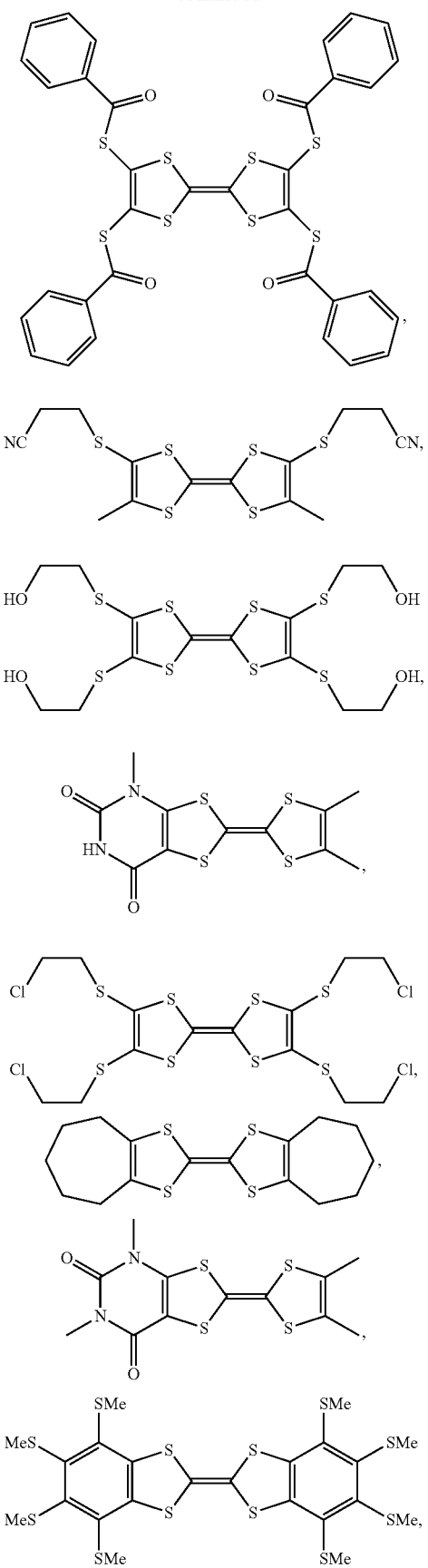
98
-continued
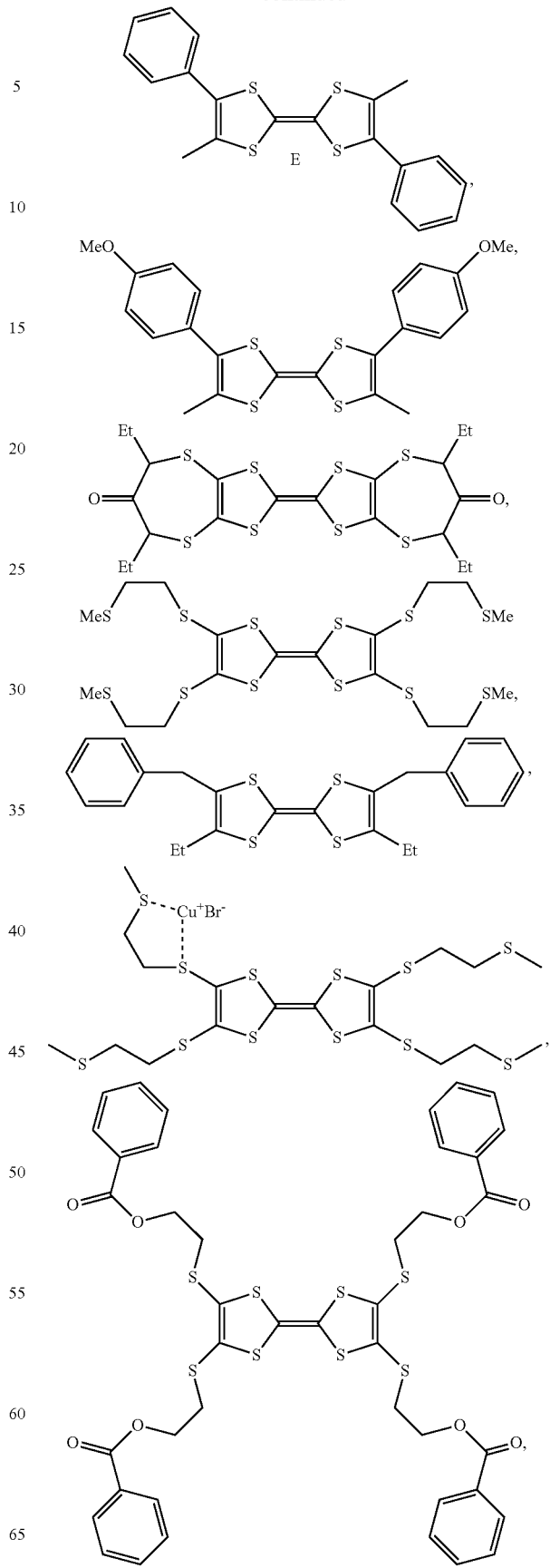

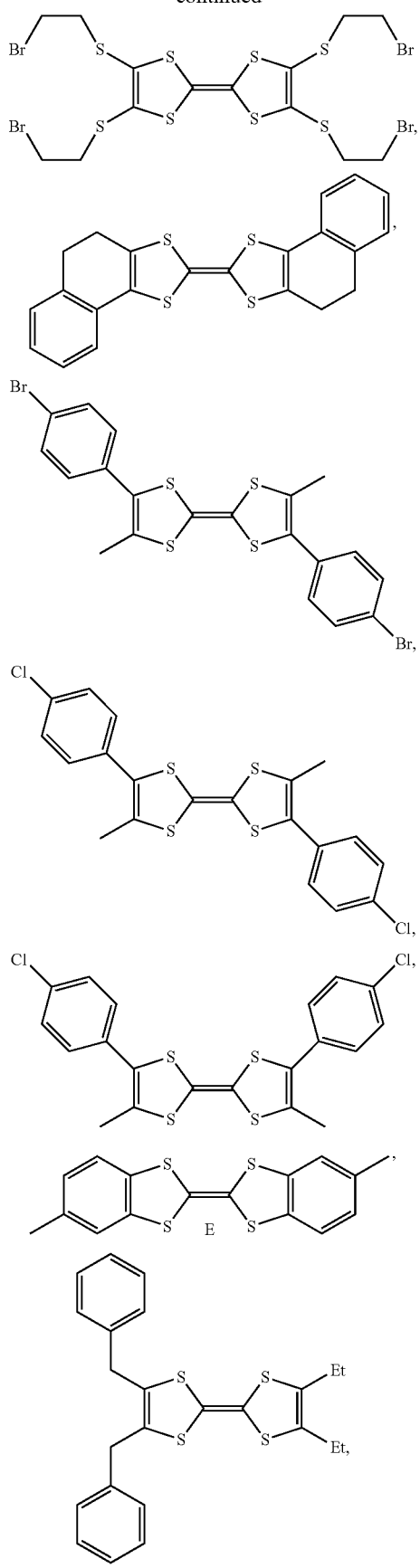
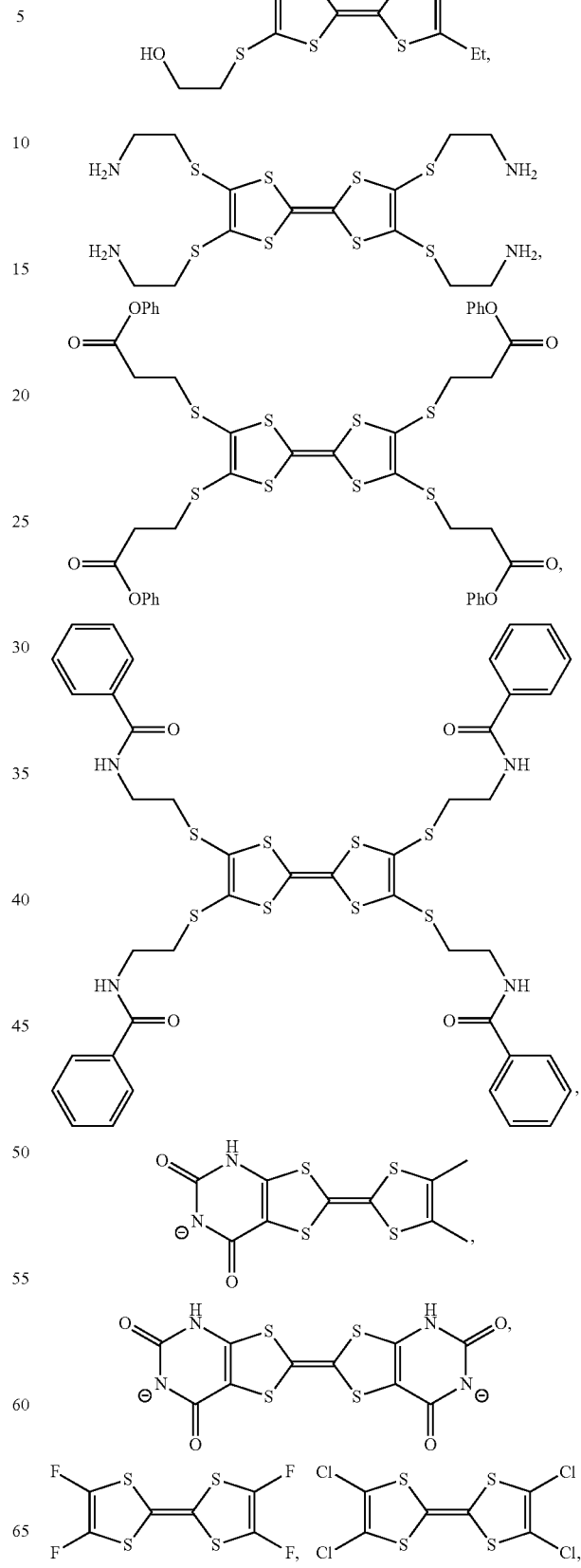

101
-continued
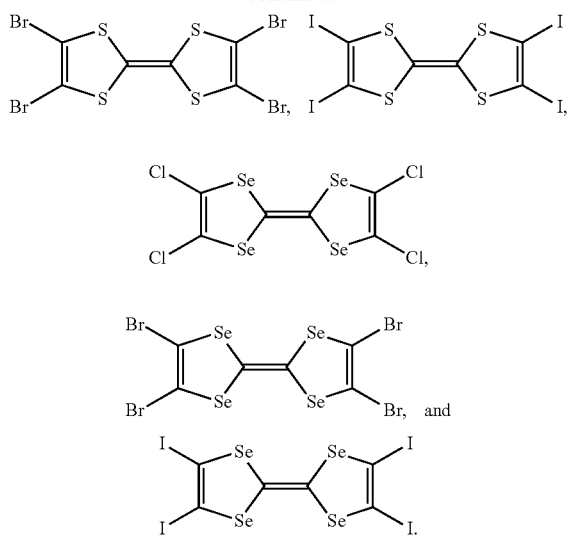
4. The multisensor array according to claim 3, comprising at least fifteen different chemo-selective compounds.
5. The multisensor array according to claim 3, comprising at least the following compounds:
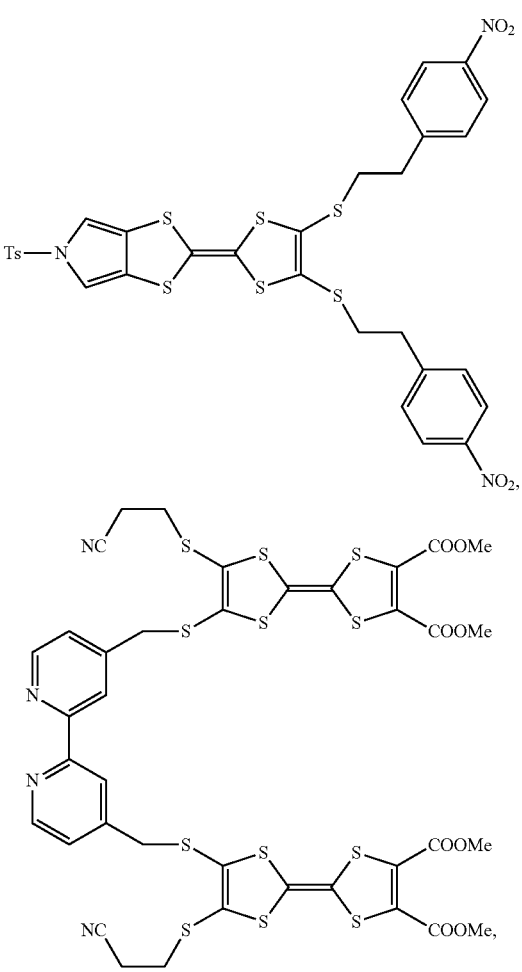
102
-continued
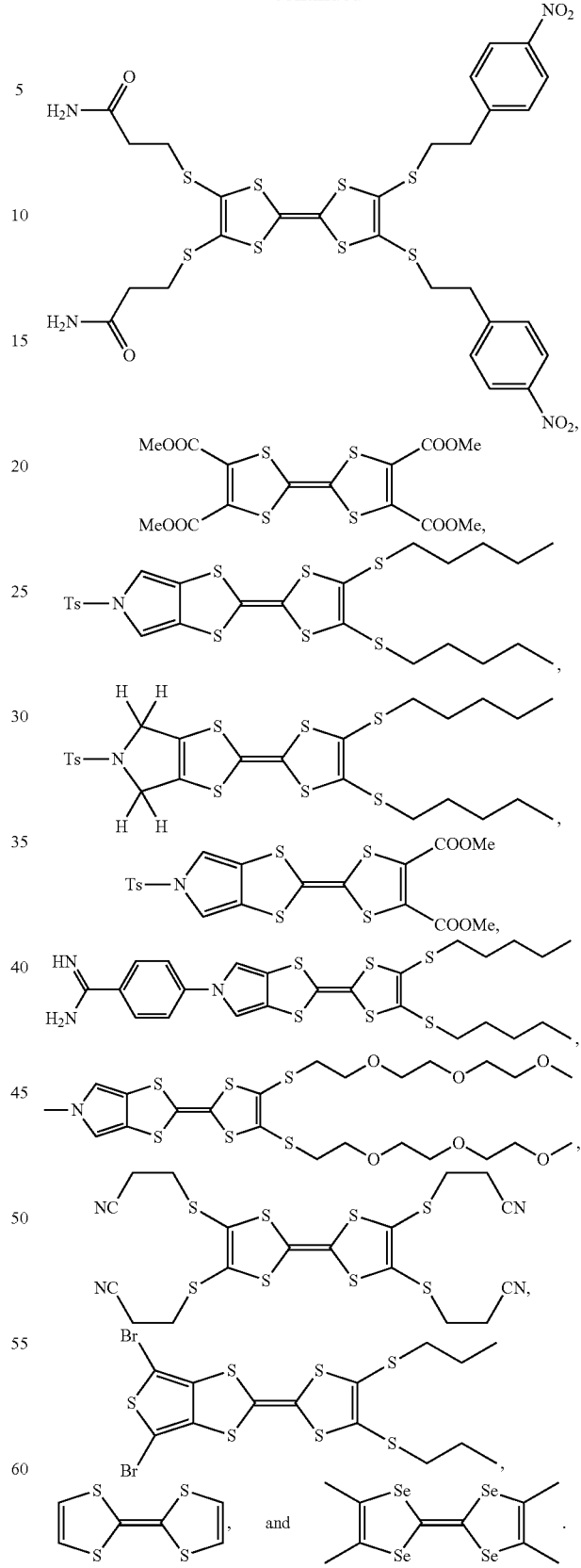
6. A method of detecting and/or identifying one or more analytes in a gas sample comprising:

providing the multisensor array according to claim 1, wherein the gas comprised in the multisensor array is from a gas sample that comprises one or more analytes; and detecting and/or identifying said one or more analytes in said gas sample.

7. The method according to claim 6, wherein $R^1$-$R^4$ of general formula 1) are:

$R^1$ is a substituent selected from the group consisting of hydrogen; $C_1$-$C_4$-alkyl; methoxycarbonyl; 2-substituted ethylsulfanyl, wherein the substituents are selected from the group consisting of carboxamide and cyano; (4'-{[7-(2-cyanoethylthio)-2,3-dimethoxy-carbonyl-6-thio-methylene]tetrathiafulvalene}-4-bipyridine)methylsulfanyl; phenyl; and phenyl parasubstituted by methoxy or halogen;

$R^2$ is a substituent selected from the group consisting of hydrogen; $C_1$-$C_4$-alkyl; methoxycarbonyl; $C_1$-$C_{20}$-alkylsulfanyl; phenyl; phenyl para-substituted by methoxy or halogen; and 2-substituted ethylsulfanyl, wherein the substituents are selected from the group consisting of 4-nitrophenyl and cyano;

$R^3$ is a substituent selected from the group consisting of hydrogen; $C_1$-$C_4$-alkyl; methoxycarbonyl; $C_1$-$C_{20}$-alkylsulfanyl; 2-substituted ethylsulfanyl, wherein the substituents are selected from the group consisting of 4-nitrophenyl, and cyano; phenyl; and phenyl para-substituted by halogen; and $R^4$ is a substituent selected from the group consisting of hydrogen; $C_1$-$C_4$-alkyl; methoxycarbonyl; and 2-substituted ethylsulfanyl, wherein the substituents are selected from the group consisting of carboxamide and cyano; or $R^1$ and $R^4$ together form:

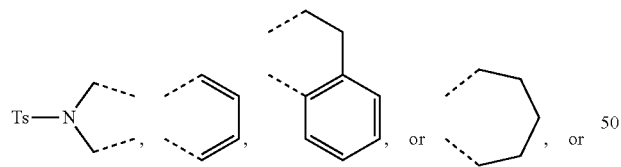

$R^2$ and $R^4$ together form a group selected from the group consisting of:

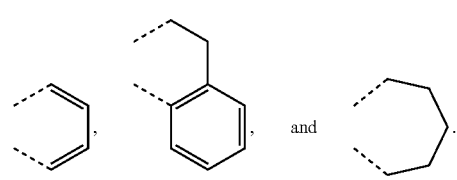

8. The method according to claim 7, wherein at least the following compounds:

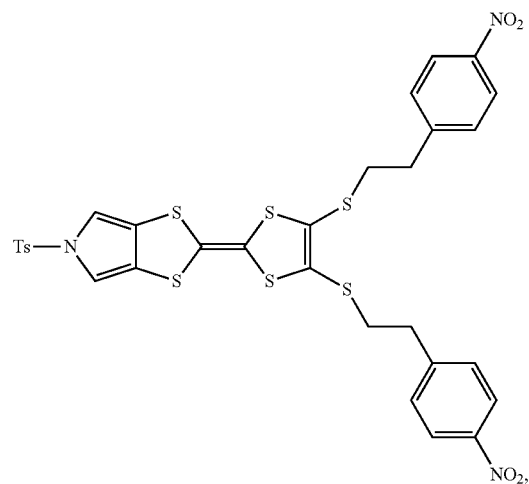

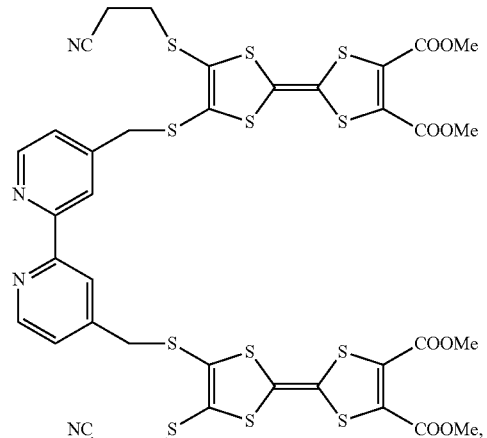

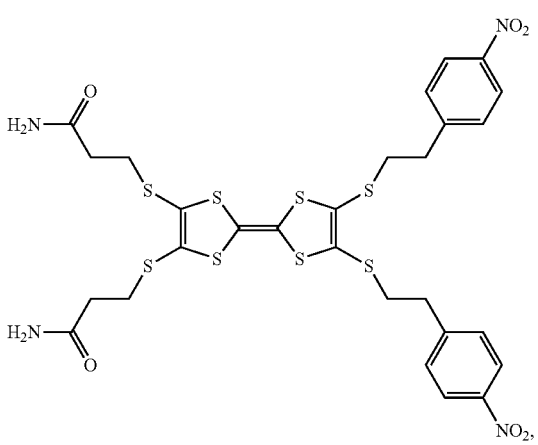

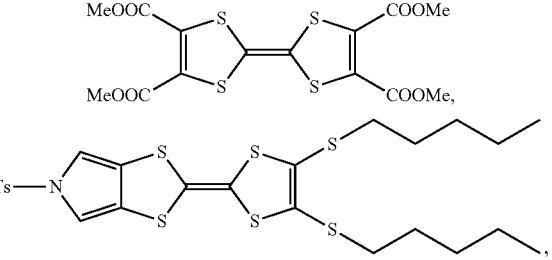

105
-continued
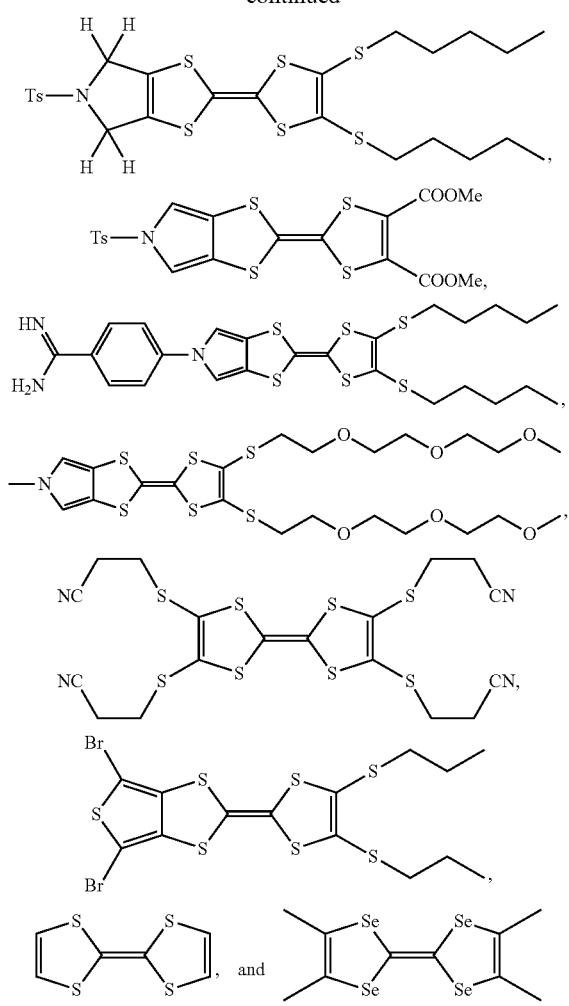
are comprised in the multisensor array for detection and /or identifying of analyte(s) in gas phase.
9. The method according to claim 6, wherein the at least two different chemoselective compounds of general formulas 1) and 2) are selected from the group consisting of:
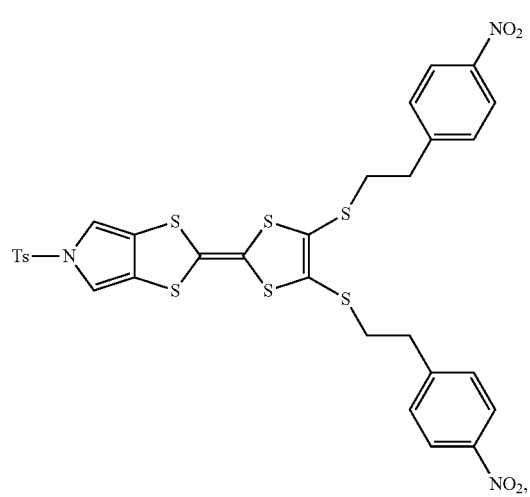
106
-continued
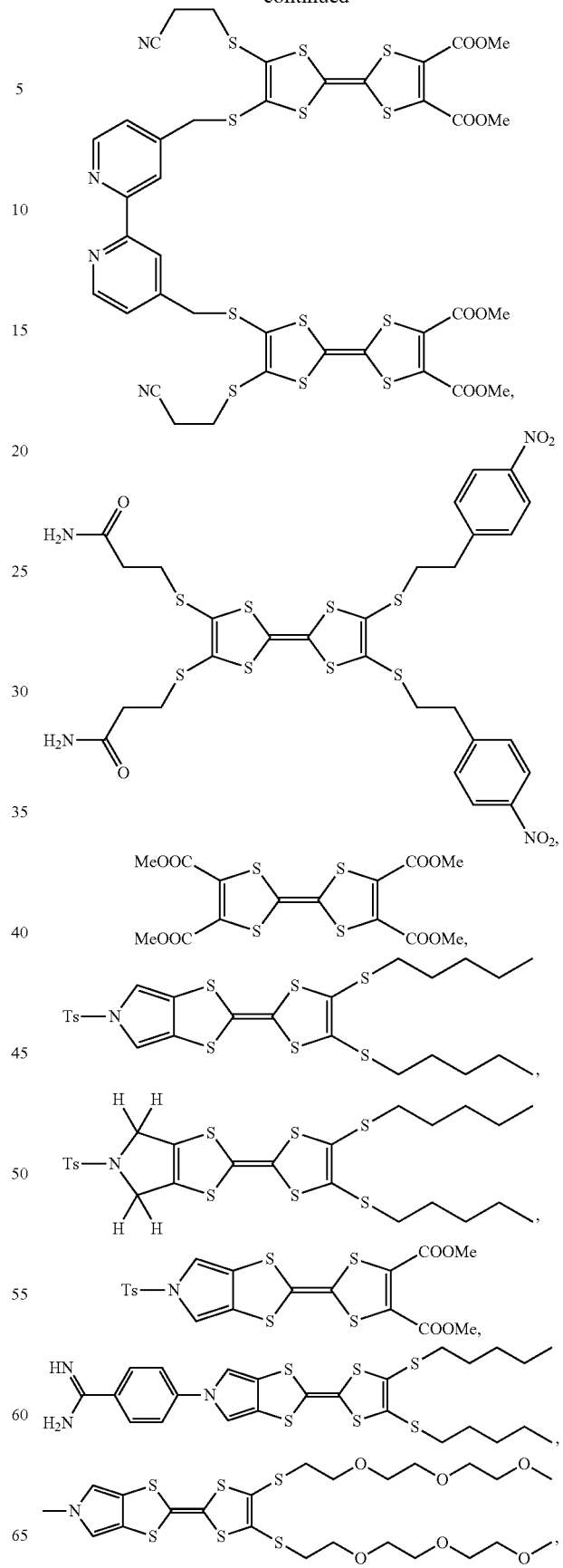

107
-continued
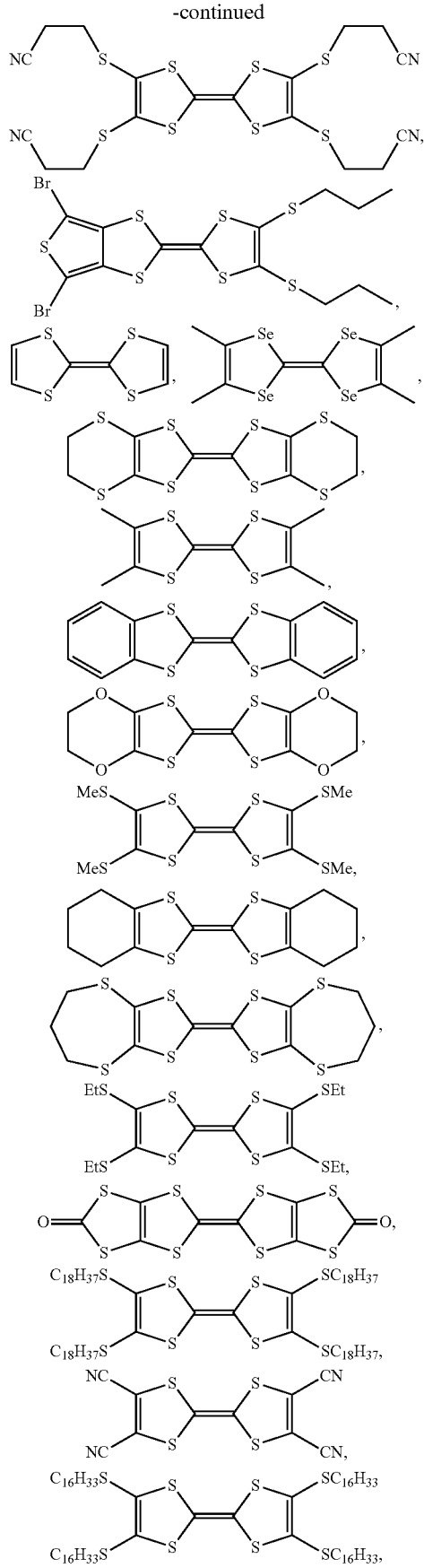
108
-continued
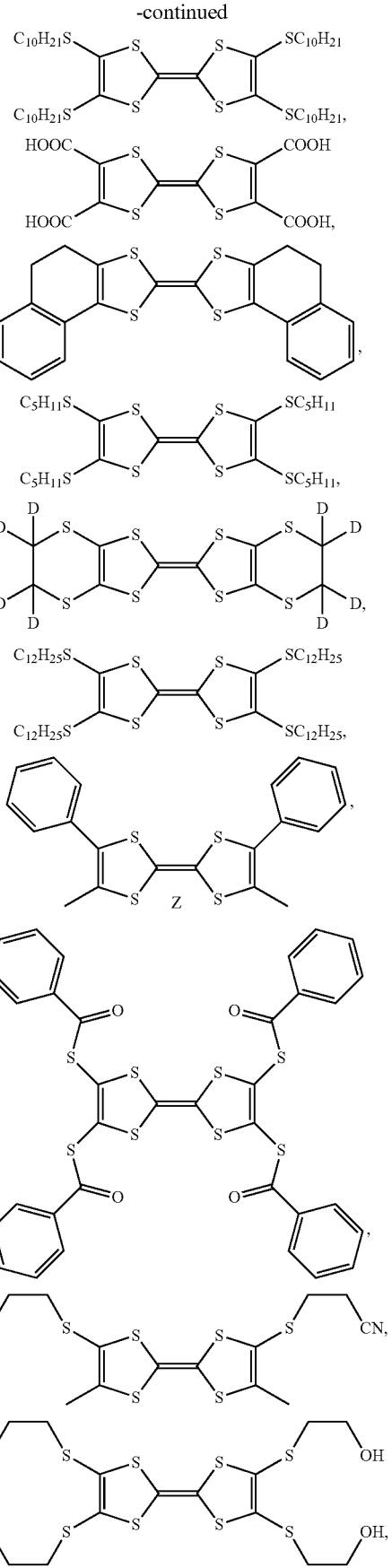

109
-continued
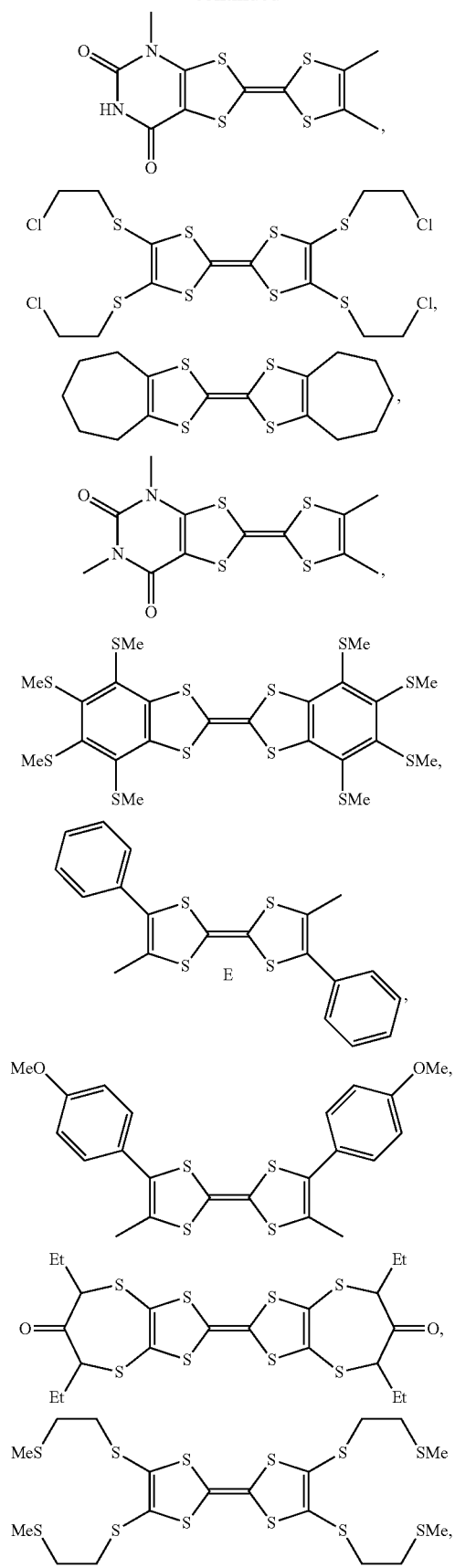
110
-continued
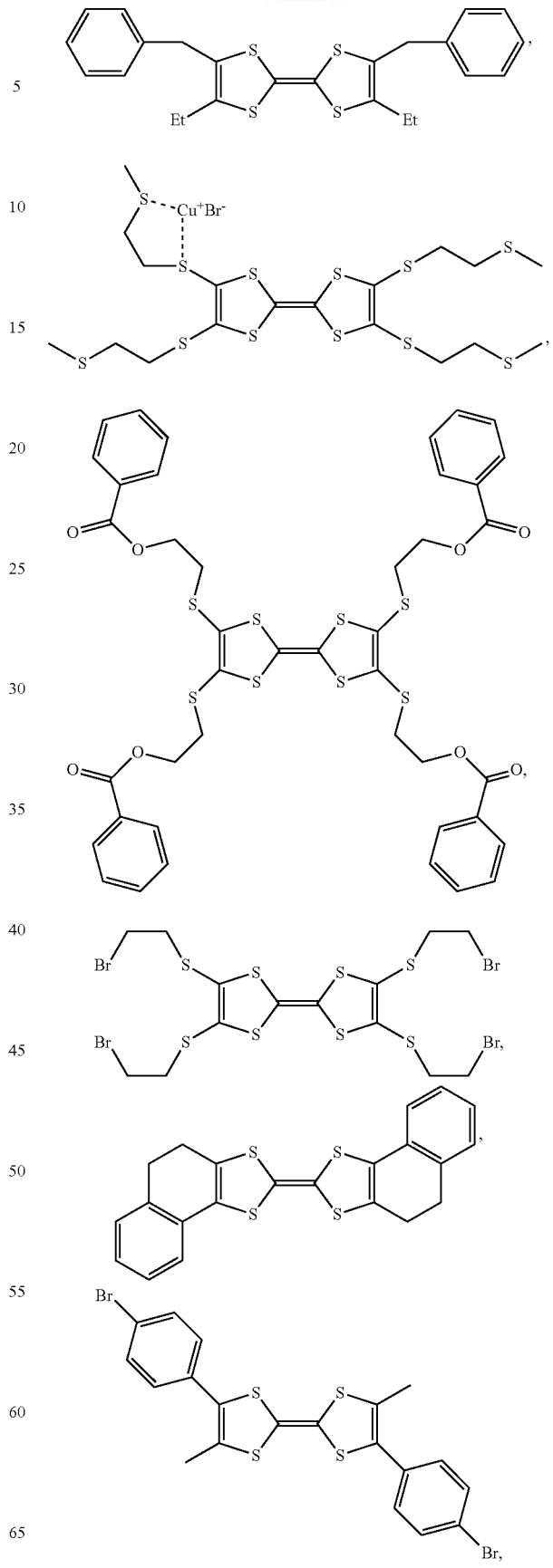

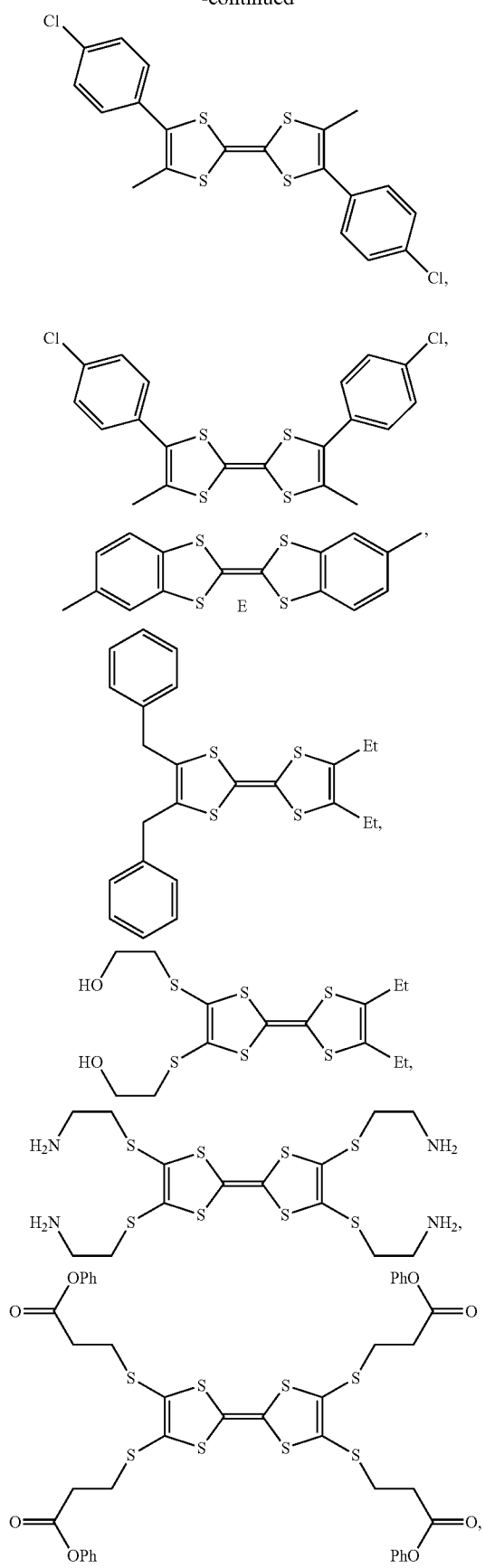

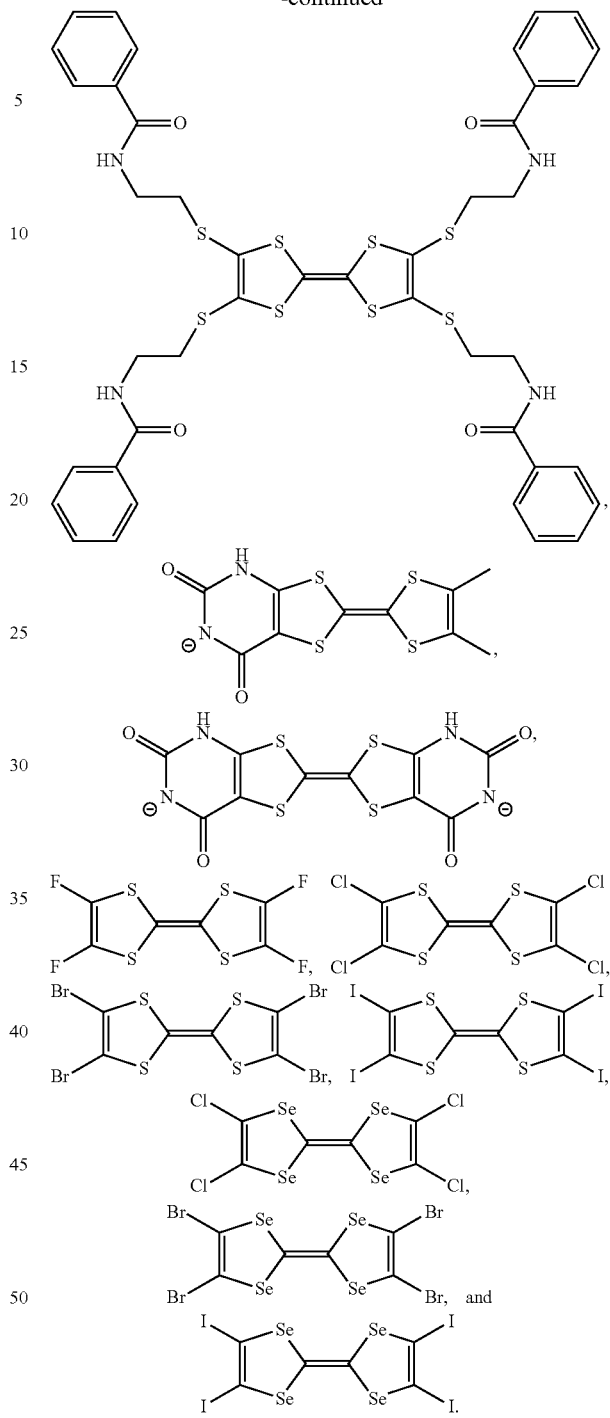

10. The method according to claim 9, wherein at least fifteen different chemo-selective compounds are comprised in the multisensor array for detection and/or identifying of analyte(s) in gas phase.

11. The method according to claim 6, wherein said one or more analytes are selected from the group consisting of amines . . . pollutants, and exhaust gasses from burning fuels.

12. The method according to claim 6, wherein said sample is obtained from a food.

13. The method according to claim 6, wherein said sample is a vapour obtained from a plastic material or furniture.

\* \* \* \* \*